US011242514B2

(12) United States Patent
Pérez-Jiménez

(10) Patent No.: US 11,242,514 B2
(45) Date of Patent: Feb. 8, 2022

(54) ENDOCELLULASES AND USES THEREOF

(71) Applicant: Asociación Centro de Investigación Cooperativa en Nanociencias "CIC nanoGUNE", San Sebastián (ES)

(72) Inventor: Raúl Pérez-Jiménez, San Sebastián (ES)

(73) Assignee: Asociación Centro de Investigación Cooperativa en Nanociencias "CIC nanoGUNE", San Sebastián (ES)

( * ) Notice: Subject to any disclaimer, the term of this patent is extended or adjusted under 35 U.S.C. 154(b) by 0 days.

(21) Appl. No.: 16/069,977

(22) PCT Filed: Jan. 16, 2017

(86) PCT No.: PCT/EP2017/050825
§ 371 (c)(1),
(2) Date: Jul. 13, 2018

(87) PCT Pub. No.: WO2017/121902
PCT Pub. Date: Jul. 20, 2017

(65) Prior Publication Data
US 2019/0062717 A1 Feb. 28, 2019

(30) Foreign Application Priority Data

Jan. 15, 2016 (EP) .................... 16382018

(51) Int. Cl.
| | | |
|---|---|---|
| C12N 9/42 | (2006.01) | |
| C12N 15/56 | (2006.01) | |
| C12N 1/15 | (2006.01) | |
| C12P 19/14 | (2006.01) | |
| C12P 19/02 | (2006.01) | |
| C12P 7/10 | (2006.01) | |
| C11D 3/386 | (2006.01) | |
| C12P 19/04 | (2006.01) | |
| C12P 19/12 | (2006.01) | |
| C13K 1/02 | (2006.01) | |

(52) U.S. Cl.
CPC ........ *C12N 9/2437* (2013.01); *C11D 3/38645* (2013.01); *C12P 7/10* (2013.01); *C12P 19/02* (2013.01); *C12P 19/04* (2013.01); *C12P 19/12* (2013.01); *C12P 19/14* (2013.01); *C12Y 302/01004* (2013.01); *C13K 1/02* (2013.01); *Y02E 50/10* (2013.01)

(58) Field of Classification Search
None
See application file for complete search history.

(56) References Cited

U.S. PATENT DOCUMENTS

| | | |
|---|---|---|
| 5,612,055 A | 3/1997 | Bedford et al. |
| 6,162,782 A | 12/2000 | Clarkson et al. |
| 6,599,722 B2 | 7/2003 | Boston et al. |

FOREIGN PATENT DOCUMENTS

| | | | |
|---|---|---|---|
| CN | 103074356 A | | 5/2013 |
| CN | 104480135 A | | 4/2015 |
| CN | 108823188 A | * | 11/2018 |
| CN | 111004793 A | * | 4/2020 |
| EP | 0473545 A2 | | 3/1992 |
| EP | 1222256 B1 | | 5/2005 |
| WO | 9206209 A1 | | 4/1992 |
| WO | 9720920 A1 | | 6/1997 |
| WO | 9821339 A1 | | 5/1998 |
| WO | 2006101584 A2 | | 9/2006 |
| WO | 2007118935 A1 | | 10/2007 |
| WO | 2008005529 A2 | | 1/2008 |
| WO | 2009108941 A2 | | 9/2009 |
| WO | 2011109905 A1 | | 9/2011 |
| WO | 2012088159 A2 | | 6/2012 |
| WO | WO-2013167581 A1 | * | 11/2013 ............... C09K 8/02 |

OTHER PUBLICATIONS

Zhang et al., Structure 26:1474-1485, 2018 (Year: 2018).*
Srisodsuk et al., J. Biol. Chem. 268:20756-20761, 1993 (Year: 1993).*
Garate, N., "Ancestral sequence reconstruction for protein engineering: improving celulases for biomass hydrolysis", Doctoral Dissertation, CIC NanoGUNE, 2017 (Year: 2017).*
Barruetabena et al., "Resurrection of efficient Precambrian endoglucanases for lignocellulosic biomass hydrolysis", Comm. Chem. 2:76, 13 pages, 2019 (Year: 2019).*
UniProt Database Accession No. A0A093T0V7, Dec. 2015, 2 pages (Year: 2015).*
Machine translation of CN 108823188A, obtained from Google Patents on Feb. 1, 2021, 10 pages (Year: 2021).*
Singh et al., Curr. Protein Pept. Sci. 18:1-11, 2017 (Year: 2017).*
Goswami et al., Front. Onc. 9:297, 2019, 25 pages (Year: 2019).*
Guo et al., Comp. Struct. Biotechnol. J. 15:161-167, 2017 (Year: 2017).*
International Search Report and Written Opinion for PCT/EP2017/050825, dated Apr. 6, 2017.
Altschul, et al. "Multiple Alignment and Phylogenetic Trees—Local Alignment Statistics", Methods in Enzymology, 1996, vol. 266, pp. 460-480.

(Continued)

*Primary Examiner* — David Steadman
(74) *Attorney, Agent, or Firm* — Pilloff Passino & Cosenza LLP; Sean A. Passino; Rachel K. Pilloff

(57) ABSTRACT

The invention relates to an endocellulase catalytic domain comprising the sequence of SEQ ID NO: 1 or a functionally equivalent variant of said catalytic domain that substantially maintains or improves its catalytic activity. The invention also relates to a polypeptide, a nucleic acid, an expression cassette, a vector or a host cell. Additionally, the invention relates to the use of an endocellulase catalytic domain or the polypeptide of the invention for hydrolysing cellulose, producing bioethanol or as a detergent. The invention also relates to a method for hydrolysing cellulose and for producing bioethanol.

20 Claims, 8 Drawing Sheets

Specification includes a Sequence Listing.

(56) References Cited

OTHER PUBLICATIONS

Altschul, et al. "Gapped BLAST and PSI-BLAST: a new generation of protein database search programs", Nucleic Acids Research, 1997, vol. 25, No. 17, pp. 3389-3402.
Atschul, S. F. "Amino Acid Substitution Matrices from an Information Theoretic Perspective", J. Mol. Biol., 1991, vol. 219, pp. 555-565.
EMBL Database Accession No. KF240855—"Bacillus thuringiensis strain IARI-SP-6-endo-beta-1,4-glucanase gene, partial cds.", XP002756907, Oct. 2, 2013.
UniProt Database Accession No. U3R8L0—Endoglucanase; Flags: Fragment;, XP002756906, Dec. 11, 2013.
EMBL Database Accession No. KF240853, "Bacillus thuringiensis strain IARI-SP-6 endo-beta-1,4-glucanase gene, partial cds.", XP002756907, Oct. 2, 2013.
UniProt Database Accession No. P26224, Endoglucanase F; Cellulase F; Endo-1, 4-beta-glucanase; Precursor, XP002756911, May 1, 1992.
UniProt Database Accession No. F4FAV2, Endoglucanase, XP002756909, Jun. 28, 2011.
UniProt Database Accession No. U3RD83, Endoglucanase, XP002756904, Dec. 11, 2013.
UniProt Database Accession No. A0A0B2T1H3, Endoglucanase, XP002756903, Mar. 4, 2015.
UniProt Database Accession No. A0A0D0X703, Endoglucanase, XP002756910, Apr. 29, 2015.
Navarro, et al. "Nucleotide sequence of the cellulase gene celF of Clostridium thermocellum", Research Microbiology, 1991, vol. 142, pp. 927-936.
Geneseq Database Accession No. BCD39860, "Recombinant Streptomyces lydicus preparing cellulase, SEQ ID 4.", XP002756908, Oct. 8, 2015.
Drummond, et al. "Divergence Dating Tutorial with BEAST 2.0", Manual, Dec. 3, 2013.
Ghose, et al. "Measurement of Hemicellulase Activities Part 1: XYLANASES", Pure & Appl. Chem., 1987, vol. 59, No. 12, pp. 1739-1752.
Karlin, et al. "Methods for assessing the statistical significance of molecular sequence features by using general scoring schemes", Proc. Natl. Acad. Sci., Mar. 1990, vol. 87, pp. 2264-2268.
Karlin, et al. "Applications and statistics for multiple high-scoring segments in molecular sequences". Proc. Natl. Acad. Sci, Jun. 1993, vol. 90, pp. 5873-5877.
Kim, et al. "Enzyme-linked Assay of Cellulose-binding Domain Functions from Cellulomonas fimi on Multi-well Microtiter Plate", Biotechnology and Bioprocess Engineering, 2013, vol. 18, pp. 575-580.
Machida, et al. "Nucleotide Sequences of Saccharomycopsis fibuligera Genes for Extracellular beta-Glucosidases as Expressed in *Saccharomyces cerevisiae*", Applied and Environmental Microbiology, Dec. 1988, vol. 54, No. 12, pp. 3147-3155.
Maki, et al. "The prospects of cellulase-producing bacteria for the bioconversion of lignocellulosic biomass", Int. J. Biol. Sci., 2009, vol. 5, pp. 500-516.
Miller, G. "Use of Dinitrosalicylic Acid Reagent for Determination of Reducing Sugar", Analitical Chemistry, Mar. 1959, vol. 31, No. 3, pp. 426-428.
Morana, et al. "Cellulases from Fungi and Bacteria and their Biotechnological Applications", Biotechnology in Agriculture, Industry and Medicine; Chapter 1, Cellulase: Types, Actions, Mechanisms, and Uses; NOVA Science publishers, 2011.
Myers, et al. "Optimal alignments in linear space", Cabios, vol. 4, No. 1, 1988, pp. 11-17.
Needleman, et al. "A General Method Applicable to the Search for Similarities in the Amino Acid Sequence of Two Proteins", J. Mol. Biol., 1970, vol. 48, pp. 443-453.
Paml, Phylogenetic analysis by Maximum Likelihood, Feb. 2017, Manual, Version 4.9d.
Ronquist, et al. "MrBayes version 3.2 Manual: Tutorials and Model Summaries", Nov. 15, 2011.
Tamura, et al. "MEGA6: Moleclar Evolutionary Genetics Analysis Version 6.0", Mol. Biol. Evol., 2013, vol. 30, No. 12 pp. 2725-2729.
Van Dyk, et al. "A review of lignocellulose bioconversion using enzymatic hydrolysis and synergistic cooperation etween enzymes—Factors affecting enzymes, conversion and synergy", Biotechnology Advances, 2012, vol. 30, pp. 1458-1480.
Tang et al. "Limitation of the Development on Cellulose Hydrolysis by Cellulase Assay and Search for the True Cellulase Degrading Crystalline Cellulose"; Biotechnology in Agriculture, Industry and Medicine; Chapter 8; Cellulase Types, Actions, Mechanisms, and Uses, NOVA Science publishers, 2011.
Ng, et al. Cellulase: Types, Actions, Mechanisms and Uses; Biotechnology in Agriculture, Industry and Medicine; Chapter 9, Cellulase; Types, Actions, Mechanisms, and Uses, NOVA Science publishers, 2011.
Search Report in EP Application No. 16 38 2018, dated Apr. 25, 2016.

* cited by examiner

ENDOCELLULASES AND USES THEREOF

FIELD OF THE INVENTION

The present invention falls within the field of enzymes, particularly polypeptides comprising an endocellulase catalytic domain, and its use in the production of bioethanol.

BACKGROUND OF THE INVENTION

Over the past years, cellulose enzymes have attracted the interest of the scientific community as well as the industry due to their many biotechnological applications. Their production has increased exponentially and has encountered an important source of application in the production of bioethanol. Second-generation bioethanol made from lignocellulosic biomass is considered one of the most promising biofuels. However, the enzymatic hydrolysis of the cellulose component to liberate glucose for ethanol fermentation is one of the major barriers for the process to be economically competitive because of the cell wall recalcitrance of feedstock.

Efficient degradation of cellulosic biomass requires the synergistic action of the cellulolytic enzymes endocellulase, exocellulase and β-glucosidase. In order to increase bioethanol production, interest has been focused on the identification and optimization of fungal, yeast and bacterial cellulases and cellulolytic strains. Aside from traditional mutagenesis for improving the secretion level and enzymatic activities of cellulases, genetic engineering of strains and protein engineering on cellulase molecules enabled an increased yield. Bacterial and yeast cellulases are often preferred as these organisms have higher growth rates, although bacterial cellulases are able to deal better with the harsh conditions of industrial settings than eukaryotic ones, allowing higher rates of enzymatic hydrolysis, fermentation and product recovery.

Nevertheless, current cellulases have limited efficiency under industrial conditions. Therefore, there is still a need in the art for cellulases and endocellulases, in particular, with improved physicochemical and/or functional properties over existing naturally occurring and engineered cellulases.

SUMMARY OF THE INVENTION

In a first aspect, the invention relates to a polypeptide comprising an endocellulase catalytic domain, wherein the catalytic domain comprises the sequence of SEQ ID NO: 1 or a functionally equivalent variant thereof that substantially maintains or improves its catalytic activity.

In another aspect, the invention relates to a nucleic acid encoding a polypeptide according to the invention.

In another aspect, the invention relates to an expression cassette comprising the nucleic acid according to the invention, wherein said nucleic acid is under control of a suitable transcriptional and/or translational system.

In another aspect, the invention relates to a vector comprising the nucleic acid according to the invention.

In another aspect, the invention relates to a vector comprising the expression cassette according to the invention.

In another aspect, the invention relates to a host cell comprising the nucleic acid according to the invention.

In another aspect, the invention relates to a host cell comprising the expression cassette according to the invention.

In another aspect, the invention relates to a host cell comprising the vector according to the invention.

In another aspect, the invention relates to a method for hydrolysing cellulose comprising contacting a sample containing cellulose with a polypeptide according to the invention under suitable conditions for hydrolysing cellulose.

In another aspect, the invention relates to a method for producing bioethanol comprising
(i) contacting a sample containing cellulose with a polypeptide according to the invention under suitable conditions for hydrolysing cellulose, thereby obtaining endocellulase-treated cellulose,
(ii) converting the endocellulase-treated cellulose obtained in step (i) to cellobiose and/or cellotetraose using an exocellulase,
(iii) converting the cellobiose and/or cellotetraose obtained in step (ii) to glucose using a β-glucosidase, and
(iv) converting the glucose obtained in step (iii) to bioethanol in the presence of a yeast capable of producing bioethanol by fermentation of glucose.

In another aspect, the invention relates to a detergent composition comprising a polypeptide according to the invention and a surfactant.

In another aspect, the invention relates to the use of a polypeptide according to the invention for hydrolysing cellulose, for producing ethanol or as a detergent.

DETAILED DESCRIPTION OF THE INVENTION

Figure 1:
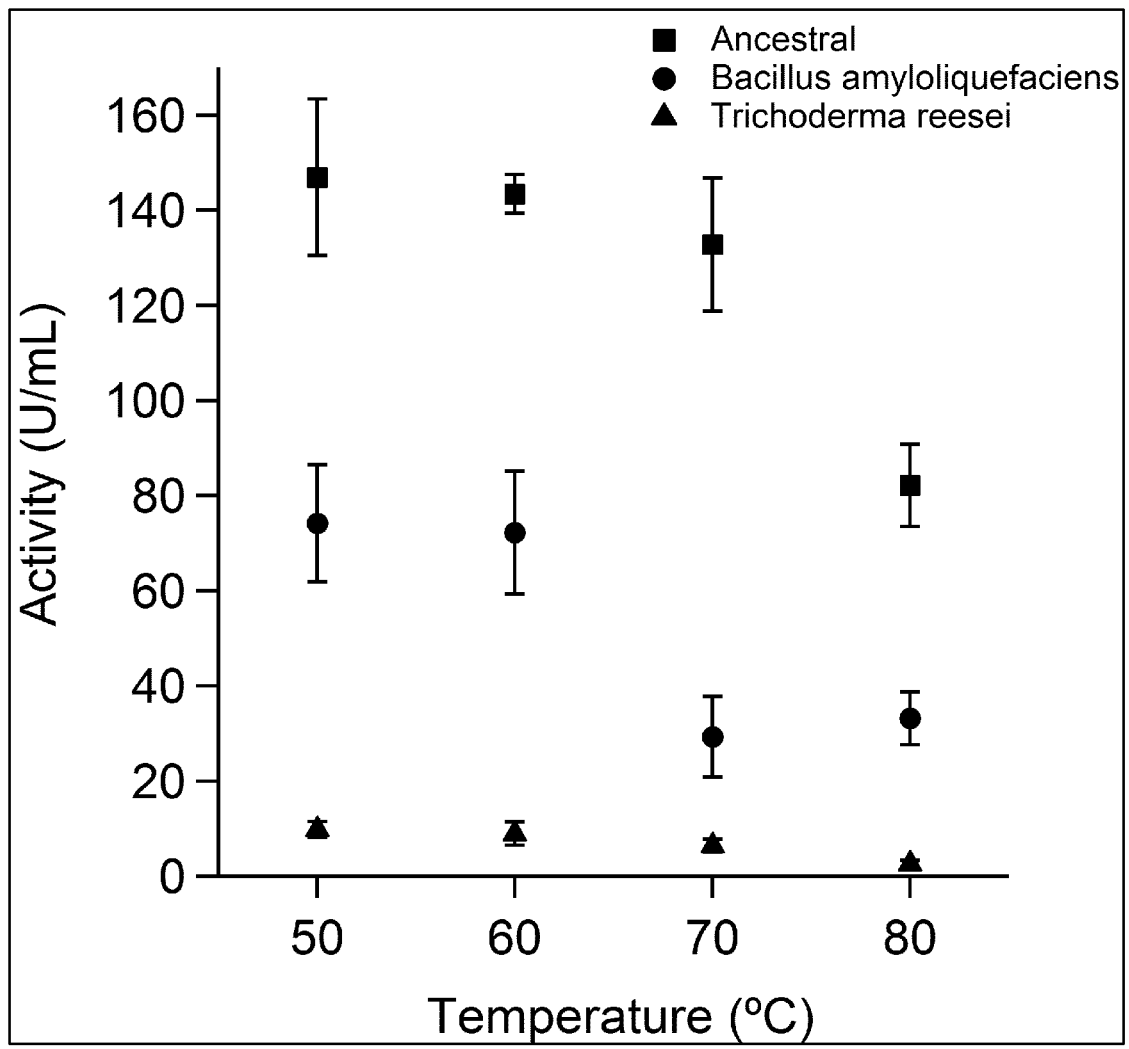
FIG. 1: Activity in U/mL of three different endocellulases: ancestral (Endocellulase catalytic domain (SEQ ID NO: 2)), square; *Bacillus amyloliquefacienes*, circle and *Trichoderma reesei*, triangle, measured at different temperatures (50° C., 60° C., 70° c. and 80° C.) with Megazyme endo-cellulase assay kit.

The inventors have developed polypeptides comprising endocellulase catalytic domains showing substantially improved physicochemical properties over existing naturally occurring and commercial endocellulases. Surprisingly, these polypeptides maintain or show an improved catalytic activity even under conditions of acidic pH and/or high temperatures, as shown in Example 1. These properties make the endocellulase catalytic domains of the invention ideal for industrial applications.

Definitions

The term "cellulase", as used herein, refers to the group of enzymes responsible for the hydrolisation of cellulose into monosaccharides or shorter polysaccharides and oligosaccharides. There are three main types of cellulases: (i) endocellulases, which cleave internal (1-4)-β-D-glucosidic linkages; (ii) exocellulases, which break (1-4)-β-D-glucosidic linkages releasing cellobiose or cellotetrose from the non-reducing ends of the chains; and (iii) β-glucosidase, which hydrolyse the remaining glycosidic links into individual monosaccharides.

The term "endocellulase", as used herein, refers to a type of cellulase that randomly cleaves (1-4)-β-D-glucosidic links in cellulose, lichenin and cereal β-D-glucans, thereby creating new chain ends. Endocellulases also hydrolyse 1,4-linkages in β-D-glucans also containing 1,3-linkages. It has been classified by the Nomenclature Committee of the International Union of Biochemistry and Molecular Biology as EC 3.2.1.4. Endocellulases derived from bacteria have a catalytic domain and a carbohydrate binding module attached by a linker or linking domain.

The term "Endocellulase catalytic domain", as used herein, refers to a domain of an enzyme being responsible of its catalytic function, particularly of its endocellulase function. It contains the active site, a set of amino acids with a special spatial arrangement that permits interaction with the substrate to effect the reaction.

The term "functionally equivalent variant" as used herein is understood to mean all those proteins derived from a sequence by modification, insertion and/or deletion or one or more amino acids, whenever the function is substantially maintained, particularly in the case of a functionally equivalent variant of a catalytic domain refers to maintaining the catalytic activity.

Assays to determine the function of an enzyme are known by the skilled person and include, without limitation, initial rate assays, progress curve assays, transient kinetics assays and relaxation assays. Continuous assays of enzymatic activity include, without limitation, spectrophotometric, fluorometric, calorimetric, chemiluminiscent, light scattering and microscale thermophoresis assays. Discontinuous assays of enzymatic activity include, without limitation, radiometric and chromatographic assays. As the skilled person understands, factors that may influence enzymatic activity comprise salt concentration, temperature, pH, and substrate concentration.

Particularly the endocellulase catalytic activity may be measured by means of a number of techniques assays that are conventional to the skilled person, including the viscosimetric methods using soluble derivatised cellulose, or by employing soluble or insoluble (crosslinked) dyed cellulose or mixed-linkage β-glucan, such as the carboxymethyl cellulose (CMC) assay, and the hydroxyethylcellulose (HEC) assay. In general, assays based on the use of dyed polysaccharides are standardised against a reducing sugar method that employs either CM-cellulose or β-glucan as substrate. In a particular embodiment the CELLG3 assay (particularly K-CellG3, Megazyme International Ireland) may be used for specific endocellulases and measures activity.

The term "endocellulase catalytic activity", as used herein relates to the ability of hydrolysing 1,4-linkages in β-D-glucans also containing 1,3-linkages.

The term "carbohydrate binding domain" or "carbohydrate binding module", as used herein, refers to a protein domain that is present in carbohydrate-active enzymes (for example endocellulases and exocellulases) and having carbohydrate-binding activity. Carbohydrate binding domains contributes to the catalytic efficiency by increasing enzyme-substrate complex formations.

The term "linking domain", as used herein, refers to a sequence between domains. Linkers are often composed of flexible residues like glycine and serine so that the adjacent protein domains are free to move relative to one another. Longer linkers are used when it is necessary to ensure that two adjacent domains do not sterically interfere with one another.

The term "tag", as used herein, refers to any amino acid sequence for which specific binding molecules are available, thus allowing the detection/purification of any polypeptide carrying said tag. The tag is generally placed at the amino- or the carboxyl-terminus of the polypeptide. The presence of such tag allows the adapter molecule to be detected using an antibody against the tag polypeptide. Also, the provision of the tag enables the adapter polypeptide to be readily purified by affinity purification using an anti-tag antibody or another type of affinity reagent that binds to the epitope tag.

The term "nucleic acid", as used herein, relates to a deoxyribonucleotide or ribonucleotide polymer in either single or double stranded form and, unless otherwise limited, encompasses natural nucleotides and analogues of natural nucleotides that hybridize to nucleic acids in a manner similar to naturally occurring nucleotides. The term "nucleotide" includes, but is not limited to, a monomer that includes a base (such as a pyrimidine, purine or synthetic analogs thereof) linked to a sugar (such as ribose, deoxyribose or synthetic analogs thereof), or a base linked to an amino acid, as in a peptide nucleic acid (PNA). A nucleotide is one monomer in an oligonucleotide or in a polynucleotide.

A "nucleotide sequence" or "nucleic acid sequence" refers to the sequence of bases in an oligonucleotide or in a polynucleotide.

The term "signal peptide", as used herein, also known as signal, localization signal, localization sequence, transit peptide, leader sequence or leader peptide refers to a short peptide present at the N-terminus of the majority of newly synthesized proteins that are destined towards the secretory pathway.

The term "host cell", as used herein, refers to a cell into which a nucleic acid of the invention, such as a polynucleotide or a vector according to the invention, has been introduced and is capable of expressing the endonuclease of the invention. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

The term "expression cassette", as used herein relates to a gene construct of the invention operatively linked to an expression control sequence. The gene construct of the invention can be obtained through the use of techniques widely known in the prior art.

The term "vector", as used herein, refers to a nucleic acid sequence comprising the necessary sequences so that after transcribing and translating said sequences in a cell a polypeptide comprising an endocellulase catalytic domain is generated. Said sequence is operably linked to additional segments that provide for its autonomous replication in a host cell of interest. Preferably, the vector is an expression vector, which is defined as a vector, which in addition to the regions of the autonomous replication in a host cell, contains regions operably linked to the nucleic acid of the invention and which are capable of enhancing the expression of the products of the nucleic acid according to the invention. The vectors of the invention can be obtained by means of techniques widely known in the art.

The term "hydrolysing cellulose", as used herein relates to the cleavage of chemical bonds of cellulose.

The term "crystalline cellulose", as used herein, relates to a $(1{\rightarrow}4)$-$\beta$-D-glucan (cellulose) in crystalline form with a structure consisting of several hundred to over ten thousand D-glucose residues joined by $\beta(1{\rightarrow}4)$ glycosidic linkages. The crystalline nature of cellulose implies a structural order in which all of the atoms are fixed in discrete positions with respect to one another. An important feature of the crystalline array is that the component molecules of individual microfibrils are packed sufficiently tightly to prevent penetration not only by enzymes but even by small molecules such as water. A skilled person can identify is the cellulose is arranged in a crystalline form, for example by X-ray diffraction data or cystallography. Usually, crystalline cellulose, or MCC, is defined as cellulose with a crystallinity of at least 78%.

The term "sample containing crystalline cellulose" relates to forest biomass and agricultural biomass containing cellulose. Illustrative non-limitative examples of said samples are lignocellulose biomass (composed mainly of cellulose, hemicellulose and lignin), corn stover, *Panicum virgatum* (switchgrass), *Miscanthus* grass species, wood chips and the byproducts of lawn and tree maintenance. Lignocellulosic biomass can be grouped into four main categories: (1) agricultural residues (including corn stover and sugarcane bagasse), (2) dedicated energy crops, (3) wood residues (including sawmill and paper mill discards), and (4) municipal paper waste. Illustrative lignocellulosic biomass sources include, but are not limited to grasses, rice hulls, bagasse, jute, hemp, flax, bamboo, sisal, abaca, straw, corn cobs, corn stover, alfalfa, hay, coconut hair, seaweed, algae, "Endocellulase-treated cellulose", as used herein relates to a cellulose having new chain ends compared to non-treated cellulose.

"Cellobiose", as used herein relates to a glycosylglucose consisting of two glucose units linked via a $\beta(1{-}4)$ bond produced during a metabolic reaction in plants, the kingdom that include flowering plants, conifers and other gymnosperms.

"Cellotetraose", as used herein relates to a tetrasaccharide comprised of four D-glucose residues connected by $\beta(1{-}4)$ linkages.

"Beta-glucosidase", as used herein relates to a glucosidase enzyme located in on the brush border of the small intestine that acts upon $\beta1{\rightarrow}4$ bonds linking two glucose or glucose-substituted molecules (i.e., the disaccharide cellobiose). It is classified as 3.2.1.21 of the EC number.

"Yeast", as used herein relates to an eukaryotic microorganisms classified as members of the fungus kingdom. Yeasts are unicellular, although some species may also develop multicellular characteristics by forming strings of connected budding cells known as pseudohyphae or false hyphae.

The term "cellulose", as used herein, refers to an organic compound with CAS number 9004-34-6, a polysaccharide consisting of a linear chain of several hundred to many thousands of $\beta(1{-}4)$ linked D-glucose units.

The term "exocellulase", also known as Glucan 1,4-beta-glucosidase (or 4-beta-D-glucan glucohydrolase), exo-1,4-beta-glucosidase, exocellulase, exo-beta-1,4-glucosidase, exo-beta-1,4-glucanase, beta-1,4-beta-glucanase, exo-1,4-beta-glucanase, or 1,4-beta-D-glucan glucohydrolase, as used herein, relates to an enzyme enzyme that catalyses the hydrolysis of $(1{\rightarrow}4)$-linkages in 1,4-beta-D-glucans and related oligosaccharides, removing successive glucose units, that acts at the ends of the polysaccharide chain.

The term "bioethanol", as used herein, relates to ethanol with chemical formula is C2H5OH, however bears the suffix "bio" because it is produced by fermenting biomass an therefore it is a natural product.

The term "distilling", as used herein relates to a method to separate two liquid utilizing their different boiling points, in present case removing of water from bioethanol.

The term "dehydration", as used herein relates to a purification method, a physical absorption process using a molecular sieve, for example, ZEOCHEM Z3-03 (a special 3A molecular sieve for ethanol dehydration).

The term "detergent", as used herein, also known as "surfactant", relates to amphipathic surface-active agents that, when added to a liquid, reduce surface tension of the liquid in comparison to the same liquid in the absence of the detergent. Detergents are also capable of preventing aggregation of proteins and of preventing non-specific interaction or binding of contaminants to a protein of interest.

In the present description the term "comprising" also includes "consisting essentially of" and "consisting of".

Endocellulases, Nucleic Acid, Expression Cassettes, Vector and Host Cells

In a first aspect, the invention relates to a polypeptide comprising an endocellulase catalytic domain, hereinafter referred to as the "polypeptide of the invention", wherein the catalytic domain comprises the sequence of SEQ ID NO: 1 or a functionally equivalent variant thereof that substantially maintains or improves its catalytic activity.

The invention contemplates a polypeptide comprising an endocellulase catalytic domain comprising the sequence of SEQ ID NO: 1.

The present invention also contemplates a polypeptide comprising an endocellulase catalytic domain consisting essentially of or consisting of the sequence SEQ ID NO: 1.

The present invention also contemplates a polypeptides comprising endocellulase catalytic domains comprising, consisting essentially of or consisting of a functionally equivalent variant of the catalytic domain comprising the sequence of SEQ ID NO: 1 that substantially maintains at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the catalytic domain comprising the sequence SEQ ID NO: 1. Furthermore, the present invention contemplates a polypeptides comprising endocellulase catalytic domains comprising, consisting essentially of or consisting of a functionally equivalent variant of the catalytic domain comprising, consisting essentially of or consisting of the sequence of SEQ ID NO: 1 that substantially improves the catalytic activity of the catalytic domain comprising the sequence SEQ ID NO: 1 in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

As it is used herein, the term "functionally equivalent variant" refers to catalytic domains comprising, consisting essentially of or consisting of sequences substantially similar to SEQ ID NO: 1 maintaining or improving its catalytic activity. A functionally equivalent variant of the catalytic domain comprising the sequence SEQ ID NO: 1 can be an amino acid sequence derived from SEQ ID NO: 1 comprising the addition, substitution or modification of one or more amino acid residues. By way of illustration, functionally equivalent variants of the catalytic domain comprising the sequence SEQ ID NO: 1 include sequences comprising the addition of 1 amino acid, 2 amino acids, 3 amino acids, 4 amino acids, 5 amino acids, 10 amino acids, 15 amino acids, 20 amino acids, 25 amino acids, 30 amino acids, 35 amino acids, 40 amino acids, 45 amino acids, 50 amino acids, 60 amino acids, 70 amino acids, 80 amino acids, 90 amino acids, 100 amino acids, 150 amino acids, 200 amino acids, at least 500 amino acids, at least 1000 amino acids or more at the amino terminus of the sequence SEQ ID NO: 1, and/or comprising the addition of 1 amino acid, 2 amino acids, 3 amino acids, 4 amino acids, 5 amino acids, 10 amino acids, 15 amino acids, 20 amino acids, 25 amino acids, 30 amino acids, 35 amino acids, 40 amino acids, 45 amino acids, 50 amino acids, 60 amino acids, 70 amino acids, 80 amino acids, 90 amino acids, 100 amino acids, 150 amino acids, 200 amino acids, at least 500 amino acids, at least 1000 amino acids or more at the carboxy terminus of the sequence SEQ ID NO: 1, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the catalytic domain comprising the sequence SEQ ID NO: 1, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

Functionally equivalent variants of a catalytic domain comprising the sequence SEQ ID NO: 1 also include catalytic domains comprising amino acid sequences with a sequence identity of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 1, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the catalytic domain comprising the sequence SEQ ID NO: 1, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

The terms "identity", "identical" or "percent identity" in the context of two or more amino acid sequences, refer to two or more sequences or subsequences that are the same or have a specified percentage of amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al., 1990, Proc. Natl. Acad. Sci., 87:2264-8, as modified in Karlin et al., 1993, Proc. Natl. Acad. Sci., 90:5873-7, and incorporated into the NBLAST and XBLAST programs (Altschul et al., 1991, Nucleic Acids Res., 25:3389-402). In certain embodiments, Gapped BLAST can be used as described in Altschul et al., 1997, Nucleic Acids Res. 25:3389-402. BLAST-2, WU-BLAST-2 (Altschul et al., 1996, Methods in Enzymology, 266:460-80), ALIGN, ALIGN-2 (Genentech, South San Francisco, Calif.) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (J. Mol. Biol. 48:444-53 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (CABIOS, 4:11-7 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the second sequence is longer than the first sequence, then the percent identity may be determined only in the region of overlap between said first and second sequences. In this case, the same formula as above can be used but using as Z value the length of the region wherein the first and second sequence overlaps, said region having a length which is substantially the same as the length of the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2:482-9 (1981), to find the best segment of homology between two sequences. When using Bestfit or any other sequence alignment program to determine whether a particular sequence is, for instance, 95% identical to a reference sequence according to the present invention, the parameters are set such that the percentage of identity is calculated over the full length of the reference amino acid sequence and that gaps in homology of up to 5% of the total number of nucleotides in the reference sequence are allowed.

In some embodiments, two amino acid sequences are substantially identical, meaning they have at least 70%, at least 75%, at least 80%, at least 85%, at least 90%, and in some embodiments at least 95%, 96%, 97%, 98%, 99% amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared.

In an embodiment, the functionally equivalent variant of the catalytic domain comprising, consisting essentially of or consisting of SEQ ID NO: 1 that substantially maintains or improves its catalytic activity comprises, consists essentially of or consists of a catalytic domain having a sequence selected from the group consisting of SEQ ID NO: 2, SEQ ID NO:3 or SEQ ID NO:69. In a particular embodiment, the catalytic domain comprises, consists essentially of or consists of SEQ ID NO: 2. In another particular embodiment, the catalytic domain comprises, consists essentially of or consists of SEQ ID NO: 3. In another particular embodiment, the catalytic domain comprises, consists essentially of or consists of SEQ ID NO: 69.

In one embodiment, the functionally equivalent variant of the catalytic domain comprising, consisting essentially of or consisting of SEQ ID NO:2 or a catalytic domains comprising an amino acid sequence with a sequence identity with respect to SEQ ID NO:2 of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 1, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the catalytic domain comprising the sequence SEQ ID NO: 1, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

In one embodiment, the functionally equivalent variant of the catalytic domain comprising, consisting essentially of or consisting of SEQ ID NO:3 or a catalytic domains comprising an amino acid sequence with a sequence identity with respect to SEQ ID NO:3 of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 1, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the catalytic domain comprising the sequence SEQ ID NO: 1, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

In one embodiment, the functionally equivalent variant of the catalytic domain comprising, consisting essentially of or consisting of SEQ ID NO:69 or a catalytic domains comprising an amino acid sequence with a sequence identity with respect to SEQ ID NO:69 of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 1, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the catalytic activity of the catalytic domain comprising the sequence SEQ ID NO: 1, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

In one embodiment, the catalytic domain is not the catalytic domain of an endocellulase selected from the group consisting of:

The endocellulase shown in the UniProt database with Accession No. A0A0B2T1H3,

The endocellulase shown in the UniProt database with Accession No. U3RD83,

The endocellulase shown in the EMBL database with Accession No. KF240855,

The endocellulase shown in the UniProt database with Accession No. U3R8L0,

The endocellulase shown in the EMBL database with Accession KF240853

The endocellulase shown in the GenSeq database with accession number BCD39860.

The endocellulase shown in international publication WO2008005529 under SEQ ID NO:60, The endocellulase shown in international publication WO2008005529 under SEQ ID NO:59, The plant biomass degrading enzyme #67 shown in international publication WO2009208941, The endocellulase shown in international publication WO2011109905 under SEQ ID NO:15, The endocellulase shown in the UniProt database with Accession No. A0B0B2T1H3, The endocellulase shown in the UniProt database with Accession No. F4FAV2, The endocellulase shown in the UniProt database with Accession No. A0A0D0X703

The endocellulase shown in the UniProt database with Accession No P26224.

The term "catalytic activity" or "enzyme activity", as used herein, refers to the ability of an enzyme to accelerate or catalyse chemical reactions. The catalytic activity is a measure of the quantity of active enzyme present and is thus dependent on reaction conditions, including temperature and/or pH, which should be specified. The commonly used unit is enzyme unit (U)=1 μmol min$^{-1}$. Another common unit is the specific activity of an enzyme, which is the activity of an enzyme per milligram of total protein (expressed in pmol min$^{-1}$ mg$^{-1}$) and measures enzyme purity in the mixture.

The catalytic activity is characterised by means of the following kinetic parameters: $V_{max}$, which is the maximum speed of an enzymatic reaction; the Michaelis-Menten constant ($K_m$), which is the substrate concentration required for an enzyme to reach one-half its maximum reaction rate; and $k_{cat}$, or turnover number, which is the number of substrate molecules handled by one active site per second. These kinetic parameters depend on solution conditions, such as temperature and pH, and on substrate concentration. The efficiency of an enzyme can be expressed in terms of $k_{cat}/K_m$, or specificity constant. Because the specificity constant reflects both affinity and catalytic ability, it is useful for comparing different enzymes against each other, or the same enzyme with different substrates.

The term "catalytic activity of the endocellulase catalytic domain", as used herein, refers to the ability of the catalytic domain to cleave or hydrolyse (1-4)-β-D-glucosidic links in cellulose, including crystalline cellulose. The catalytic activity of the endocellulase catalytic domain may be measured by means of a number of techniques assays that are conventional to the skilled person, including the viscosimetric methods using soluble derivatised cellulose, or by employing soluble or insoluble (crosslinked) dyed cellulose or mixed-linkage β-glucan, such as the carboxymethyl cellulose (CMC) assay, and the hydroxyethylcellulose (HEC) assay. In general, assays based on the use of dyed polysaccharides are standardised against a reducing sugar method that employs either CM-cellulose or β-glucan as substrate. In a particular embodiment, the CMC assay is used.

As with other enzymes, the catalytic activity of the catalytic domain of endocellulase depends on a number of reaction parameters, including temperature and pH. Thus, in one embodiment, the functionally equivalent variant of a catalytic domain comprising, consisting essentially of or consisting of the sequence SEQ ID NO: 1 maintains or improves its catalytic activity at a temperature of at least 0° C., at least 5° C., at least 10° C., at least 15° C., at least 20° C., at least 25° C., at least 30° C., at least 35° C., at least 37° C., at least 40° C., at least 45° C., at least 50° C., at least 55° C., at least 60° C., at least 65° C., at least 70° C., at least 75° C., at least 80° C., at least 85° C., at least 90° C., at least 95° C., at least 100° C., or higher. Likewise, in another embodiment the functionally equivalent variant of a catalytic domain comprising, consisting essentially of or consisting of the sequence SEQ ID NO: 1 maintains or improves its catalytic activity at pH 0, or at least pH 0.1, or at least pH 0.5, or at least pH 1.0, or at least pH 1.5, or at least pH 2.0, or at least pH 2.5, or at least pH 3.0, or at least pH 3.5, or at least pH 4.0, or at least pH 4.5, or at least pH 5.0, or at least pH 5.5, or at least pH 6.0, or at least pH 6.5, or at least pH 7.0, or at least pH 7.5, or at least pH 8.0, or at least pH 8.5, or at least pH 9.0, or at least pH 9.5, or at least pH 10.0, or at least pH 10.5, or at least pH 11.0, or at least pH 11.5, or at least pH 12.0, or at least pH 12.5, or at least pH 13.0, or at least pH 13.5, or pH 14. All possible combinations of temperatures and pH are also contemplated by the invention.

In another aspect, the endocellulase catalytic domain of the invention is combined with any carbohydrate binding domain (CBM) of any enzyme capable of binding to carbohydrates containing such domain, provided that they have cellulose-binding activity. Therefore, in another aspect, the invention relates to a polypeptide comprising the endocellulase catalytic domain according to the invention further comprising a carbohydrate binding domain.

In a preferred embodiment, the CBM comprises, consists essentially or consists of a sequence selected from the group consisting of SEQ ID NO: 8 to 37.

In a particular embodiment, the carbohydrate binding domain comprises, consists essentially or consists of SEQ ID NO: 4 or a functionally equivalent variant thereof. In another particular embodiment, the carbohydrate binding domain consists of the sequence of SEQ ID NO: 4.

The particulars of a functionally equivalent variant in terms of sequence identity previously described in the context of the catalytic domain also apply to the carbohydrate binding domain, with the necessary amendments, as will be immediate for the person skilled in the art.

Thus, functionally equivalent variants of a carbohydrate binding domain comprising, consisting essentially of or consisting of the sequence SEQ ID NO: 4 also include carbohydrate binding domains comprising, consisting essentially of or consisting of amino acid sequences with a sequence identity of at least 70%, at least 75%, at least 80%, at least 85%, at least 90%, at least 91%, at least 92%, at least 93%, at least 94%, at least 95%, at least 96%, at least 97%, at least 98%, or at least 99% with the sequences SEQ ID NO: 4, and maintaining at least 50%, at least 60%, at least 70%, at least 75%, at least 80%, at least 85%, at least 90%, at least 91%, at least 92%, at least 93%, at least 94%, at least 95%, at least 96%, at least 97%, at least 98%, at least 99%, or at least 100% of the carbohydrate binding activity of the carbohydrate binding domain comprising the sequence SEQ ID NO: 4, or improving it in at least 1%, at least 2%, at least 3%, at least 4%, at least 5%, at least 6%, at least 7%, at least 8%, at least 9%, at least 10%, at least 15%, at least 20%, at least 25%, at least 30%, at least 35%, at least 40%, at least 45%, at least 50%, at least 55%, at least 60%, or at least 65%, at least 70%, at least 75%, at least 80%, at least 85%, at least 90%, at least 95%, at least 100%, at least 150%, at least 200%, at least 300%, at least 400%, at least 500%, at least 1000%, or more.

The activity of a carbohydrate binding domain may be measured as the affinity of said domain for cellulose, for example using biotinylated glycan binding assay or enzyme-linked assay (Kim et al., Biotechnology and bioprocess engineering 19: 575-580 (2013).

The catalytic domain and the carbohydrate binding domain may be joined through a linking domain.

Thus, in another aspect, the invention relates to a polypeptide according to the invention wherein the endocellulase catalytic domain and the carbohydrate linking domain are connected by a linking domain. In a preferred embodiment the linking domain comprises the sequence of SEQ ID NO: 5 or a functionally equivalent variant thereof, said linking domain being located between the catalytic domain and the carbohydrate binding domain. In another preferred embodiment the linking domain comprises the sequence of SEQ ID NO: 68 or a functionally equivalent variant thereof, said linking domain being located between the catalytic domain and the carbohydrate binding domain The linker is usually combined with the carbohydrate-binding domain to form a moiety which comprises, consists or essentially consists of a sequence selected from the group consisting of SEQ ID NO: 38 to 67. It will be appreciated that the sequences of the suitable linking domains correspond to the fragments of the sequences of SEQ ID NO:38 to 67 which results from the deletion from said sequences of the CBM sequences defined SEQ ID NO: 8 to 37.

In another embodiment, the linking domain comprises, consists essentially or consists of the sequence of SEQ ID NO: 5 or a functionally equivalent variant thereof, said linking domain being located between the catalytic domain and the carbohydrate binding domain. In another embodiment, the linking domain comprises, consists essentially or consists of the sequence of SEQ ID NO: 68 or a functionally equivalent variant thereof, said linking domain being located between the catalytic domain and the carbohydrate binding domain.

The particulars of a functionally equivalent variant previously described in the context of the catalytic domain also apply to the linking domain, with the necessary amendments, as will be immediate for the person skilled in the art.

The invention contemplates endocellulase polypeptides, comprising, consisting essentially of or consisting of, from N- to C-terminus, the catalytic domain, the linking domain and the carbohydrate binding domain, as well as endocellulases containing, from amino- to carboxyl-termini, the carbohydrate binding domain, the linking domain and the catalytic domain.

In another particular embodiment, the endocellulase of the invention comprises, consists essentially of or consists of the sequences of SEQ ID NO: 6 or 7.

In another particular embodiment, the endocellulase of the invention does not comprise, consist essentially of or consist of an endocellulase selected from:

The endocellulase shown in the UniProt database with Accession No. A0A0B2T1H3,

The endocellulase shown in the UniProt database with Accession No. U3RD83,

The endocellulase shown in the EMBL database with Accession No. KF240855,

The endocellulase shown in the UniProt database with Accession No. U3R8L0,

The endocellulase shown in the EMBL database with Accession KF240853

The endocellulase shown in the GenSeq database with accession number BCD39860.

The endocellulase shown in international publication WO2008005529 under SEQ ID NO:60, The endocellulase shown in international publication WO2008005529 under SEQ ID NO:59, The plant biomass degrading enzyme #67 shown in international publication WO2009208941, The endocellulase shown in international publication WO2011109905 under SEQ ID NO:15, The endocellulase shown in the UniProt database with Accession No. A0B0B2T1H3, The endocellulase shown in the UniProt database with Accession No. F4FAV2, The endocellulase shown in the UniProt database with Accession No. A0A0D0X703

The endocellulase shown in the UniProt database with Accession No P26224.

In another embodiment, the polypeptide of the invention further comprises a tag suitable for detection and/or purification located at the N-terminus or at the C-terminus.

The protein can be purified from the medium or from the cell lysate by means of affinity to commercial molecules showing a high affinity for said tags.

Suitable detection/purification tags include hexa-histidines (metal chelate moiety), affinity for hexa-hat GST (glutathione S-transferase) glutathione, calmodulin-binding peptide (CBP), streptomycin tag, cellulose-binding domain, maltose-binding protein, S-peptide tag, chitin-binding tag, immunoreactive epitopes, epitope tags, E2tag, HA epitope tag, Myc epitope, FLAG epitope, AU1 and AU5 epitopes, Glu-Glu epitope, KT3 epitope, IRS epitope, Btag epitope, protein kinase-C epitope, VSV epitope or any other tag provided that the tag does not affect the stability of the protein. In a preferred embodiment, the tag is hexa-histidine.

Additional tag polypeptides and their respective antibodies are well known in the art. Illustrative, non-limitative examples are poly-histidine-glycine (poly-his-gly) tags; the flu HA tag polypeptide and its antibody 12CA5; the c-myc tag and the 8F9, 3C7, 6E10, G4, B7 and 9E10 antibodies; the Herpes Simplex virus glycoprotein D (gD) tag and its antibody. Other tag polypeptides include tubulin epitope peptide; and the T7 gene 10 protein peptide tag.

In another aspect, the invention relates to a nucleic acid encoding a polypeptide according to the invention.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

In a preferred embodiment, the nucleic acid further comprises a sequence encoding a signal peptide in frame at the 5"terminus.

"In frame" or operatively linked as used herein means that the nucleic acid of the invention and the signal peptide are expressed in the correct reading frame under control of the expression control or regulating sequences.

Thus, in another aspect, the invention relate to an expression cassette comprising the nucleic acid of the invention, wherein said nucleic acid is under control of a suitable transcriptional and/or translational system.

Control sequences are sequences that control and regulate transcription and, where appropriate, the translation of said nucleic acid, and include promoter sequences, transcriptional regulators encoding sequences, ribosome binding sequences (RBS) and/or transcription terminating sequences. The expression cassette of the present invention may additionally include an enhancer, which may be adjacent to or distant from the promoter sequence and can function to increase transcription from the same. In a particular embodiment, said expression control sequence is functional in prokaryotic cells and organisms, such as bacteria, etc. Whereas in another particular embodiment, said expression control sequence is functional in eukaryotic cells and organisms, for example, insect cells, plant cells, mammalian cells, etc.

Those promoters most commonly used in recombinant DNA construction include the β-lactamase (penicillinase) and lactose promoter systems and a tryptophan (trp) promoter system. While these are the most commonly used, other microbial promoters have been discovered and utilized, and details concerning their nucleotide sequences have been published, enabling a skilled worker to ligate them functionally with vectors. Certain genes from prokaryotes may be expressed efficiently in E. coli from their own promoter sequences, precluding the need for addition of another promoter by artificial means.

In addition to prokaryotes, eukaryotic microbes, such as yeast may also be used. Saccharomyces cerevisiae or common baker's yeast is the most commonly used among eukaryotic microorganisms, although a number of other strains are commonly available. Suitable promoter sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression vectors, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase-2, isocytochrome C, acid phosphatase, degradative enzymes associated with nitrogen metabolism, and the aforementioned glyceraldehyde-3-phosphate dehydrogenase, and enzymes responsible for maltose and galactose utilization. Additionally, the expression cassette of the invention further comprises a marker or gene encoding a motif or phenotype which allows selecting the transformed host cell with said expression cassette. Illustrative examples of said markers that could be present in the expression cassette of the invention include antibiotic resistance genes, genes for resistance to toxic compounds, and in general, all those that allow selecting the genetically transformed cells.

In another aspect, the invention relates to a vector comprising the nucleic acid of the invention or the expression cassette of the invention.

In general, vector containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a vector derived from an E. coli species. The pBR322 plasmid contains genes for ampicillin and tetracycline resistance and thus provides easy means for identifying transformed cells. The pBR322 plasmid, or other microbial plasmid or phage must also contain, or be modified to contain, promoters which can be used by the microorganism for expression.

Any vector containing a host-compatible promoter, origin of replication and termination sequences is suitable.

In the event that the promoter is provided by the vector, the nucleic acid or the expression cassette of the invention must be operatively linked to the vector to permit the promoter sequence to direct RNA polymerase binding and expression of the nucleic acid. Normally, such vectors contain one or more convenient restriction sites for insertion of the desired DNA segment and promoter sequences. Optionally, such vectors contain a selectable marker specific for use in prokaryotic or eukaryotic cells Thus, the expression of the nucleic acid of the invention upon suitable transfection and expression in a host cell, provides the polypeptide of the invention.

A person skilled in the art will understand that there is no limitation as regards the type of vector which can be used because said vector can be a cloning vector suitable for propagation and for obtaining the polynucleotides or suitable gene constructs or expression vectors in different heterologous organisms suitable for purifying the conjugates. Thus, suitable vectors according to the present invention include prokaryotic expression vectors (e.g. pUC18, pUC19, Bluescript and their derivatives), mp18, mp19, pBR322, pMB9, ColEI, pCRI, RP4, phages and shuttle vectors (e.g. pSA3 and pAT28), yeast expression vectors (e.g. vectors of the type of 2 micron vectors), integration vectors, YEP vectors, centromeric vectors and the like, insect cell expression vectors (e.g. the pAC series and pVL series vectors), plant expression vectors, such as vectors of expression in plants (e.g. pIBI, pEarleyGate, pAVA, pCAMBIA, pGSA, pGWB, pMDC, pMY, pORE series vectors), and eukaryotic expression vectors based on viral vectors (e.g. adenoviruses, viruses associated to adenoviruses as well as retroviruses and lentiviruses), as well as non-viral vectors (e.g. pSilencer 4.1-CMV (Ambion®, Life Technologies Corp., Carlsbad, Calif., US), pcDNA3, pcDNA3.1/hyg pHCMV/Zeo, pCR3.1, pEFI/His, pIND/GS, pRc/HCMV2, pSV40/Zeo2, pTRACER-HCMV, pUB6/V5-His, pVAXI, pZeoSV2, pCI, pSVL and pKSV-10, pBPV-1, pML2d and pTDTI).

Vectors may further contain one or more selectable marker sequences suitable for use in the identification of cells which have or have not been transformed or transfected with the vector. Markers include, for example, genes encoding proteins which increase or decrease either resistance or sensitivity to antibiotics or other compounds (e.g. hyg encoding hygromycin resistance), genes which encode enzymes whose activities are detectable by standard assays known in the art (e.g. β-galactosidase or luciferase), and genes which visibly affect the phenotype of transformed or transfected cells, hosts, colonies or plaques such as various fluorescent proteins (e.g. green fluorescent protein, GFP). Alternatively, the vectors of the present invention may carry a non-antibiotic selection marker, including, for instance, genes encoding a catabolic enzyme which enables the growth in medium containing a substrate of said catabolic enzyme as a carbon source. An example of such a catabolic enzyme includes, but is not restricted to, lacYZ encoding lactose uptake and beta-galactosidase. Other selection markers that provide a metabolic advantage in defined media include, but are not restricted to, galTK for galactose utilization, sacPA for sucrose utilization, trePAR for trehalose utilization and xylAB for xylose utilization. Alternatively, the selection can involve the use of antisense mRNA to inhibit a toxic allele, for instance the sacB allele.

In another preferred embodiment the invention relates to host cell comprising the nucleic acid according to the invention or the expression cassette according to the invention or the vector according to the invention.

Host cells suitable for the expression of the nucleic acid, expression cassette or vector of the invention include, without being limited thereto, cells from bacteria, fungi, plants, insects and mammal. Bacterial cells include, without being limited thereto, cells from Gram-positive bacteria, such as species from the genera *Bacillus, Streptomyces and Staphylococcus*, and cells from Gram-negative bacteria, such as cells from the genera *Escherichia* and *Pseudomonas*. Fungi cells preferably include cells from yeasts such as *Saccharomyces, Pichia pastoris* and *Hansenula polymorpha*. Insect cells include, without limitation, *Drosophila* cells and Sf9 cells. Plant cells include, amongst others, cells from cultivated plants, such as cereals, medicinal plants, ornamental plants or bulbs. Mammalian cells suitable for this invention include epithelial cell lines (porcine, etc.), osteosarcoma cell lines (human, etc.), neuroblastoma cell lines (human, etc.), epithelial carcinomas (human, etc.), glial cells (murine, etc.), hepatic cell lines (from monkeys, etc.), CHO (Chinese Hamster Ovary) cells, COS cells, BHK cells, HeLa, 911, AT1080, A549, 293 or PER.C6 cells, human NTERA-2 ECC cells, D3 cells from the mESC line, human embryonary stem cells, such as HS293 and BGV01, SHEF1, SHEF2 and HS181, NIH3T3, 293T, REH and MCF-7 cells, and hMSC cells.

In a preferred embodiment the host cell is a bacterium, more preferably *E. coli*.

Method for Hydrolysing Cellulose

In another aspect, the invention relates to a method for hydrolysing cellulose comprising contacting a sample containing cellulose with a polypeptide according to the invention under suitable conditions for hydrolysing cellulose.

In a preferred embodiment, the sample comprises crystalline cellulose.

The skilled person knows the conditions suitable for hydrolysing cellulose. In a preferred embodiment, the sample containing cellulose is chopped into smaller pieces to accelerate the process of enzymatic hydrolysis. As a way of illustrative non-limitative example, the polypeptide according to the invention is combined with a sample containing cellulose to form a suspension. The sample containing cellulose-polypeptide suspension is maintained, for example, at a pH of from 4 to 5 and the temperature is maintained within the range of from 25 to 80° C., preferably at least 50° C., at least 60° C., at least 70° C. or at least 80° C. during hydrolysis.

It is known that the ratio of substrate to enzyme has a significant effect on the reaction rate. Dense suspensions of finely ground cellulose, wherein the solids contents of the substrate in the cellulose suspension comprise 10% to 30% are found to be highly reactive in a system in which the suspension is vigorously agitated in the presence of a highly concentrated (1-2 mg protein/ml) enzyme culture filtrate solution. It is desirable, however, in such a system, to remove the sugar products being formed from the suspension to prevent product inhibition. Such a system works most efficiently if the sugar products being formed are continuously removed.

In certain embodiments the polypeptide according to the invention find utility in compositions for degrading wood pulp into sugars (e.g., for bio-ethanol production), and/or in feed compositions.

For example, the rate of hydrolysis of cellulosic products may be increased by using a transformant expressing one or more copies of the enzymes having greater cellulolytic activity described herein. This permits degradation of products that contain cellulose or heteroglycans at a faster rate and to a greater extent. Products made from cellulose such as paper, cotton, cellulosic diapers and the like can be degraded more efficiently in a landfill. Thus, the product obtainable from the transformants or the transformants alone may be used in compositions to help degrade by liquefaction a variety of cellulose products that add to the overcrowded landfills.

Separate saccharification and fermentation is a process whereby cellulose present in biomass, e.g., corn stover, is converted to glucose and subsequently yeast strains convert glucose into ethanol. Simultaneous saccharification and fermentation is a process whereby cellulose present in biomass, e.g., corn stover, is converted to glucose and, at the same time and in the same reactor, yeast strains convert glucose into ethanol. Thus, in another approach, the polypeptide according to the invention finds utility in the degradation of biomass to ethanol. Ethanol production from readily available sources of cellulose provides a stable, renewable fuel source.

Cellulose-based feedstocks are comprised of agricultural wastes, grasses and woods and other low-value biomass such as municipal waste (e.g., recycled paper, yard clippings, etc.). Ethanol may be produced from the fermentation of any of these cellulosic feedstocks. However, the cellulose must first be converted to sugars before there can be conversion to ethanol. A large variety of feedstocks may be used with the endocellulase according to the invention, and the one selected for use may depend on the region where the conversion is being done. For example, in the Midwestern United States agricultural wastes such as wheat straw, corn stover and bagasse may predominate while in California rice straw may predominate. However, it should be understood that any available cellulosic biomass may be used in any region.

Thus, the polypeptide according to the invention finds use in the hydrolysis of cellulose to its sugar components. In one embodiment, a variant enzyme is added to the biomass prior to the addition of a fermentative organism. In a second embodiment, a variant enzyme is added to the biomass at the same time as a fermentative organism. Optionally, there may be other cellulase components present in either embodiment.

In certain embodiments the polypeptide of the invention is displayed on a particle (or other surface), or on a microorganism (e.g., on a yeast or other fungus, or bacteria).

In certain embodiments the polypeptide of the invention is provided as a component of a cellulosome or minicellulosome displayed on a particle or a microorganism (e.g., on a yeast or other fungus, or bacteria).

Where the enzyme(s), cellulosome, and/or minicellulosome is presented on a microorganism, the microorganism can be dormant or inactive and in which case the enzyme, cellulosome, and/or minicellulosome simply acts as an enzyme or enzyme complex facilitating the degradation of cellulosic materials to produce sugars.

In certain embodiments the microorganism is active and the enzyme, cellulosome, and/or minicellulosome is displayed and contacted to the cellulosic material in a culture system (e.g., in a consolidated bioreactor).

In another embodiment the cellulosic feedstock can be pretreated. Pretreatment may be by elevated temperature and the addition of either of dilute acid, concentrated acid or dilute alkali solution. In certain embodiments the pretreatment solution can be added for a time sufficient to at least partially hydrolyze the hemicellulose components and then neutralized.

In a typical biomass conversion process, enzymatic saccharification can produce sugars that are made available for biological or chemical conversions to other intermediates or end-products. Therefore, the sugars generated from biomass find use in a variety of processes in addition to the generation of ethanol. Non-limiting examples of such conversions are fermentation of glucose to ethanol, and other biological conversions of glucose to 2,5-diketo-D-gluconate (see, e.g. U.S. Pat. No. 6,599,722), lactic acid, succinate, 1,3-propanediol, 2,3-butanediol, the chemical and biological conversions of xylose to xylitol (see, e.g., WO 1998/021339), and the like.

In one embodiment, the cellulose to be hydrolyzed is contained in a lignocellulosic material.

The term "lignocellulosic material", as used herein, refers to a material, usually derived from plant biomass, which comprises cellulose, hemicellulose and lignin. The lignocellulosic material can be derived from a single material or a combination of materials and/or can be non-modified and/or modified. Lignocellulosic material can be transgenic (i.e., genetically modified). Lignocellulose is generally found, for example, in the fibers, pulp, stems, leaves, hulls, canes, husks, and/or cobs of plants or fibers, leaves, branches, bark, and/or wood of trees and/or bushes. Examples of lignocellulosic materials include, but are not limited to, agricultural biomass, e.g., farming and/or forestry material and/or residues, branches, bushes, canes, forests, grains, grasses, short rotation woody crops, herbaceous crops, and/or leaves; oil palm fibre waste such as empty fruit bunch and palm trunk; energy crops, e.g., corn, millet, and/or soybeans; energy crop residues; paper mill residues; sawmill residues; municipal paper waste; orchard prunings; Willow coppice and Mallee coppice; wood waste; wood chip, logging waste; forest thinning; short-rotation woody crops; bagasse, such as sugar cane bagasse and/or sorghum bagasse, duckweed; wheat straw; oat straw; rice straw; barley straw; rye straw; flax straw; soy hulls; rice hulls; rice straw; tobacco; corn gluten feed; oat hulls; corn kernel; fiber from kernels; corn stover; corn stalks; corn cobs; corn husks; canola; *miscanthus*; energy cane; prairie grass; gamagrass; foxtail; sugar beet pulp; citrus fruit pulp; seed hulls; lawn clippings; cotton; seaweed; trees; shrubs; wheat; wheat straw; products and/or by-products from wet or dry milling of grains; yard waste; plant and/or tree waste products; herbaceous material and/or crops; forests; fruits; flowers; needles; logs; roots; saplings; shrubs; switch grasses; vegetables; fruit peels; vines; wheat midlings; oat hulls; hard and soft woods; or any combination thereof. In another embodiment, the lignocellulosic material may be the product obtained by a processor selected from the group consisting of a dry grind ethanol production facility, a paper pulping facility, a tree harvesting operation, a sugar cane factory, or any combination thereof.

In another embodiment, the hydrolysis of the cellulose in the presence of the polypeptide of the invention is carried out in the presence of a laccase, a xylanase or a hemicellulase.

The term "laccase", as used herein, refers to a benzenediol: oxygen oxidoreductase (E.C. 1.10.3.2) that catalyzes the following reaction:

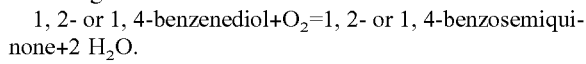

The laccase may be any laccase useful in the processes of the present invention. The laccase may include, but is not limited to, an E.C. 1.10.3.2 laccase. Examples of laccases useful in the present invention include, but are not limited to, laccases from *Chaetomium thermophilum, Coprinus cinereus, Coriolus versicolor, Melanocarpus albomyces, Myceliophthora thermophila, Polyporus pinsitus, Pycnoporus cinnabarinus, Rhizoctonia solani, Scytalidium thermophilum,* and *Streptomyces coelicolor.*

Non-limiting examples of laccases useful in the present invention are laccases from *Chaetomium thermophilum* (GeneSeqP:AEH03373), *Coprinus cinereus* (GeneSeqP: AAW 17973 or AAW 17975), *Coriolus versicolor* (GeneSeqP:ABR57646), *Melanocarpus albomyces* (GeneSeqP: AAU76464), *Myceliophthora thermophila* (GeneSeqP: AAW19855), *Polyporus pinsitus* (GeneSeqP:AAR90721), *Rhizoctonia solani* GeneSeqP:AAW60879 or AAW60925), and *Scytalidium thermophilum* (GeneSeqP:AAW18069 or AAW51783) as well as any variant thereof substantially preserving the laccase activity and having a sequence identity to the mature polypeptide of any of the laccases disclosed herein of at least 60 percent, e.g., at least 65 percent, at least 70 percent, at least 75 percent, at least 80 percent, at least 81 percent, at least 82 percent, at least 83 percent, at least 84 percent, at least 85 percent, at least 86 percent, at least 87 percent, at least 88 percent, at least 89 percent, at least 90 percent, at least 91 percent, at least 92 percent, at least 93 percent, at least 94 percent, at least 95 percent, at least 96 percent, at least 97 percent, at least 98 percent, at least 99 percent, or 100 percent.

Laccase activity can be determined by the oxidation of syringaldazine (4,4'-[azinobis(methanylylidene)]bis(2,6-dimethoxyphenol)) to the corresponding quinone 4,4'-[azobis (methanylylidene])bis(2,6-dimethoxycyclohexa-2,5-dien-1-one) by laccase. The reaction shown below is detected by an increase in absorbance at 530 nm.

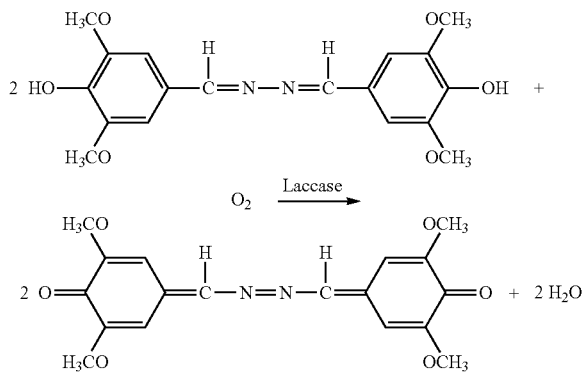

The reaction is conducted in 23 mM MES pH 5.5 at 30 degrees centigrade with 19 μM substrate (syringaldazine) and 1 g/L polyethylene glycol (PEG) 6000. The sample is placed in a spectrophotometer and the change in absorbance is measured at 530 nm every 15 seconds up to 90 seconds. One laccase unit is the amount of enzyme that catalyzes the conversion of 1 μmol syringaldazine per minute under the specified analytical conditions.

The term hemicellulose, as used herein, refers to one or more (e.g., several) enzymes that hydrolyze a hemicellulosic material. Examples of hemicellulases include, but are not limited to, an acetylmannan esterase, an acetylxylan esterase, an arabinanase, an arabinofuranosidase, a coumaric acid esterase, a feruloyl esterase, a galactosidase, a glucuronidase, a glucuronoyl esterase, a mannanase, a mannosidase, a xylanase, and a xylosidase. The substrates for these enzymes, hemicelluloses, are a heterogeneous group of branched and linear polysaccharides that are bound via hydrogen bonds to the cellulose microfibrils in the plant cell wall, crosslinking them into a robust network. Hemicelluloses are also covalently attached to lignin, forming together with cellulose a highly complex structure. The variable structure and organization of hemicelluloses require the concerted action of many enzymes for its complete degradation. The catalytic modules of hemicellulases are either glycoside hydrolases (GHs) that hydrolyze glycosidic bonds, or carbohydrate esterases (CEs), which hydrolyze ester linkages of acetate or ferulic acid side groups. These catalytic modules, based on homology of their primary sequence, can be assigned into GH and CE families. Some families, with an overall similar fold, can be further grouped into clans, marked alphabetically (e.g., GH-A). A most informative and updated classification of these and other carbohydrate active enzymes is available in the Carbohydrate-Active Enzymes (CAZy) database. Hemicellulolytic enzyme activities can be measured according to Ghose and Bisaria, 1987, Pure and Appl. Chem. 59: 1739-1752 at a suitable temperature and a suitable pH.

The term "xylanase", as used herein, refers to a 1,4-beta-D-xylan-xylohydrolase (E.C. 3.2.1.8) that catalyzes the endohydrolysis of 1,4-beta-D-xylosidic linkages in xylans.

Xylanase activity can be determined with 0.2% AZCL-arabinoxylan as substrate in 0.01 percent TRITON(R) X-100 and 200 mM sodium phosphate pH 6 at 37° C. One unit of xylanase activity is defined as 1.0 µmol of azurine produced per minute at 37° C., pH 6 from 0.2% AZCL-arabinoxylan as substrate in 200 mM sodium phosphate pH 6.

Xylanases (e.g. endo-beta-xylanases (E.C. 3.2.1.8), which hydrolyze the xylan backbone chain, can be from bacterial sources (e.g., *Bacillus, Streptomyces, Clostridium, Acidothermus, Microtetrapsora* or *Thermonospora*) or from fungal sources (*Aspergillus, Trichoderma, Neurospora, Humicola, Penicillium* or *Fusarium* (See, e.g., EP473 545; U.S. Pat. No. 5,612,055; WO 92/06209; and WO 97/20920)). Xylanases useful in the invention include commercial preparations (e.g., MULTIFECT(R) and FEEDTREAT(R) Y5 (Danisco Genencor), RONOZYME(R) WX (Novozymes A/S) Pulpzyme(R) HC (Novozymes A/S) and NATUGRAIN WHEAT(R) (BASF). In some embodiments the xylanase is from *Trichoderma reesei* or a variant xylanase from *Trichoderma reesei*, or the inherently thermostable xylanase described in EP1222256B1, as well as other xylanases from *Aspergillus niger, Aspergillus kawachii, Aspergillus tubigensis, Bacillus circulans, Bacillus pumilus, Bacillus subtilis, Neocallimastix patriciarum, Penicillium species, Streptomyces lividans, Streptomyces thermoviolaceus, Thermomonospora fusca, Trichoderma harzianum, Trichoderma reesei*, and *Trichoderma viridae*.

All the terms and embodiments previously described are equally applicable to this aspect of the invention.

Method for Producing Bioethanol

In another aspect, the invention relates to a method for producing bioethanol comprising
(i) contacting a sample containing cellulose with a polypeptide according to the invention under suitable conditions for hydrolysing cellulose, thereby obtaining endocellulase-treated cellulose,
(ii) converting the endocellulase-treated cellulose obtained in step (i) to cellobiose and/or cellotetraose using an exocellulase,
(iii) converting the cellobiose and/or cellotetraose obtained in step (ii) to glucose using a β-glucosidase, and
(iv) converting the glucose obtained in step (iii) to bioethanol in the presence of a yeast capable of producing bioethanol by fermentation of glucose.

The method for producing bioethanol of the invention, comprises a first step of contacting a sample containing cellulose with a polypeptide of the invention under suitable conditions for hydrolysing cellulose, thereby obtaining endocellulase-treated cellulose. In a preferred embodiment the sample containing cellulose, contains crystalline cellulose. In another preferred embodiment, the sample containing crystalline cellulose is chopped into smaller pieces to accelerate the process of enzymatic hydrolysis. As a way of illustrative non-limitative example step (i) can be carried out by a method previously described.

In certain embodiments the polypeptide according to the invention is displayed on a particle (or other surface), or on a microorganism (e.g., on a yeast or other fungus, or bacteria).

In certain embodiments the polypeptide according to the invention is provided as a component of a cellulosome or minicellulosome displayed on a particle or a microorganism (e.g., on a yeast or other fungus, or bacteria).

Where the enzyme(s), cellulosome, and/or minicellulosome is presented on a microorganism, the microorganism can be dormant or inactive and in which case the enzyme, cellulosome, and/or minicellulosome simply acts as an enzyme or enzyme complex facilitating the degradation of cellulosic materials to produce sugars.

In another embodiment, the hydrolysis of cellulose in step (i) in the presence of the polypeptide of the invention is carried out in the presence of a laccase, a xylanase or a hemicellulase. In another embodiment, the sample containing cellulose to be hydrolyzed is contained in a lignocellulosic material.

Step (ii) comprises converting the endocellulase-treated cellulose obtained in step (i) to cellobiose and/or cellotetraose using an exocellulase. Any exocellulase can be used in step (ii) of the method for producing bioethanol according to the invention. Examples of exocellulases include cellobiohydrolases, which in turn includes those that cleave the 1,4-beta-D-glycosidic linkages from the reducing ends of the cellulose chain and those that cleaves the same linkages from the non-reducing ends. Suitable exocellulases for use according to the present invention include, without limitation, the *A. cellulolyticus* E1 exocellulase, the *Thermobifida fusca* Cel6B and Cel48A exocellulases, the *Trichoderma harzianum* FP108 CBH1 exocellulase, the *Thermomonospora fusca* E3, E4 and E6 exolcellulases and the *Trichoderma reesei* Cel7A, CBH I and CBH II exocellulases.

Step (iii) comprises converting the cellobiose and/or cellotetraose obtained in step (ii) to glucose using a β-glucosidase. Any exocellulase can be used in step (iii) of the invention. The β-glucosidases for used in the method according to the present invention can be obtained, or produced recombinantly, from, inter alia, *Aspergillus aculeatus, Aspergillus kawachi, Aspergillus oryzae, Cellulomonas biazotea, Penicillium funiculosum, Saccharomycopsis fibuligera, Schizosaccharomyces pombe*. The β-glucosidase can be produced by expressing an endogenous or exogenous gene encoding a β-glucosidase. For example, β-glucosidase can be secreted into the extracellular space e.g., by Gram-positive organisms (e.g., *Bacillus* or *Actinomycetes*), or eukaryotic hosts (e.g., *Trichoderma, Aspergillus, Saccharomyces*, or *Pichia*). The β-glucosidase can be, in some circumstances, overexpressed or under-expressed. The β-glucosidase can also be obtained from commercial sources. Examples of commercial β-glucosidase preparation suitable for use in the present disclosure include, for example, *Trichoderma reesei* β-glucosidase in Accellerase (R) BG (Danisco US Inc., Genencor); NOVOZYM™ 188 (a β-glucosidase from *Aspergillus niger*); *Agrobacterium* sp. β-glucosidase, and *Thermatoga maritima* β-glucosidase from Megazyme (Megazyme International Ireland Ltd., Ireland).

The final step (iv) comprises converting the glucose obtained in step (iii) to bioethanol in the presence of a yeast capable of producing bioethanol by fermentation of glucose. In a preferred embodiment, the glucose obtained in step (iii) is removed from the solution. In another preferred embodiment, the yeast capable of producing bioethanol by fermentation of glucose is *Saccharomyces cerevisiae*.

It is also contemplated in the invention, that the exocellulase and/or β-glucosidase is expressed by the yeast capable of producing bioethanol by fermentation of glucose. As a way of illustrative-non limitative example the *S. cerevisae* transformant carrying the BGL1 (β-glucosidase gene) is capable of fermenting cellobiose to ethanol (Marchida M I et al, 1998 Appl. Environ. Microbiol. 54:3147-3155).

In a particular embodiment, the method for producing bioethanol further comprises a step (v) comprising distilling or dehydrating the bioethanol obtained in step (iv). In a preferred embodiment, the method further comprises distilling the bioethanol from resulting liquid by boiling the water off and collecting the bioethanol in a separate tank. In another preferred embodiment, to distil pure bioethanol, benzene or cyclohexane may be added to the mixture. These chemicals bind to and remove the last small bits of water from the distillate.

In various embodiments ethanol can be produced via saccharification and fermentation processes from cellulosic biomass such as trees, herbaceous plants, municipal solid waste and agricultural and forestry residues. However, the ratio of individual cellulase enzymes within a naturally occurring cellulase mixture produced by a microbe may not be the most efficient for rapid conversion of cellulose in biomass to glucose. It is known that endoglucanases act to produce new cellulose chain ends which themselves are substrates for the action of cellobiohydrolases and thereby improve the efficiency of hydrolysis of the entire cellulase system. Therefore, the use of increased or optimized enzymes as described herein can greatly enhance the production of ethanol.

All the terms and embodiments previously described are equally applicable to this aspect of the invention.

Detergent Compositions

In another aspect, the invention relates to a detergent composition comprising a polypeptide of the invention and a surfactant. In certain embodiments, the detergent compositions that exhibit enhanced cleaning ability, function as a softening agent and/or improve the feel of cotton fabrics (e.g., "stone washing" or "biopolishing").

In certain embodiments the detergent comprises a laundry detergent, a dish detergent, or an industrial detergent. In various embodiments detergent compositions employ besides the variant polypeptides described herein, a surfactant, including anionic, non-ionic and ampholytic surfactants, optionally a hydrolase, building agents, bleaching agents, bluing agents and fluorescent dyes, caking inhibitors, solubilizers, cationic surfactants and the like.

In various embodiments polypeptides described herein can be added to the detergent composition either in a liquid diluent, in granules, in emulsions, in gels, in pastes, and the like. Such forms are well known to the skilled artisan. When a solid detergent composition is employed, the cellulase composition is preferably formulated as granules. Preferably, the granules can be formulated so as to contain a cellulase protecting agent (see, e.g., U.S. Pat. No. 6,162,782).

In various illustrative, but non-limiting embodiments the polypeptide of the invention can be employed from about 0.00005 weight percent to about 5 weight percent relative to the total detergent composition. More typically the polypeptide is employed from about 0.0002 weight percent to about 2 weight percent relative to the total detergent composition.

Uses of the Invention

The variant polypeptides, the polypeptides and the nucleic acid constructs encoding such polypeptides find utility in a wide variety of applications some of which are described below.

In another aspect, the invention relates to the use of a polypeptide of the invention for hydrolysing cellulose (first use of the invention).

According to this use of the invention, it is possible to deconstruct cellulose into fermentable sugars, including glucose and/or oligomers that can be further converted into valuable products through biological or chemical approaches.

The cellulose may be in the form or primarily purified cellulose or with small proportions of other polysaccharides, mainly hemicellulose from higher plants In another aspect the invention relates to the use of the polypeptide of the invention for producing bioethanol (second use of the invention).

In another aspect, the invention relates to the use of the polypeptide of the invention as a detergent (third use of the invention).

All the terms and embodiments previously described are equally applicable to this aspect of the invention.

***

The invention will be described by way of the following examples which are to be considered as merely illustrative and not limitative of the scope of the invention.

EXAMPLES

Materials and Methods
Protein Expression and Purification:

Ancestral (LFCA) and extant *Thermotoga Maritima* endoglucanase proteins encoding genes were synthesized and codon-optimized for expression in *E. coli* cells. They were cloned into pQE80L vector (Qiagen) and transformed onto *E. coli* BL21 (Life Technologies). Incubation of bacteria was performed overnight in LB medium at 37° C., and after reaching O.D of 0.6, 1 mM IPTG was add to induce protein expression. Cell pellets were lysed with French press pressure cell after centrifugation. For the purification, $His_6$-tagged proteins were loaded onto His GraviTrap affinity column (GE Healthcare). Finally, by size exclusion chromatography proteins were further purified using a Superdex 200HR column (GE Healthcare). The buffer used was 50 mM citrate buffer, pH 4.8. For the verification of purified proteins sodium dodecyl sulfate-polyacrylamide gel electrophoresis (SDS-PAGE) was used on 12% acrylamide gels. The protein concentration was estimated by measuring absorbance at 280 nm (Nanodrop 2000C). *T. reesei* (Celluclast, C2730 Sigma Aldrich) concentration was determined by SDS-PAGE electrophoresis in 8% acrylamide gel. For laccase expression, the composition of the culture medium consisted of 10 g glucose, 20 g L$^{-1}$ yeast extract, 0.9 g L$^{-1}$ $(NH_4)_2SO_4$, 2 g $KH_2PO_4$, 0.5 g $MgSO_4 7H_2O$, 0.1 g $CaCl_2 2H_2O$, 0.5 g KCl and 0.5 g thiamine (previously sterilized by filtration) in citrate-phosphate buffer (pH 4.5). The cultures were performed in cotton-plugged Erlenmeyer flasks (250 mL) containing 7.5 mg of pipe shell and 150 mL of culture medium, semi-solid-state fermentation (SSF). Flasks were sterilized before inoculation with the seed shells. Three agar plugs of the *T. pubescens* were used per Erlenmeyer as inoculum.

Enzymatic Activity Assay

Cellulolytic activity of ancestral endocellulase (LFCA) was tested at 50 mM and pH 4.8 citrate buffer with 2% CMC (Sigma), 30 min at various incubation temperatures. Cellulases from *T. maritima* and *T. reesei* (Celluclast, C2730 Sigma Aldrich) were used as controls. Enzymatic reactions were terminated by placing the tubes into an ice-water bath. Enzymatic activity was determined quantitatively by measuring soluble reducing sugars released from the cellulosic substrate by the dinitrosalicylic acid (DNS) method (Analitical Chemistry, 1959, 31, 426-428). A volume of 3 ml of the DNS solution was added to each sample and after boiling the reaction mixture for 5 min, absorbance was measured at 540 nm. A glucose standard curve was used to determine the concentration of the released reducing sugars. All assays were performed in triplicate and average value with standard deviation was determined. For determination of pH dependence, purified enzymes were diluted in 50 mM citrate buffer at different pH values between 4 and 12. Activities were measured with 2% CMC at 70° C. for 30 min. The amount of reducing sugars was measured and quantified by the DNS method[36]. For comparison, cellulases from *T. maritima* and *T. reesei* (Celluclast, C2730 Sigma Aldrich) were used. In addition, endocellulase activity was measured using the CellG3 method of an endo-cellulase assay kit (K-CellG3, Megazyme International Ireland). In this assay, enzyme samples were diluted in acetate buffer (100 mM, pH 4.5) and after the addition of CellG3 substrate enzyme solutions were incubated at different temperatures. Cellulase cleaved a bond within BCIPNPβ-G3, the non-blocked reaction product containing the 2-chloro-4-nitrophenyl substituent was instantly cleaved to D-glucose and free 2-CI-4-nitrophenol (CIPNP). Finally, the hydrolysis reaction was stopped by addition of Trizma base solution (pH 11) and the CI-phenolate colour was developed and measured at 400 nm (NanoDrop 2000C). CellG3 Unit was defined as the amount of enzyme required to release one micromole of 2-chloro-4-nitrophenol from CellG3 in one minute under the defined assay conditions. The enzyme activity was calculated multiplying the measured absorbance at 400 nm by 9.64 and by the dilution factor.

Residual and Long-Term Activity Measurements

The enzymes were diluted in citrate buffer 50 mM at their optimum pH, were incubated at different temperatures (60-90° C.). The residual activity was measured on 2% CMC for 30 min at 60° C. The amount of reducing sugars was measured and quantified by the DNS method. The parameter $T_{50}$ is defined as the temperature at which an enzyme loses 50% of its optimal activity after a 30 min heat treatment. For the long-term activity, all measurements were conducted in 50 mM citrate buffer, pH 4.8 on 2% CMC at 60° C. for a period of 10 to 240 minutes. After hydrolysis, the reducing sugar concentration was measured by the DNS method.

Lignocellulosic (Cardboard) Substrate Hydrolysis

We used 50 mg of cardboard in 50 mM citrate buffer at pH 4.8. Enzyme hydrolysis was performed for 1 hour. Endoglucanase alone or in combination with Laccase and Xylanase were used for hydrolysis of the lignocellulosic material. Three different enzyme combinations were used differing in the endoglucanse used: ancestral, *T. maritima* or *T. reesei*. Cellulose degradation was determined by determining percentage of hydrolysis as described by Van Dyk, J. S. & Pletschke, B. I. (Biotechnol Adv., 2012, 30, 1458-1480).

Example 1: Endocellulase Activity of the Ancestral Endo-β-Ducanase

The endocellulase activity was assayed using three endocellulases, namely the polypeptide of SEQ ID NO:2 and two commercial cellulases for comparison. The commercial cellulases correspond to the bacterial endocellulase from *B. amyloliquefaciens* and the fungal endocellulase from *Trichoderma reesei*. For all three enzymes five independent assays were performed obtaining an average value and standard deviation. In all cases the inventors used an equal concentration of enzyme in the original solution. The test was performed at increasing temperatures. As it can observed in FIG. 1, the ancestral cellulases display a considerably higher activity measured in CellG3 units. In the case of *T. reesei*, the activity is notably lower than the activity of bacterial endocellulases. At temperature above 70° C. the activity of *T. reesei* endocellulase is barely measurable. In the case of the bacterial ones, it is obvious that the enzyme of SEQ ID NO: 2 displays activity that is more than twice the activity of *B. amyloliquefaciens* at all temperatures.

Figure 2:
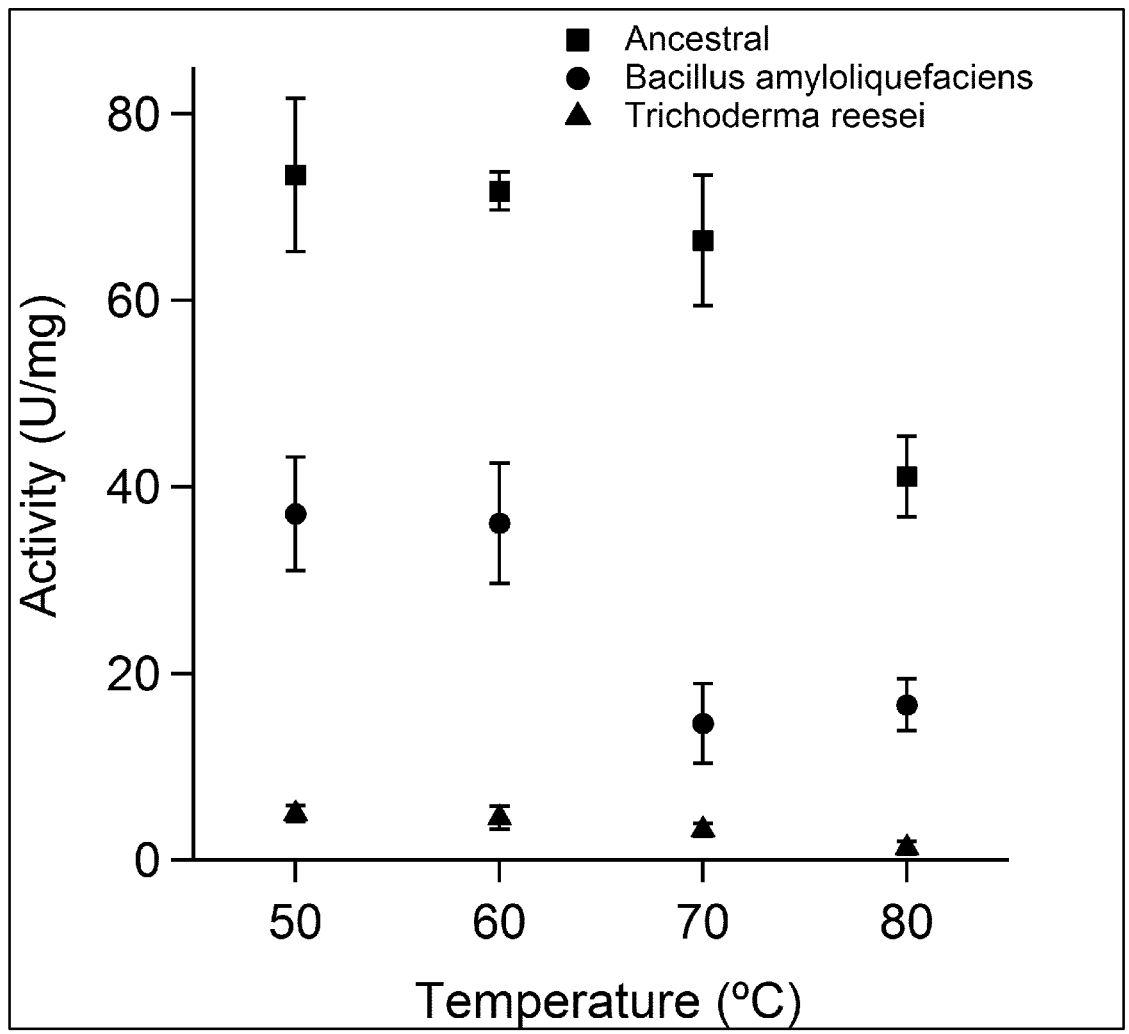
FIG. 2: Activity in U/mg of three different endocellulases: ancestral (Endocellulase catalytic domain (SEQ ID NO: 2)), square; *Bacillus amyloliquefacienes*, circle and *Trichoderma reesei*, triangle, measured at different temperatures (50° C., 60° C., 70° c. and 80° C.) with Megazyme endo-cellulase assay kit.

Similarly the activity can be expressed as Unit per mg of enzyme used. These results are shown in FIG. 2. In the present case the amount of enzyme used is quite similar in all cases, therefore the differences in activity between the three enzymes do not change.

Example 2: Thermal Ability of the Ancestral Endo-β-Ducanase

Figure 3:
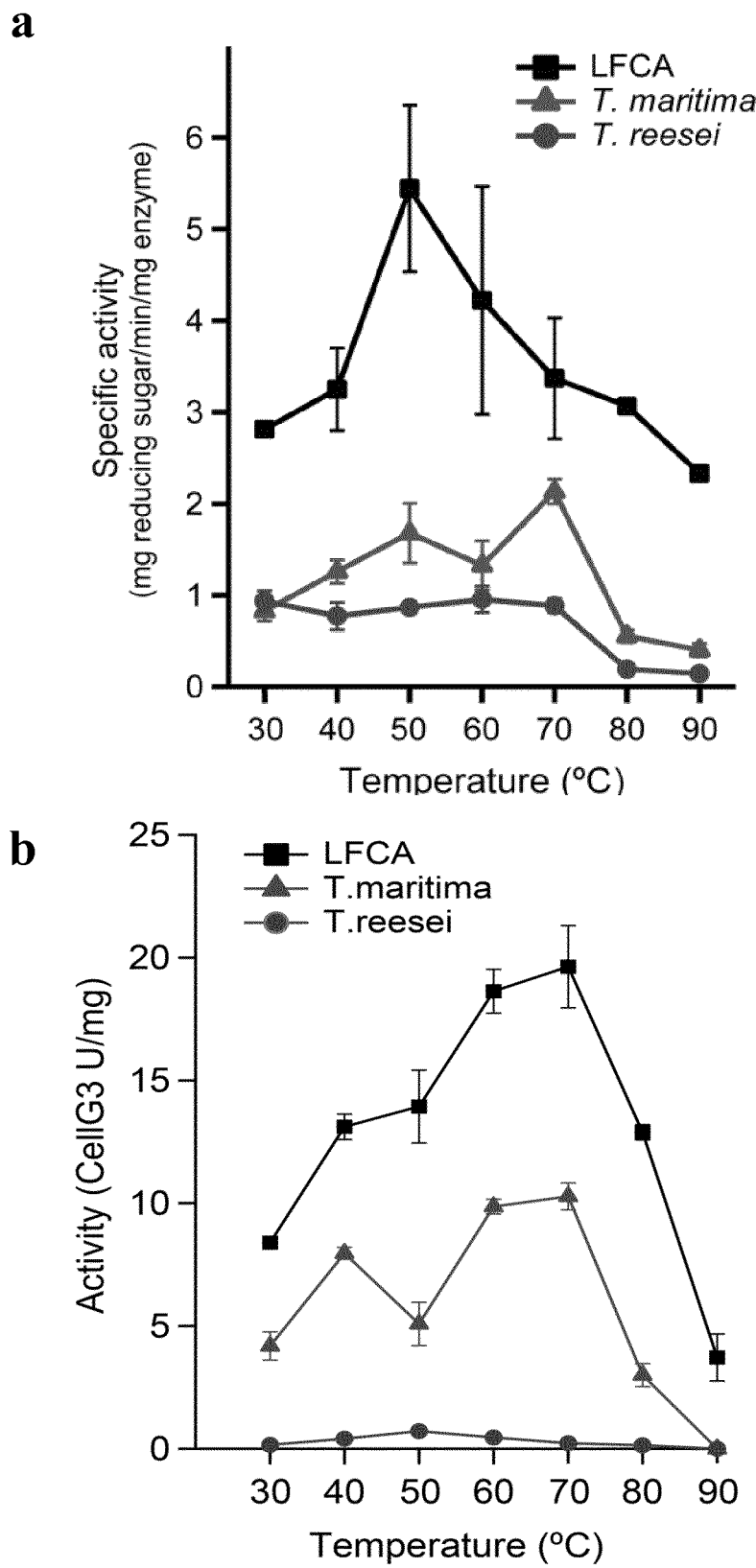
FIG. 3: Specific activity assay as a function of temperature for the ancestral endocellulase (SEQ ID NO: 69), *T. maritima* and *T. reesei* cellulases at pH 4.8. (A) Endocellulase activity measurements using the mg of reducing sugar equivalent released per minute and per mg of enzyme used (B) Endocellulase activity measurements using CellG3 method. Activity in CellG3 U/mg of three different endocellulases: ancestral (SEQ ID NO:69); *Termotoga maritima*, and *Trichoderma reesei*, measured in a range of temperatures (30-90° C.) at pH 5 with Megazyme endo-cellulase assay kit. We observed maximum activity at temperature 70° C. for LFCA and *T. maritima* endocellulases. All assays were triplicated. Experiments were carried as described in Material and Methods. In each case three replicates were collected. Average value and ±S. D. are shown for each measurement.

To test the thermal ability of endocellulase (SEQ ID NO:69), specific activity assays were performed at temperatures ranging from 30 to 90° C., and compared them with the activity of modern day enzymes at equal temperatures. We used soluble carboxymethil cellulose (CMC) as substrate. The activity was determined spectrophometrycally as the amount in mg of reducing sugar released per minute and per mg of enzyme used (see Material and Methods). The ancestral endocellulase outperformed the activity of *T. maritima* and *T. reesei* cellulases by a large margin, showing elevated activity at 90° C. (FIG. 3a). This is an extremely high temperature for an endocellulase only achieved by archaeal cellulases. Although the maximum activity is displayed at 50° C., this seems to be related to the substrate used, CMC. Experiments using and endocellulase specific substrate such as CellG3, report a different temperature profile with maximum activity at 70° C. (FIG. 3b). In any case, eve at 90° C. using soluble CMC, the ancestral cellulase shows higher temperature than bacterial and fungal cellulases at any temperature in the range tested.

Example 3: pH Stability of the Ancestral Endo-β-Glucanase

Figure 4:
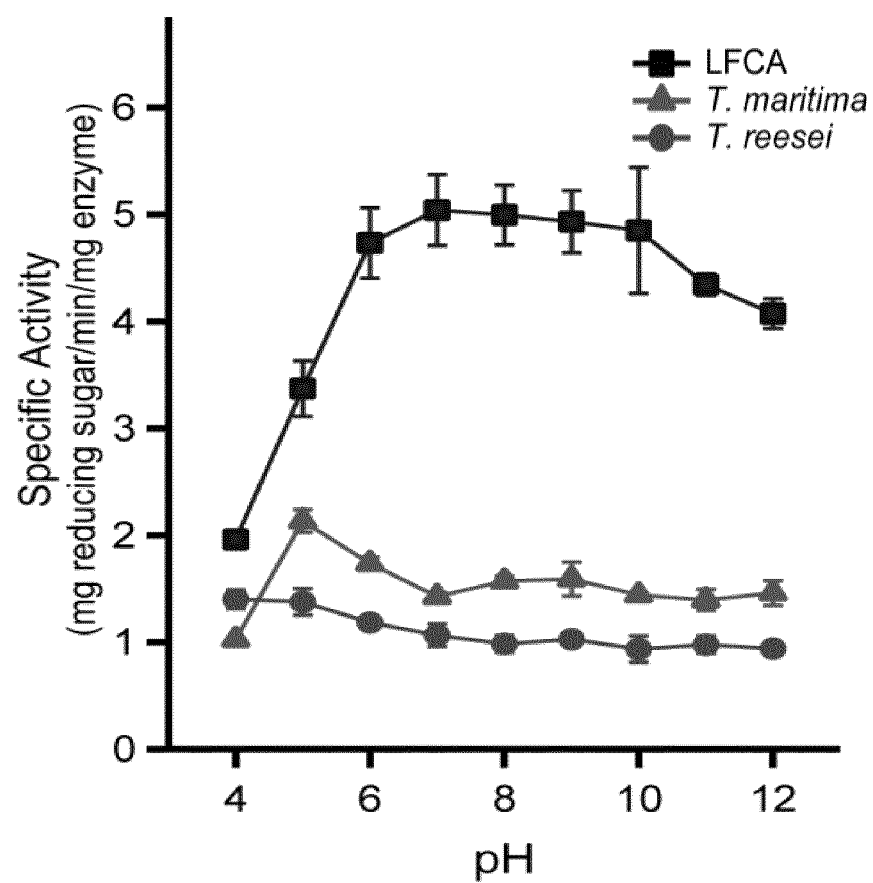
FIG. 4 Specific activity as a function of pH for the same enzymes as in FIG. 3 determined in the same way. Experiments performed at 70° C. temperature Experiments were carried as described in Material and Methods. In each case three replicates were collected. Average value and ±S. D. are shown for each measurement.
Figure 5:
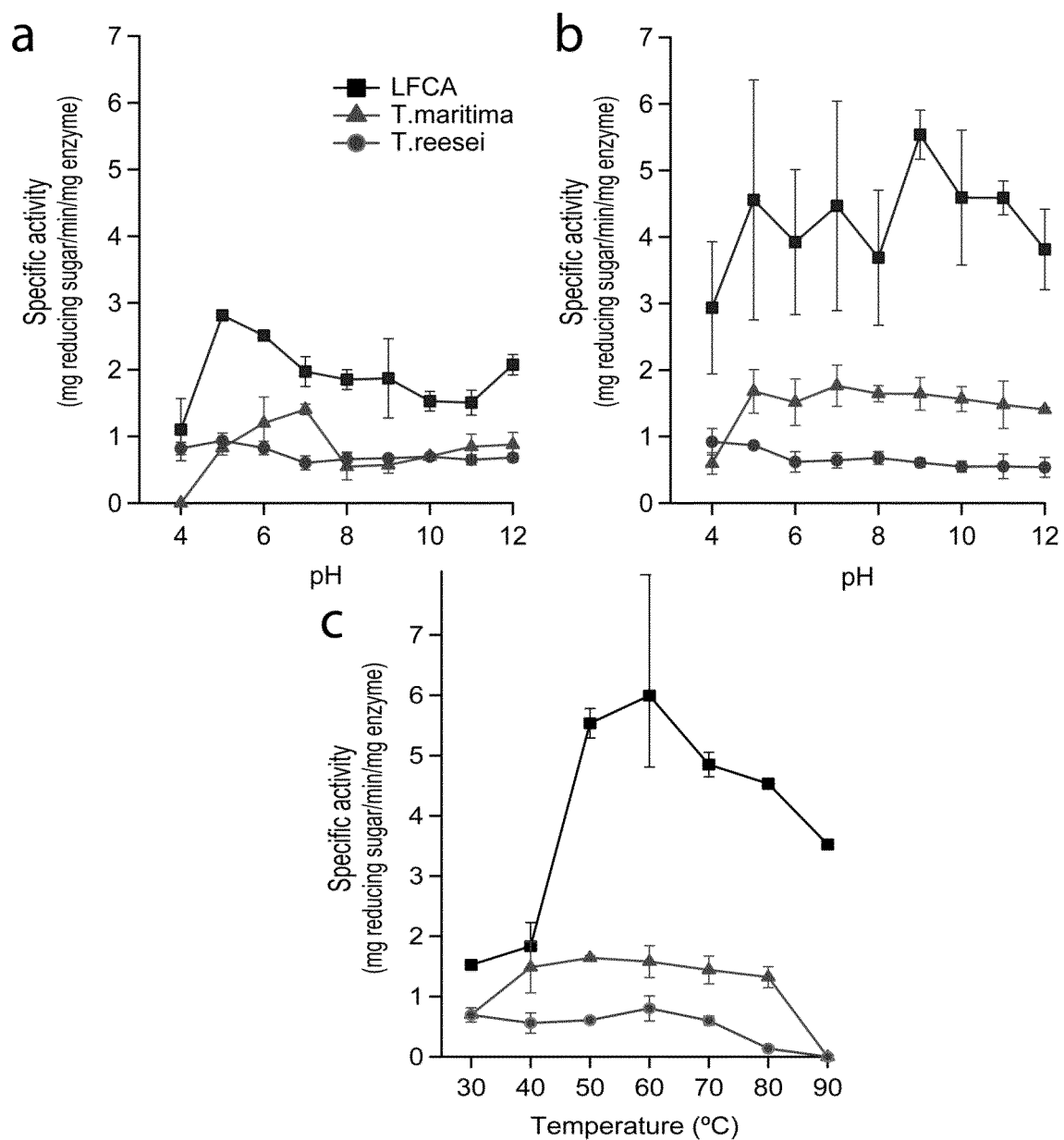
FIG. 5: Pre-incubation experiments at different temperature values during 30 min. Relative activities between the three enzymes are shown. Each enzyme was pre-incubated as it best performing pH value Experiments were carried as described in Material and Methods. In each case three

In addition, pretreatment of lignocellulosic material can be carried out at low or high pH values. Therefore, improving the pH dependence of cellulase activity is also of interest from an industrial point of view. We tested the pH dependence of cellulase activity in the range 4-12 at a temperature of 70° C. for the endocellulase (SEQ ID NO:69). We used the same substrate CMC and determined specific activity. Again, the ancestral cellulase outperformed the activity of the modern enzymes from *T. maritima* and *T. reesei*, showing a highly increased activity in the entire pH range but especially in the range 6-12 (FIG. 4). The activity in this range is about 5-fold that of *T. reesei* endoglucanase and over 3-fold that of *T. maritima*. We also acquired experiments combining different temperature and pH ranges (FIG. 5).

Example 4: Thermal Stability of the Ancestral Endo-β-Glucanase

Figure 6:
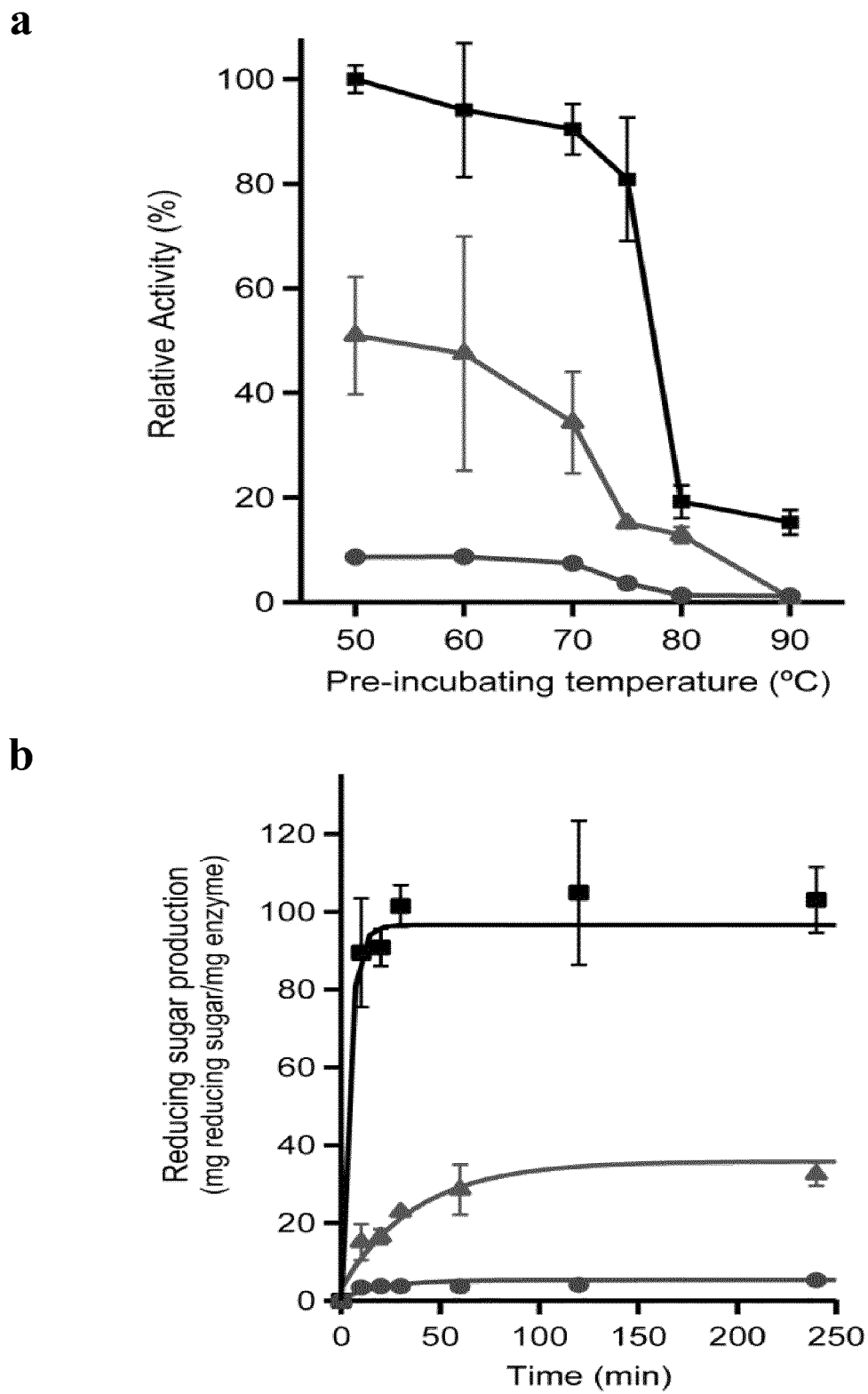
FIG. 6: Long-time activity measurements. The enzymatic reactions are carried at different periods of time and reducing sugar released is determined. Experiments were carried as described in Material and Methods. In each case three replicates were collected. Average value and ±S. D. are shown for each measurement.

We determined the relative thermal stability of endoglucanase of SEQ ID NO:69 as well as *T. maritima* and *T. reesei* cellulase by determining the temperature at which these enzymes loose half of their activity after 30 min incubation at different temperatures and them determining their residual activity at 60° C. We estimate a value of 72° C. for *T. maritime*, 74° C. for *T. reesei* and 78° C. for the ancestral endocelulase. Although these values are close, the relative activity amongst the enzymes demonstrates that the ancestral cellulase has a much higher activity that the other enzymes (FIG. 6a). Nevertheless, both bacterial *T. maritima* endoglucanase and ancestral endoglucanase maintained their relative activity. However, the fungal cellulase demonstrated a drastic decrease in activity after incubation at elevated temperatures. Finally, we also determined the long-time activity by measuring the activity at different reaction times from 10 to 250 min (FIG. 6b). It can be seen that the ancestral enzyme reach full reducing sugar production within the initial 10 minutes.

Figure 7:
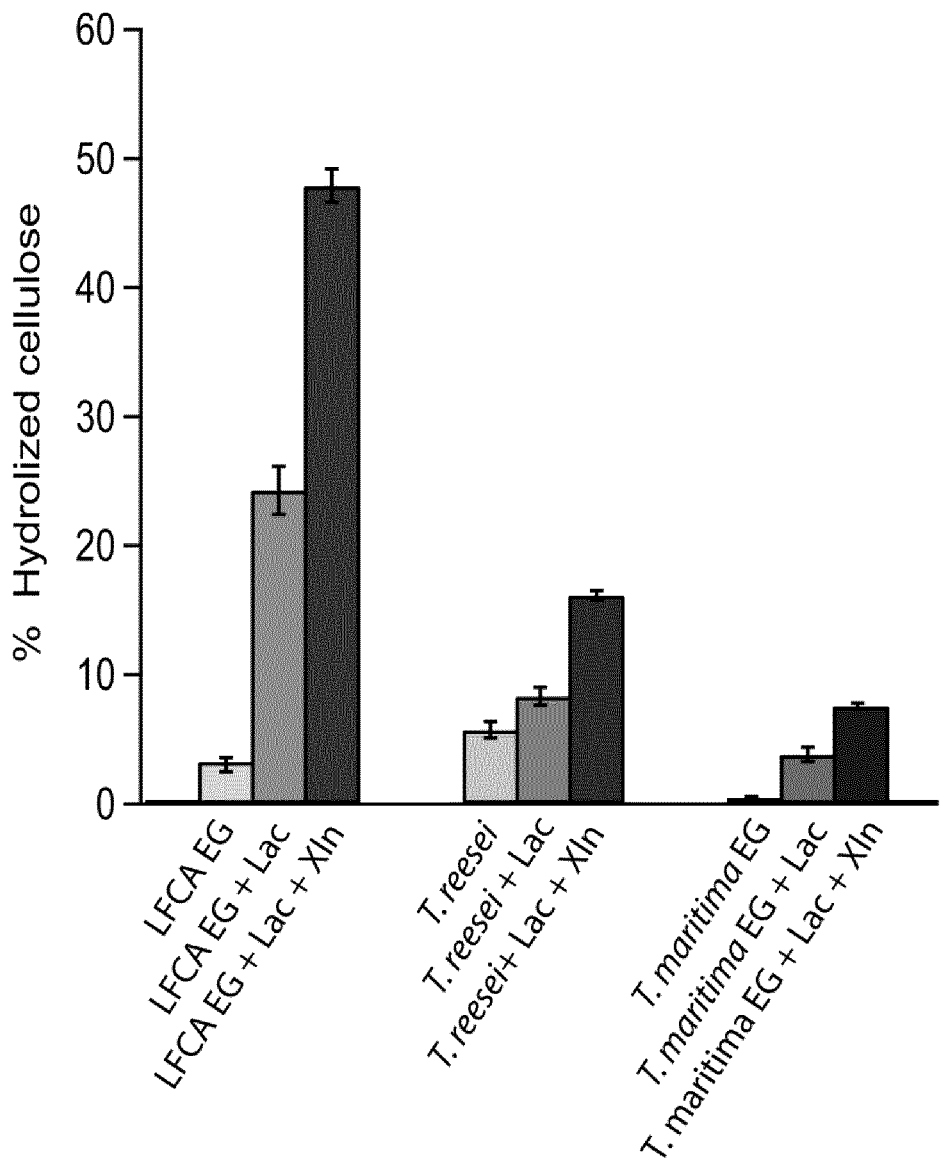
FIG. 7: Endocellulase activity measurements using CMC/DNS method. (a) Specific activity assay at 30° C. as a function of pH (4-12) for ancestral (SEQ ID NO: 69), *T. maritima* and *T. reesei* cellulases. We determined the reducing sugar mg equivalent released per minute and per mg of enzyme. (b) Specific activity assay at 50° C. as a function of pH (4-12) for ancestral (SEQ ID NO:69), *T. maritima* and *T. reesei* cellulases. (c) Specific activity assay in a range of temperatures (30-90° C.) at pH 10 for LFCA, *T. maritima* and *T. reesei* cellulases. All assays were triplicated.
Figure 8:
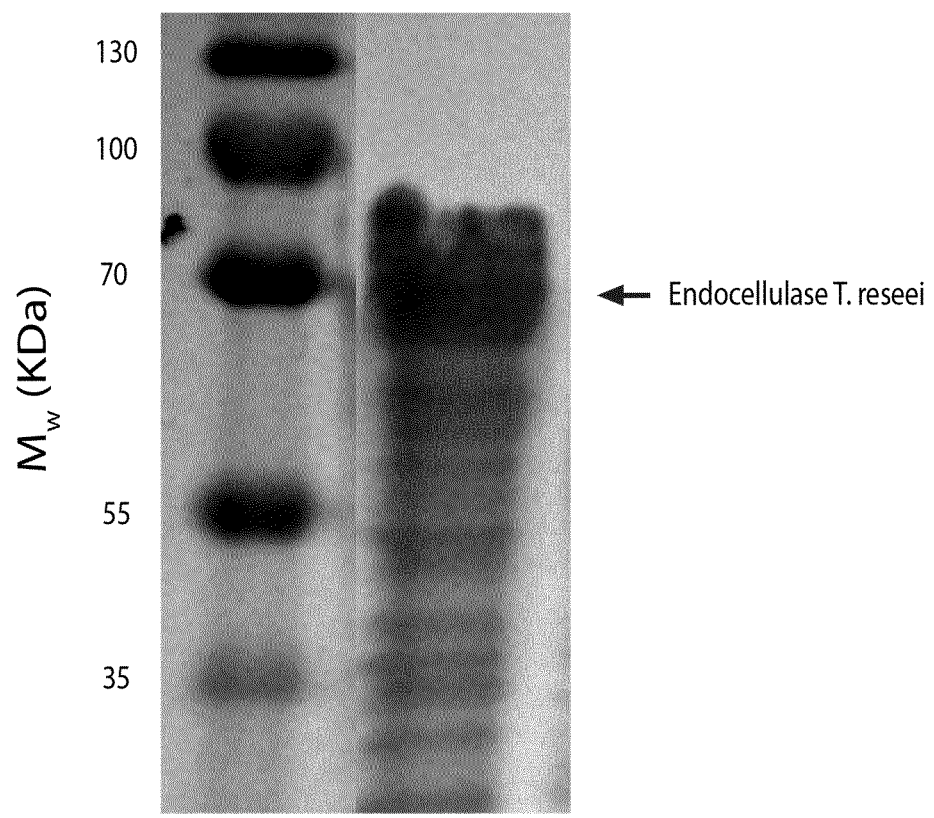
FIG. 8: SDS-PAGE acrylamide 8% gel of Celluclast enzyme cocktail. The main band represents endocellulase of *Trichoderma reesei* (~60 kDa).

Example 5: Activity of the Ancestral Endo-β-Glucanase Towards Lignocellulosic Biomass The previous experiments were carried out using CMC, a soluble laboratory substrate suitable for endocellulase activity. However, industrial application of cellulase in bioethanol production requires the enzymes to hydrolyze cellulase contained in lignocellulosic material such as agricultural or city waste. This material contains, apart from cellulose, lignin and hemicellulose. To gain access to cellulose it is necessary to remove lignin and hemicellulose what can be done during the pretreatment but also enzymatically by the synergistic action of laccase enzyme to degrade lignin and hemicellulases such as xylanase to hydrolyze hemicellulose. In order to test the ability of the ancestral endocellulase (SEQ ID NO:69) and the other enzymes to degrade cellulose from a non-ideal substrate we performed activity assays using cardboard as source of cellulose. In cardborad cellulose is present in a percentage of about 60%, lignin at 15% and hemicellulose at around 15%. The constitution of lignocellulosic biomass makes cellulose poorly accessible to enzymes unless lignin and hemicellulose are removed. We performed activity assays using only endocellulase and in combination with laccase and xylanase. We determined the percentage of cellulase hydrolyzed in a 50 mg sample of cardboard within one hour of hydrolysis at 50° C. and pH 4,8. As observed in FIG. 7, the cellulases alone degrade very little cellulase being the commercial *T. reesei* slightly more efficient that the ancestral endoglucanase. The commercial *T. reesei* is sold as a cocktail in which endocellulases represent the majority of it (FIG. 8); however, other cellulases are also present which may explain the higher activity observed. Conversely, ancestral endocellulase works best synergistically with laccase and xylanase to hydrolize about half of the cellulose present in the sample, which is much more than the other enzymes hydrolyze. This highlights the potential of our LFCA endoglucanase to work with industrial substrates, but also the advantage of using multi-enzyme cocktails for efficient cellulose pretreatment and hydrolysis.

SEQUENCE LISTING

This application contains a Sequence Listing which has been submitted electronically in ASCII format and is hereby incorporated by reference in its entirety.

The ASCII text file name is: 14_SequenceListing_Updated.txt
Creation date: 13 Jul. 2018
Size: 95,831 bytes.

The invention claimed is:

1. A polypeptide comprising an endocellulase catalytic domain, wherein the endocellulase catalytic domain has endocellulase activity and wherein the amino acid sequence of the endocellulase catalytic domain comprises an amino acid sequence that has at least 85% sequence identity to the amino acid sequence of SEQ ID NO: 2 or SEQ ID NO: 3 or at least 90% sequence identity to the amino acid sequence of SEQ ID NO: 69, over the complete length of SEQ ID NO: 2, 3, or 69.

2. The polypeptide according to claim 1, wherein the catalytic domain comprises an amino acid sequence selected from the group consisting of SEQ ID NO: 2, SEQ ID NO: 3 and SEQ ID NO: 69.

3. The polypeptide according to claim 1, further comprising a carbohydrate binding domain.

4. The polypeptide according to claim 3 wherein the carbohydrate binding domain comprises the sequence of SEQ ID NO: 4.

5. The polypeptide according to claim 3, wherein the endocellulase catalytic domain and the carbohydrate binding domain are connected by a linking domain.

6. The polypeptide according to claim 5 wherein the linking domain comprises the sequence of SEQ ID NO: 5, said linking domain being located between the catalytic domain and the carbohydrate binding domain.

7. The polypeptide according to claim 1, further comprising a tag suitable for detection and/or purification located at the N-terminus or at the C-terminus.

8. A nucleic acid encoding the polypeptide according to claim 1.

9. The nucleic acid according to claim 8, further comprising a sequence encoding a signal peptide fused in frame at the 5' terminus.

10. An expression cassette comprising the nucleic acid according to claim 8, wherein transcription and/or translation of said nucleic acid is under control of a suitable transcriptional and/or translational system.

11. A vector comprising the nucleic acid according to claim 8.

12. An isolated host cell comprising the nucleic acid according to claim 8.

13. A method for hydrolysing cellulose comprising contacting a sample containing cellulose with the polypeptide according to claim 1 under suitable conditions for hydrolysing cellulose.

14. The method according to claim 13 wherein the cellulose is contained in lignocellulosic material.

15. The method according to claim 14 wherein the hydrolysis is carried out in the presence of a laccase, a xylanase and/or a hemicellulase.

16. A method for producing bioethanol comprising
(i) contacting a sample containing cellulose with the polypeptide according to claim 1 under conditions suitable for hydrolysing crystalline cellulose, thereby obtaining endocellulase-treated cellulose,
(ii) converting the endocellulase-treated cellulose obtained in step (i) to cellobiose and/or cellotetraose using an exocellulase,
(iii) converting the cellobiose and/or cellotetraose obtained in step (ii) to glucose using a β-glucosidase, and
(iv) converting the glucose obtained in step (iii) to bioethanol in the presence of a yeast capable of producing bioethanol by fermentation of glucose.

17. The method according to claim 16 wherein the sample containing cellulose is a lignocellulosic material or wherein the hydrolysis in step (i) is carried out in the presence of a laccase, a xylanase and/or a hemicellulase.

18. A detergent composition comprising the polypeptide according to claim 1 and a surfactant.

19. The polypeptide according to claim 1, wherein the amino acid sequence of said endocellulase catalytic domain has at least 90% sequence identity with the amino acid sequence of SEQ ID NO: 2 or 3, over the complete length of SEQ ID NO: 2 or 3.

20. The polypeptide according to claim 1, wherein the amino acid sequence of said endocellulase catalytic domain has at least 95% sequence identity with the amino acid sequence of SEQ ID NO: 2, 3, or 69 over the complete length of SEQ ID NO: 2, 3, or 69.

* * * * *

SEQUENCE LISTING

```
<160> NUMBER OF SEQ ID NOS: 69

<210> SEQ ID NO 1
<211> LENGTH: 297
<212> TYPE: PRT
<213> ORGANISM: Artificial Sequence
<220> FEATURE:
<223> OTHER INFORMATION: Consensus sequence of an endocellulase
      catalytic domain
<220> FEATURE:
<221> NAME/KEY: misc_feature
<222> LOCATION: (5)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (12)..(12)
```

```
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid
<220> FEATURE:
<221> NAME/KEY: misc_feature
<222> LOCATION: (17)..(20)
<223> OTHER INFORMATION: Xaa can be any naturally occurring amino acid
<220> FEATURE:
<221> NAME/KEY: misc_feature
<222> LOCATION: (24)..(24)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (34)..(34)
<223> OTHER INFORMATION: Xaa can be any naturally occurring amino acid
<220> FEATURE:
<221> NAME/KEY: misc_feature
<222> LOCATION: (39)..(40)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (46)..(48)
<223> OTHER INFORMATION: Xaa can be any naturally occurring amino acid
<220> FEATURE:
<221> NAME/KEY: misc_feature
<222> LOCATION: (50)..(51)
<223> OTHER INFORMATION: Xaa can be any naturally occurring amino acid
<220> FEATURE:
<221> NAME/KEY: misc_feature
<222> LOCATION: (54)..(57)
<223> OTHER INFORMATION: Xaa can be any naturally occurring amino acid
<220> FEATURE:
<221> NAME/KEY: misc_feature
<222> LOCATION: (60)..(60)
<223> OTHER INFORMATION: Xaa can be any naturally occurring amino acid
<220> FEATURE:
<221> NAME/KEY: misc_feature
<222> LOCATION: (64)..(65)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (70)..(70)
<223> OTHER INFORMATION: Xaa can be any naturally occurring amino acid
<220> FEATURE:
<221> NAME/KEY: misc_feature
<222> LOCATION: (74)..(76)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (80)..(82)
<223> OTHER INFORMATION: Xaa can be any naturally occurring amino acid
<220> FEATURE:
<221> NAME/KEY: misc_feature
<222> LOCATION: (85)..(85)
<223> OTHER INFORMATION: Xaa can be any naturally occurring amino acid
<220> FEATURE:
<221> NAME/KEY: misc_feature
<222> LOCATION: (87)..(89)
<223> OTHER INFORMATION: Xaa can be any naturally occurring amino acid
<220> FEATURE:
<221> NAME/KEY: misc_feature
```

```
<222> LOCATION: (94)..(94)
<223> OTHER INFORMATION: Xaa can be any naturally occurring amino acid
<220> FEATURE:
<221> NAME/KEY: misc_feature
<222> LOCATION: (101)..(103)
<223> OTHER INFORMATION: Xaa can be any naturally occurring amino acid
<220> FEATURE:
<221> NAME/KEY: misc_feature
<222> LOCATION: (107)..(111)
<223> OTHER INFORMATION: Xaa can be any naturally occurring amino acid
<220> FEATURE:
<221> NAME/KEY: misc_feature
<222> LOCATION: (114)..(114)
<223> OTHER INFORMATION: Xaa can be any naturally occurring amino acid
<220> FEATURE:
<221> NAME/KEY: misc_feature
<222> LOCATION: (117)..(117)
<223> OTHER INFORMATION: Xaa can be any naturally occurring amino acid
<220> FEATURE:
<221> NAME/KEY: misc_feature
<222> LOCATION: (119)..(119)
<223> OTHER INFORMATION: Xaa can be any naturally occurring amino acid
<220> FEATURE:
<221> NAME/KEY: misc_feature
<222> LOCATION: (122)..(127)
<223> OTHER INFORMATION: Xaa can be any naturally occurring amino acid
<220> FEATURE:
<221> NAME/KEY: misc_feature
<222> LOCATION: (134)..(134)
<223> OTHER INFORMATION: Xaa can be any naturally occurring amino acid
<220> FEATURE:
<221> NAME/KEY: misc_feature
<222> LOCATION: (142)..(142)
<223> OTHER INFORMATION: Xaa can be any naturally occurring amino acid
<220> FEATURE:
<221> NAME/KEY: misc_feature
<222> LOCATION: (146)..(146)
<223> OTHER INFORMATION: Xaa can be any naturally occurring amino acid
<220> FEATURE:
<221> NAME/KEY: misc_feature
<222> LOCATION: (149)..(149)
<223> OTHER INFORMATION: Xaa can be any naturally occurring amino acid
<220> FEATURE:
<221> NAME/KEY: misc_feature
<222> LOCATION: (157)..(157)
<223> OTHER INFORMATION: Xaa can be any naturally occurring amino acid
<220> FEATURE:
<221> NAME/KEY: misc_feature
<222> LOCATION: (165)..(167)
<223> OTHER INFORMATION: Xaa can be any naturally occurring amino acid
<220> FEATURE:
<221> NAME/KEY: misc_feature
<222> LOCATION: (172)..(173)
<223> OTHER INFORMATION: Xaa can be any naturally occurring amino acid
<220> FEATURE:
<221> NAME/KEY: misc_feature
<222> LOCATION: (176)..(176)
<223> OTHER INFORMATION: Xaa can be any naturally occurring amino acid
<220> FEATURE:
<221> NAME/KEY: misc_feature
<222> LOCATION: (178)..(183)
<223> OTHER INFORMATION: Xaa can be any naturally occurring amino acid
<220> FEATURE:
<221> NAME/KEY: misc_feature
<222> LOCATION: (186)..(188)
<223> OTHER INFORMATION: Xaa can be any naturally occurring amino acid
<220> FEATURE:
<221> NAME/KEY: misc_feature
<222> LOCATION: (195)..(195)
<223> OTHER INFORMATION: Xaa can be any naturally occurring amino acid
<220> FEATURE:
<221> NAME/KEY: misc_feature
<222> LOCATION: (200)..(201)
<223> OTHER INFORMATION: Xaa can be any naturally occurring amino acid
<220> FEATURE:
<221> NAME/KEY: misc_feature
<222> LOCATION: (203)..(206)
<223> OTHER INFORMATION: Xaa can be any naturally occurring amino acid
<220> FEATURE:
```

```
<221> NAME/KEY: misc_feature
<222> LOCATION: (209)..(212)
<223> OTHER INFORMATION: Xaa can be any naturally occurring amino acid
<220> FEATURE:
<221> NAME/KEY: misc_feature
<222> LOCATION: (214)..(216)
<223> OTHER INFORMATION: Xaa can be any naturally occurring amino acid
<220> FEATURE:
<221> NAME/KEY: misc_feature
<222> LOCATION: (218)..(220)
<223> OTHER INFORMATION: Xaa can be any naturally occurring amino acid
<220> FEATURE:
<221> NAME/KEY: misc_feature
<222> LOCATION: (225)..(225)
<223> OTHER INFORMATION: Xaa can be any naturally occurring amino acid
<220> FEATURE:
<221> NAME/KEY: misc_feature
<222> LOCATION: (228)..(231)
<223> OTHER INFORMATION: Xaa can be any naturally occurring amino acid
<220> FEATURE:
<221> NAME/KEY: misc_feature
<222> LOCATION: (233)..(233)
<223> OTHER INFORMATION: Xaa can be any naturally occurring amino acid
<220> FEATURE:
<221> NAME/KEY: misc_feature
<222> LOCATION: (236)..(237)
<223> OTHER INFORMATION: Xaa can be any naturally occurring amino acid
<220> FEATURE:
<221> NAME/KEY: misc_feature
<222> LOCATION: (239)..(240)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (247)..(250)
<223> OTHER INFORMATION: Xaa can be any naturally occurring amino acid
<220> FEATURE:
<221> NAME/KEY: misc_feature
<222> LOCATION: (252)..(252)
<223> OTHER INFORMATION: Xaa can be any naturally occurring amino acid
<220> FEATURE:
<221> NAME/KEY: misc_feature
<222> LOCATION: (254)..(254)
<223> OTHER INFORMATION: Xaa can be any naturally occurring amino acid
<220> FEATURE:
<221> NAME/KEY: misc_feature
<222> LOCATION: (259)..(260)
<223> OTHER INFORMATION: Xaa can be any naturally occurring amino acid
<220> FEATURE:
<221> NAME/KEY: misc_feature
<222> LOCATION: (264)..(264)
<223> OTHER INFORMATION: Xaa can be any naturally occurring amino acid
<220> FEATURE:
<221> NAME/KEY: misc_feature
<222> LOCATION: (266)..(266)
<223> OTHER INFORMATION: Xaa can be any naturally occurring amino acid
<220> FEATURE:
<221> NAME/KEY: misc_feature
<222> LOCATION: (271)..(271)
<223> OTHER INFORMATION: Xaa can be any naturally occurring amino acid
<220> FEATURE:
<221> NAME/KEY: misc_feature
<222> LOCATION: (274)..(277)
<223> OTHER INFORMATION: Xaa can be any naturally occurring amino acid
<220> FEATURE:
<221> NAME/KEY: misc_feature
<222> LOCATION: (279)..(279)
<223> OTHER INFORMATION: Xaa can be any naturally occurring amino acid
<220> FEATURE:
<221> NAME/KEY: misc_feature
<222> LOCATION: (282)..(284)
<223> OTHER INFORMATION: Xaa can be any naturally occurring amino acid
<220> FEATURE:
<221> NAME/KEY: misc_feature
<222> LOCATION: (286)..(287)
<223> OTHER INFORMATION: Xaa can be any naturally occurring amino acid
```

```
<220> FEATURE:
<221> NAME/KEY: misc_feature
<222> LOCATION: (290)..(290)
<223> OTHER INFORMATION: Xaa can be any naturally occurring amino acid
<220> FEATURE:
<221> NAME/KEY: misc_feature
<222> LOCATION: (295)..(295)
<223> OTHER INFORMATION: Xaa can be any naturally occurring amino acid

<400> SEQUENCE: 1

Thr Pro Val Glu Xaa Xaa Gly Gln Leu Xaa Val Xaa Gly Xaa Gln Leu
1               5                   10                  15

Xaa Xaa Xaa Xaa Gly Lys Pro Xaa Gln Leu Arg Gly Met Ser Xaa His
            20                  25                  30

Gly Xaa Gln Trp Phe Gly Xaa Xaa Val Asn Xaa Xaa Ser Xaa Xaa Xaa
        35                  40                  45

Leu Xaa Xaa Asp Trp Xaa Xaa Xaa Xaa Phe Arg Xaa Ala Met Tyr Xaa
    50                  55                  60

Xaa Glu Xaa Gly Tyr Xaa Thr Asn Pro Xaa Xaa Xaa Asn Xaa Val Xaa
65                  70                  75                  80

Xaa Xaa Val Glu Xaa Ala Xaa Xaa Gly Met Tyr Val Xaa Ile Asp
                85                  90                  95

Trp His Ile Leu Xaa Xaa Xaa Asp Pro Asn Xaa Xaa Xaa Xaa Xaa Ala
            100                 105                 110

Lys Xaa Phe Phe Xaa Glu Xaa Ala Ala Xaa Xaa Xaa Xaa Xaa Xaa Asn
            115                 120                 125

Val Ile Tyr Glu Ile Xaa Asn Glu Pro Asn Gly Gly Val Xaa Trp Ser
            130                 135                 140

Asn Xaa Ile Lys Xaa Tyr Ala Glu Glu Val Ile Pro Xaa Ile Arg Ala
145             150                 155                 160

Asn Asp Pro Asp Xaa Xaa Xaa Ile Val Gly Thr Xaa Xaa Trp Ser Xaa
                165                 170                 175

Asp Xaa Xaa Xaa Xaa Xaa Xaa Asn Pro Xaa Xaa Xaa Ser Asn Ile Met
            180                 185                 190

Tyr Ala Xaa His Phe Tyr Ala Xaa Xaa His Xaa Xaa Xaa Xaa Arg Asp
            195                 200                 205

Xaa Xaa Xaa Xaa Ala Xaa Xaa Xaa Gly Xaa Xaa Xaa Phe Val Thr Glu
        210                 215                 220

Xaa Gly Thr Xaa Xaa Xaa Xaa Gly Xaa Gly Gly Xaa Xaa Leu Xaa Xaa
225             230                 235                 240

Ser Gln Lys Trp Xaa Asp Xaa Xaa Xaa Xaa Arg Xaa Ile Xaa Trp Ala
            245                 250                 255

Asn Trp Xaa Xaa Ser Asp Lys Xaa Glu Xaa Ser Ala Ala Leu Xaa Pro
            260                 265                 270

Gly Xaa Xaa Xaa Xaa Gly Xaa Trp Thr Xaa Xaa Xaa Leu Xaa Xaa Ser
        275                 280                 285

Gly Xaa Phe Val Arg Glu Xaa Ile Arg
    290                 295

<210> SEQ ID NO 2
<211> LENGTH: 297
<212> TYPE: PRT
<213> ORGANISM: Artificial Sequence
<220> FEATURE:
<223> OTHER INFORMATION: Endocellulase catalytic domain

<400> SEQUENCE: 2

Thr Pro Val Glu Thr His Gly Gln Leu Ser Val Lys Gly Gly Gln Leu
```

```
             1               5                  10                 15
          Val Asp Glu Asn Gly Lys Pro Val Gln Leu Arg Gly Met Ser Ser His
                           20                 25                 30
          Gly Leu Gln Trp Phe Gly Asp Phe Val Asn Lys Asp Ser Met Lys Trp
                           35                 40                 45
          Leu Arg Asp Asp Trp Gly Ile Asn Val Phe Arg Val Ala Met Tyr Thr
           50                 55                 60
          Ala Glu Gly Gly Tyr Ile Thr Asn Pro Ser Val Lys Asn Lys Val Lys
           65                 70                 75                 80
          Glu Ala Val Glu Ala Ala Ile Asp Leu Gly Met Tyr Val Ile Ile Asp
                           85                 90                 95
          Trp His Ile Leu Ser Asp Asn Asp Pro Asn Thr Tyr Lys Glu Gln Ala
                          100                105                110
          Lys Ala Phe Phe Gln Glu Met Ala Ala Lys Tyr Gly Asn Tyr Pro Asn
                          115                120                125
          Val Ile Tyr Glu Ile Cys Asn Glu Pro Asn Gly Gly Val Thr Trp Ser
                          130                135                140
          Asn Gln Ile Lys Pro Tyr Ala Glu Glu Val Ile Pro Ala Ile Arg Ala
          145                150                155                160
          Asn Asp Pro Asp Asn Ile Ile Val Gly Thr Pro Thr Trp Ser Gln
                          165                170                175
          Asp Val His Asp Ala Ala Asp Asn Pro Leu Pro Tyr Ser Asn Ile Met
                          180                185                190
          Tyr Ala Leu His Phe Tyr Ala Gly Thr His Gly Gln Ser Leu Arg Asp
                          195                200                205
          Lys Ile Asp Tyr Ala Leu Ser Lys Gly Val Ala Ile Phe Val Thr Glu
                          210                215                220
          Trp Gly Thr Ser Asp Ala Ser Gly Asn Gly Pro Phe Leu Asn Glu
          225                230                235                240
          Ser Gln Lys Trp Ile Asp Phe Met Asn Ser Arg Asn Ile Ser Trp Ala
                          245                250                255
          Asn Trp Ser Leu Ser Asp Lys Ser Glu Thr Ser Ala Ala Leu Met Pro
                          260                265                270
          Gly Ala Ser Pro Thr Gly Gly Trp Thr Asp Ser Asn Leu Ser Ala Ser
                          275                280                285
          Gly Lys Phe Val Arg Glu Gln Ile Arg
                          290                295

<210> SEQ ID NO 3
<211> LENGTH: 297
<212> TYPE: PRT
<213> ORGANISM: Artificial Sequence
<220> FEATURE:
<223> OTHER INFORMATION: Endocellulase catalytic domain

<400> SEQUENCE: 3

Thr Pro Val Glu Ile Asn Gly Gln Leu Gln Val Cys Gly Val Gln Leu
          1               5                  10                 15
          Cys Asn Gln Tyr Gly Lys Pro Ile Gln Leu Arg Gly Met Ser Thr His
                           20                 25                 30
          Gly Ile Gln Trp Phe Gly Asn Cys Val Asn Asn Ala Ser Leu Asp Ala
                           35                 40                 45
          Leu Ala Asn Asp Trp Arg Ala Asp Ile Phe Arg Ile Ala Met Tyr Ile
           50                 55                 60
          Gln Glu Asp Gly Tyr Glu Thr Asn Pro Ala Gly Thr Asn Arg Val Asn
```

```
                 65                  70                  75                  80
        Asn Leu Val Glu Glu Ala Thr Ala Arg Gly Met Tyr Val Leu Ile Asp
                         85                  90                  95

Trp His Ile Leu Thr Pro Gly Asp Pro Asn Tyr Asn Leu Asp Arg Ala
                        100                 105                 110

Lys Thr Phe Phe Ala Glu Ile Ala Ala Arg His Ala Ser Lys Thr Asn
                        115                 120                 125

Val Ile Tyr Glu Ile Ala Asn Glu Pro Asn Gly Gly Val Ser Trp Ser
                130                 135                 140

Asn Thr Ile Lys Ser Tyr Ala Glu Glu Val Ile Pro Val Ile Arg Ala
        145                 150                 155                 160

Asn Asp Pro Asp Ser Val Ile Val Gly Thr Arg Gly Trp Ser Ser
                        165                 170                 175

Asp Ser Thr Glu Ile Val Asn Asn Pro Val Asn Ala Ser Asn Ile Met
                        180                 185                 190

Tyr Ala Phe His Phe Tyr Ala Ala Ser His Arg Asp Asn Tyr Arg Asp
                        195                 200                 205

Glu Val Glu Arg Ala Ala Ala Arg Gly Leu Pro Val Phe Val Thr Glu
                        210                 215                 220

Phe Gly Thr Val Thr Tyr Thr Gly Asp Gly Asn Asp Leu Ala Ser
        225                 230                 235                 240

Ser Gln Lys Trp Leu Asp Leu Leu Asp Ala Arg Lys Ile Gly Trp Ala
                        245                 250                 255

Asn Trp Asn Phe Ser Asp Lys Ala Glu Ser Ser Ala Ala Leu Arg Pro
                        260                 265                 270

Gly Thr Cys Ala Gly Gly Ser Trp Thr Gly Thr Ser Leu Thr Pro Ser
                        275                 280                 285

Gly Val Phe Val Arg Glu Arg Ile Arg
                        290                 295

<210> SEQ ID NO 4
<211> LENGTH: 163
<212> TYPE: PRT
<213> ORGANISM: Artificial Sequence
<220> FEATURE:
<223> OTHER INFORMATION: Carbohydrate binding domain

<400> SEQUENCE: 4

Met Thr Pro Gly Glu Glu Phe Tyr Val Glu Ala Ala Val Asn Ala Ala
        1               5                   10                  15

Gly Pro Gly Phe Val Asn Ile Lys Ala Ser Ile Ile Asn Lys Ser Gly
                        20                  25                  30

Trp Pro Ala Arg Gly Ser Asp Lys Leu Ser Ala Lys Tyr Phe Val Asp
                        35                  40                  45

Ile Ser Glu Ala Val Ala Lys Gly Ile Thr Leu Asp Gln Ile Thr Val
                50                  55                  60

Gln Ser Thr Thr Asn Gly Gly Ala Lys Val Ser Gln Leu Leu Pro Trp
        65                  70                  75                  80

Asp Pro Asp Asn His Ile Tyr Tyr Val Asn Ile Asp Phe Thr Gly Ile
                        85                  90                  95

Asn Ile Phe Pro Gly Gly Ile Asn Glu Tyr Lys Arg Asp Val Tyr Phe
                        100                 105                 110

Thr Ile Thr Ala Pro Tyr Gly Glu Gly Asn Trp Asp Asn Thr Asn Asp
                        115                 120                 125

Phe Ser Phe Gln Gly Leu Glu Gln Gly Phe Thr Ser Lys Lys Thr Glu
```

```
                130                 135                 140

Tyr Ile Pro Leu Tyr Asp Gly Asn Val Arg Val Trp Gly Lys Val Pro
145                 150                 155                 160

Asp Arg Ser

<210> SEQ ID NO 5
<211> LENGTH: 30
<212> TYPE: PRT
<213> ORGANISM: Artificial Sequence
<220> FEATURE:
<223> OTHER INFORMATION: Linker domain

<400> SEQUENCE: 5

Lys Met Tyr Asp Met Tyr Gly Gly Glu Pro Leu Glu Asn Trp Pro Gln
1               5                   10                  15

Pro Glu Asp Phe Arg Ala Pro Gly Asp Asp Ile Val Arg Ser
            20                  25                  30

<210> SEQ ID NO 6
<211> LENGTH: 490
<212> TYPE: PRT
<213> ORGANISM: Artificial Sequence
<220> FEATURE:
<223> OTHER INFORMATION: Polypeptide comprising an endocellulase
      catalytic domain

<400> SEQUENCE: 6

Met Thr Pro Gly Glu Glu Phe Tyr Val Glu Ala Ala Val Asn Ala Ala
1               5                   10                  15

Gly Pro Gly Phe Val Asn Ile Lys Ala Ser Ile Ile Asn Lys Ser Gly
            20                  25                  30

Trp Pro Ala Arg Gly Ser Asp Lys Leu Ser Ala Lys Tyr Phe Val Asp
        35                  40                  45

Ile Ser Glu Ala Val Ala Lys Gly Ile Thr Leu Asp Gln Ile Thr Val
    50                  55                  60

Gln Ser Thr Thr Asn Gly Gly Ala Lys Val Ser Gln Leu Leu Pro Trp
65                  70                  75                  80

Asp Pro Asp Asn His Ile Tyr Tyr Val Asn Ile Asp Phe Thr Gly Ile
                85                  90                  95

Asn Ile Phe Pro Gly Gly Ile Asn Glu Tyr Lys Arg Asp Val Tyr Phe
            100                 105                 110

Thr Ile Thr Ala Pro Tyr Gly Glu Gly Asn Trp Asp Asn Thr Asn Asp
        115                 120                 125

Phe Ser Phe Gln Gly Leu Glu Gln Gly Phe Thr Ser Lys Lys Thr Glu
    130                 135                 140

Tyr Ile Pro Leu Tyr Asp Gly Asn Val Arg Val Trp Gly Lys Val Pro
145                 150                 155                 160

Asp Arg Ser Lys Met Tyr Asp Met Tyr Gly Gly Glu Pro Leu Glu Asn
                165                 170                 175

Trp Pro Gln Pro Glu Asp Phe Arg Ala Pro Gly Asp Asp Ile Val Arg
            180                 185                 190

Ser Thr Pro Val Glu Thr His Gly Gln Leu Ser Val Lys Gly Gly Gln
        195                 200                 205

Leu Val Asp Glu Asn Gly Lys Pro Val Gln Leu Arg Gly Met Ser Ser
    210                 215                 220

His Gly Leu Gln Trp Phe Gly Asp Phe Val Asn Lys Asp Ser Met Lys
225                 230                 235                 240
```

Trp Leu Arg Asp Asp Trp Gly Ile Asn Val Phe Arg Val Ala Met Tyr
            245                 250                 255

Thr Ala Glu Gly Gly Tyr Ile Thr Asn Pro Ser Val Lys Asn Lys Val
            260                 265                 270

Lys Glu Ala Val Glu Ala Ala Ile Asp Leu Gly Met Tyr Val Ile Ile
            275                 280                 285

Asp Trp His Ile Leu Ser Asp Asn Pro Asn Thr Tyr Lys Glu Gln
            290                 295                 300

Ala Lys Ala Phe Phe Gln Glu Met Ala Ala Lys Tyr Gly Asn Tyr Pro
305                 310                 315                 320

Asn Val Ile Tyr Glu Ile Cys Asn Glu Pro Asn Gly Gly Val Thr Trp
            325                 330                 335

Ser Asn Gln Ile Lys Pro Tyr Ala Glu Glu Val Ile Pro Ala Ile Arg
            340                 345                 350

Ala Asn Asp Pro Asp Asn Ile Ile Ile Val Gly Thr Pro Thr Trp Ser
            355                 360                 365

Gln Asp Val His Asp Ala Ala Asp Asn Pro Leu Pro Tyr Ser Asn Ile
            370                 375                 380

Met Tyr Ala Leu His Phe Tyr Ala Gly Thr His Gly Gln Ser Leu Arg
385                 390                 395                 400

Asp Lys Ile Asp Tyr Ala Leu Ser Lys Gly Val Ala Ile Phe Val Thr
            405                 410                 415

Glu Trp Gly Thr Ser Asp Ala Ser Gly Asn Gly Pro Phe Leu Asn
            420                 425                 430

Glu Ser Gln Lys Trp Ile Asp Phe Met Asn Ser Arg Asn Ile Ser Trp
            435                 440                 445

Ala Asn Trp Ser Leu Ser Asp Lys Ser Glu Thr Ser Ala Ala Leu Met
450                 455                 460

Pro Gly Ala Ser Pro Thr Gly Gly Trp Thr Asp Ser Asn Leu Ser Ala
465                 470                 475                 480

Ser Gly Lys Phe Val Arg Glu Gln Ile Arg
            485                 490

<210> SEQ ID NO 7
<211> LENGTH: 490
<212> TYPE: PRT
<213> ORGANISM: Artificial Sequence
<220> FEATURE:
<223> OTHER INFORMATION: Polypeptide comprising an endocellulase
      catalytic domain

<400> SEQUENCE: 7

Met Thr Pro Gly Glu Glu Phe Tyr Val Glu Ala Ala Val Asn Ala Ala
1               5                   10                  15

Gly Pro Gly Phe Val Asn Ile Lys Ala Ser Ile Ile Asn Lys Ser Gly
            20                  25                  30

Trp Pro Ala Arg Gly Ser Asp Lys Leu Ser Ala Lys Tyr Phe Val Asp
            35                  40                  45

Ile Ser Glu Ala Val Ala Lys Gly Ile Thr Leu Asp Gln Ile Thr Val
            50                  55                  60

Gln Ser Thr Thr Asn Gly Gly Ala Lys Val Ser Gln Leu Leu Pro Trp
65                  70                  75                  80

Asp Pro Asp Asn His Ile Tyr Tyr Val Asn Ile Asp Phe Thr Gly Ile
            85                  90                  95

Asn Ile Phe Pro Gly Gly Ile Asn Glu Tyr Lys Arg Asp Val Tyr Phe
            100                 105                 110

```
Thr Ile Thr Ala Pro Tyr Gly Glu Gly Asn Trp Asp Asn Thr Asn Asp
            115                 120                 125

Phe Ser Phe Gln Gly Leu Glu Gln Gly Phe Thr Ser Lys Lys Thr Glu
130             135                 140

Tyr Ile Pro Leu Tyr Asp Gly Asn Val Arg Val Trp Gly Lys Val Pro
145                 150                 155                 160

Asp Arg Ser Lys Met Tyr Asp Met Tyr Gly Gly Glu Pro Leu Glu Asn
                165                 170                 175

Trp Pro Gln Pro Glu Asp Phe Arg Ala Pro Gly Asp Asp Ile Val Arg
            180                 185                 190

Ser Thr Pro Val Glu Ile Asn Gly Gln Leu Gln Val Cys Gly Val Gln
            195                 200                 205

Leu Cys Asn Gln Tyr Gly Lys Pro Ile Gln Leu Arg Gly Met Ser Thr
210                 215                 220

His Gly Ile Gln Trp Phe Gly Asn Cys Val Asn Asn Ala Ser Leu Asp
225                 230                 235                 240

Ala Leu Ala Asn Asp Trp Arg Ala Asp Ile Phe Arg Ile Ala Met Tyr
                245                 250                 255

Ile Gln Glu Asp Gly Tyr Glu Thr Asn Pro Ala Gly Thr Asn Arg Val
            260                 265                 270

Asn Asn Leu Val Glu Glu Ala Thr Ala Arg Gly Met Tyr Val Leu Ile
            275                 280                 285

Asp Trp His Ile Leu Thr Pro Gly Asp Pro Asn Tyr Asn Leu Asp Arg
290                 295                 300

Ala Lys Thr Phe Phe Ala Glu Ile Ala Ala Arg His Ala Ser Lys Thr
305                 310                 315                 320

Asn Val Ile Tyr Glu Ile Ala Asn Glu Pro Asn Gly Gly Val Ser Trp
                325                 330                 335

Ser Asn Thr Ile Lys Ser Tyr Ala Glu Glu Val Ile Pro Val Ile Arg
            340                 345                 350

Ala Asn Asp Pro Asp Ser Val Val Ile Val Gly Thr Arg Gly Trp Ser
            355                 360                 365

Ser Asp Ser Thr Glu Ile Val Asn Asn Pro Val Asn Ala Ser Asn Ile
370                 375                 380

Met Tyr Ala Phe His Phe Tyr Ala Ala Ser His Arg Asp Asn Tyr Arg
385                 390                 395                 400

Asp Glu Val Glu Arg Ala Ala Ala Arg Gly Leu Pro Val Phe Val Thr
                405                 410                 415

Glu Phe Gly Thr Val Thr Tyr Thr Gly Asp Gly Asn Asp Leu Ala
            420                 425                 430

Ser Ser Gln Lys Trp Leu Asp Leu Leu Asp Ala Arg Lys Ile Gly Trp
            435                 440                 445

Ala Asn Trp Asn Phe Ser Asp Lys Ala Glu Ser Ser Ala Ala Leu Arg
450                 455                 460

Pro Gly Thr Cys Ala Gly Gly Ser Trp Thr Gly Thr Ser Leu Thr Pro
465                 470                 475                 480

Ser Gly Val Phe Val Arg Glu Arg Ile Arg
                485                 490

<210> SEQ ID NO 8
<211> LENGTH: 87
<212> TYPE: PRT
<213> ORGANISM: Artificial Sequence
<220> FEATURE:
```

<223> OTHER INFORMATION: Carbohydrate binding domain

<400> SEQUENCE: 8

Phe Thr Val Gln Trp Lys Lys Ser Ser Ser Trp Glu Glu Gly Gly Lys
1               5                   10                  15

Lys Cys Gly Gly Tyr Glu Ile Val Ile Thr Asn Asn Gly Asp Thr Val
            20                  25                  30

Asn Ser Trp Thr Ala Lys Val Thr Val Pro Gly Asn Thr Lys Leu Met
        35                  40                  45

Ser Gln Trp Asn Gly Ile Phe Ser Ile Ser Gly Asn Thr Met Thr Val
    50                  55                  60

Lys Asn Glu Ser Tyr Asn Gly Thr Ile Glu Lys Gly Lys Ser Ile Ser
65                  70                  75                  80

Phe Gly Phe Asn Tyr Ser Ala
                85

<210> SEQ ID NO 9
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 9

Tyr Gln Leu Lys Val Thr Val Ser Ser Ser Trp Glu Ser Gly Asp Gly
1               5                   10                  15

Tyr Gly Gly Thr Tyr Ser Leu Ser Phe Thr Asn Arg Ser Ala Ala Val
            20                  25                  30

Lys Ala Trp Asp Ala Gln Ile Glu Val Pro Glu Gly Ser Lys Val Thr
        35                  40                  45

Glu Ala Trp Gly Cys Glu Thr Gly Ile Asp Gly Thr Ile Leu Thr Val
    50                  55                  60

Thr Ala Lys Asp Trp Gly Ala Ala Val Ala Lys Gly Ser Thr Val Glu
65                  70                  75                  80

Ile Gly Phe Asn Met Asp Thr
                85

<210> SEQ ID NO 10
<211> LENGTH: 84
<212> TYPE: PRT
<213> ORGANISM: Artificial Sequence
<220> FEATURE:
<223> OTHER INFORMATION: Carbohydrate binding domain

<400> SEQUENCE: 10

Tyr Lys Ala Asp Phe Lys Val Val Asn Ser Trp Glu Glu Gly Gly Lys
1               5                   10                  15

Lys Cys Tyr Gln Leu Ser Gly Thr Leu Thr Asn Leu Ser Ser Ser Ile
            20                  25                  30

Ser Ser Trp Thr Val Val Phe Asp Ala Gly Asn Gly Ala Glu Ile Lys
        35                  40                  45

Gln Phe Trp Asn Ser Lys Cys Thr Ile Ser Gly Asn Lys Ile Thr Val
    50                  55                  60

Gly Pro Ala Asp Tyr Asn Ser Arg Ile Gly Thr Gly Ala Ser Val Ser
65                  70                  75                  80

Asp Val Gly Met

<210> SEQ ID NO 11

```
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 11

Phe Tyr Ala Glu Ile Gly His Asp Ser Thr Trp Glu Ala Ser Gly Lys
1               5                   10                  15

Thr Cys Ala Thr Glu Asn Ile Asn Ile Tyr Asn Lys Thr Ser Ser Val
            20                  25                  30

Ser Gly Trp Lys Leu Asp Val Ile Tyr Lys Gly Lys Pro Ala Ile Glu
        35                  40                  45

Asp Ile Trp Asn Gly Glu Lys Lys Ile Asn Glu Tyr Thr Val Ser Ile
    50                  55                  60

Thr Pro Ala Asp Tyr Asn Gln Asp Ile Pro Ala Gly Gly Ser Val Asn
65                  70                  75                  80

Val Gly Tyr Asn Ile Ala Ser
                85

<210> SEQ ID NO 12
<211> LENGTH: 87
<212> TYPE: PRT
<213> ORGANISM: Artificial Sequence
<220> FEATURE:
<223> OTHER INFORMATION: Carbohydrate binding domain

<400> SEQUENCE: 12

Tyr Tyr Ala Ser Ile Ser Asp Asn Ser Ser Trp Gln Glu Asn Gly Lys
1               5                   10                  15

Asn Ala Ala Thr Lys Asn Val Ile Ile Tyr Asn Lys Asp Lys Lys Val
            20                  25                  30

Thr Gly Trp Lys Ile Glu Leu Val Phe Ala Ser Glu Pro Glu Leu Ala
        35                  40                  45

Asp Ile Trp Gly Gly Lys Ala Glu Val Asn Gly Asp Thr Ile Thr Val
    50                  55                  60

Val Gly Tyr Asp Tyr Thr Ala Glu Leu Lys Ala Gly Gly Asn Val Asn
65                  70                  75                  80

Phe Gly Phe Asn Val Lys Ala
                85

<210> SEQ ID NO 13
<211> LENGTH: 77
<212> TYPE: PRT
<213> ORGANISM: Artificial Sequence
<220> FEATURE:
<223> OTHER INFORMATION: Carbohydrate binding domain

<400> SEQUENCE: 13

Trp Ala Glu Gln Asn Gln Thr Ala Phe Gln Tyr Glu Leu Leu Phe Ser
1               5                   10                  15

Asn Gln Ser Glu Ala Phe Gly Thr Trp Lys Val Ile Leu Asp Thr Gly
            20                  25                  30

Lys Glu Val Lys Val Gln Asn Ser Trp Asn Cys Ser Leu Glu Ala Asp
        35                  40                  45

Gly Asn Leu Leu Thr Phe Thr Pro Ala Asp Tyr Asn Ala Lys Leu Ala
    50                  55                  60

Lys Gly Ala Glu Met Ala Asp Val Gly Met Ile Leu Val
65                  70                  75
```

<210> SEQ ID NO 14
<211> LENGTH: 85
<212> TYPE: PRT
<213> ORGANISM: Artificial Sequence
<220> FEATURE:
<223> OTHER INFORMATION: Carbohydrate binding domain

<400> SEQUENCE: 14

```
Met Gln Phe Lys Gln Ser Asn Ser Trp Glu Gly Asn Gly Arg Phe Tyr
1               5                   10                  15

Ala Gln Tyr Asp Leu Ile Ile Asp Asn Lys Glu Asp Val Ile Ser Asp
                20                  25                  30

Trp Thr Phe Lys Ile Asn Thr Thr Asn Gly Thr Thr Leu Glu Gln Ser
            35                  40                  45

Trp Asn Cys Thr Val Asp Thr Ser Asp Leu Gln Trp Ser Val Val Pro
        50                  55                  60

Val Asp Tyr Asn Lys Ile Ile Glu Ser Gln Ala Gln Met Asn Asn Val
65                  70                  75                  80

Gly Phe Ile Ile Ser
                85
```

<210> SEQ ID NO 15
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 15

```
Asn Gly Ile Ser Val Gln Tyr Arg Ala Gly Asp Gly Ser Met Asn Ser
1               5                   10                  15

Asn Gln Ile Arg Pro Gln Leu Gln Ile Lys Asn Asn Gly Asn Thr Thr
                20                  25                  30

Val Asp Leu Lys Asp Val Thr Ala Arg Tyr Trp Tyr Asn Ala Lys Asn
            35                  40                  45

Lys Gly Gln Asn Val Asp Cys Asp Tyr Ala Gln Leu Gly Cys Gly Asn
        50                  55                  60

Val Thr Tyr Lys Phe Val Thr Leu His Lys Pro Lys Gln Gly Ala Asp
65                  70                  75                  80

Thr Tyr Leu Glu Leu Gly Phe Lys Asn Gly Thr Leu Ala Pro Gly Ala
                85                  90                  95

Ser Thr Gly Asn Ile Gln Leu Arg Leu His Asn Asp Asp Trp Ser Asn
                100                 105                 110

Tyr Ala Gln Ser Gly Asp Tyr Ser Phe Phe Lys Ser Asn Thr Phe Lys
            115                 120                 125

Thr Thr Lys Lys Ile Thr Leu Tyr Asp Gln Gly Lys Leu Ile Trp Gly
        130                 135                 140

Thr Glu Pro
145
```

<210> SEQ ID NO 16
<211> LENGTH: 137
<212> TYPE: PRT
<213> ORGANISM: Artificial Sequence
<220> FEATURE:
<223> OTHER INFORMATION: Carbohydrate binding domain

<400> SEQUENCE: 16

```
Asn Gly Ile Ser Val Gln Tyr Arg Ala Gly Asp Gly Ser Met Asn Ser
```

```
                1               5                  10                  15
Asn Gln Ile Arg Pro Gln Leu Gln Ile Lys Asn Asn Gly Asn Thr Thr
                20                  25                  30

Val Asp Leu Lys Asp Val Thr Ala Arg Tyr Trp Tyr Lys Ala Lys Asn
                35                  40                  45

Lys Gly Gln Asn Val Asp Cys Asp Tyr Ala Gln Ile Gly Cys Gly Asn
                50                  55                  60

Val Thr Tyr Lys Phe Val Thr Leu His Lys Pro Lys Gln Gly Ala Asp
 65                 70                  75                  80

Thr Tyr Leu Glu Leu Gly Phe Lys Asn Gly Thr Leu Ala Pro Gly Ala
                85                  90                  95

Ser Thr Gly Asn Ile Gln Leu Arg Leu His Asn Asp Asp Trp Ser Asn
                100                 105                 110

Tyr Ala Gln Ser Gly Asp Tyr Ser Phe Phe Lys Ser Asn Thr Phe Lys
                115                 120                 125

Thr Thr Lys Lys Ile Thr Leu Tyr Asp
                130                 135
```

<210> SEQ ID NO 17
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 17

```
Asn Gly Ile Ser Val Gln Tyr Lys Ala Gly Asp Gly Val Asn Ser
 1               5                  10                  15

Asn Gln Ile Arg Pro Gln Leu His Ile Lys Asn Asn Gly Asn Ala Thr
                20                  25                  30

Val Asp Leu Lys Asp Val Thr Ala Arg Tyr Trp Tyr Asn Ala Lys Asn
                35                  40                  45

Lys Gly Gln Asn Phe Asp Cys Asp Tyr Ala Gln Ile Gly Cys Gly Asn
                50                  55                  60

Leu Thr His Lys Phe Val Thr Leu His Lys Pro Lys Gln Gly Ala Asp
 65                 70                  75                  80

Thr Tyr Leu Glu Leu Gly Phe Lys Thr Gly Thr Leu Ser Pro Gly Ala
                85                  90                  95

Ser Thr Gly Asn Ile Gln Leu Arg Leu His Asn Asp Asp Trp Ser Asn
                100                 105                 110

Tyr Ala Gln Ser Asp Asp Tyr Ser Phe Phe Gln Ser Asn Thr Phe Lys
                115                 120                 125

Thr Thr Lys Lys Ile Thr Leu Tyr His Gln Gly Lys Leu Ile Trp Gly
                130                 135                 140

Thr Glu Pro
145
```

<210> SEQ ID NO 18
<211> LENGTH: 63
<212> TYPE: PRT
<213> ORGANISM: Artificial Sequence
<220> FEATURE:
<223> OTHER INFORMATION: Carbohydrate binding domain

<400> SEQUENCE: 18

```
Pro Gly Glu Pro Glu Pro Asp Pro Gly Glu Pro Asp Pro Thr Pro Pro
 1               5                  10                  15
```

```
Ser Asp Gly Asp Tyr Pro Ala Trp Asp Pro Asn Thr Ile Tyr Thr Asp
            20                  25                  30

Glu Ile Val Tyr His Asn Gly Gln Leu Trp Gln Ala Lys Trp Trp Thr
         35                  40                  45

Gln Asn Gln Glu Pro Gly Asp Tyr Gly Pro Trp Glu Pro Leu Asn
     50                  55                  60

<210> SEQ ID NO 19
<211> LENGTH: 145
<212> TYPE: PRT
<213> ORGANISM: Artificial Sequence
<220> FEATURE:
<223> OTHER INFORMATION: Carbohydrate binding domain

<400> SEQUENCE: 19

Gly Asn Leu Val Val Gln Tyr Lys Val Gly Asp Thr Ser Ala Thr Asp
1               5                   10                  15

Asn Gln Met Lys Pro Ser Phe Asn Ile Lys Asn Asn Gly Thr Thr Pro
            20                  25                  30

Val Asn Leu Ser Gly Leu Lys Leu Arg Tyr Tyr Phe Thr Lys Asp Gly
         35                  40                  45

Thr Asp Met Ser Ala Ser Ile Asp Trp Ala Gln Ile Gly Ala Ser Asn
 50                  55                  60

Ile Ser Ala Ala Phe Ala Asp Phe Thr Gly Ser Asn Thr Asp Thr Tyr
65                  70                  75                  80

Val Glu Leu Ser Phe Ser Ala Gly Ser Ile Pro Ala Gly Gly Gln Thr
                85                  90                  95

Gly Asp Ile Gln Leu Arg Met Tyr Lys Thr Asp Trp Ser Asn Phe Asn
            100                 105                 110

Glu Ala Asn Asp Tyr Ser Tyr Asp Gly Ala Lys Thr Tyr Ala Asp Trp
        115                 120                 125

Asn Arg Val Thr Leu His Gln Asn Gly Thr Leu Val Trp Gly Thr Thr
    130                 135                 140

Pro
145

<210> SEQ ID NO 20
<211> LENGTH: 57
<212> TYPE: PRT
<213> ORGANISM: Artificial Sequence
<220> FEATURE:
<223> OTHER INFORMATION: Carbohydrate binding domain

<400> SEQUENCE: 20

Asp Pro Gly Glu Pro Asp Pro Thr Pro Pro Ser Asp Gly Glu Tyr Pro
1               5                   10                  15

Ala Trp Asp Pro Asn Gln Ile Tyr Thr Asn Glu Ile Val Tyr His Asn
            20                  25                  30

Gly Gln Leu Trp Gln Ala Lys Trp Trp Thr Gln Asn Gln Glu Pro Gly
         35                  40                  45

Asp Tyr Gly Pro Trp Glu Pro Leu Asn
     50                  55

<210> SEQ ID NO 21
<211> LENGTH: 144
<212> TYPE: PRT
<213> ORGANISM: Artificial Sequence
<220> FEATURE:
<223> OTHER INFORMATION: Carbohydrate binding domain
```

```
<400> SEQUENCE: 21

Gly Ser Leu Val Leu Gln Tyr Arg Ala Ala Asp Thr Asn Ala Gly Asp
1               5                   10                  15

Asn Ala Ile Lys Pro His Phe Asn Ile Arg Asn Thr Gly Ala Ser Pro
            20                  25                  30

Val Asp Leu Ser Gly Val Lys Leu Arg Tyr Tyr Phe Thr Lys Asp Gly
        35                  40                  45

Ile Pro Leu Ser Phe Ala Val Asp Trp Ala Gln Val Gly Ser Pro Asn
    50                  55                  60

Val Lys Gly Thr Phe Gly Ser Ala Ser Gly Ala Gly Ala Asp Thr Tyr
65                  70                  75                  80

Leu Glu Val Ser Phe Thr Gly Ser Ile Pro Ala Gly Gln Thr Gly
                85                  90                  95

Glu Ile Gln Thr Arg Ile His Lys Ser Asp Trp Ser Ser Phe Gln Glu
                100                 105                 110

Ser Gly Asp Tyr Ser Tyr Asp Pro Gly Lys Thr Tyr Ala Asp Trp Ser
                115                 120                 125

Lys Val Thr Leu Tyr Arg Asp Gly Thr Arg Val Trp Gly Val Glu Pro
130                 135                 140

<210> SEQ ID NO 22
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 22

Asn Ile Thr Ser Ala Val Tyr Thr Ile Ser Asn Thr Asp Pro Val Lys
1               5                   10                  15

Gln Val Ser Ala Pro Thr Phe Ser Leu Gln Ser Ala Gln Thr Val Thr
            20                  25                  30

Leu Thr Ser Ser Asp Asn Asp Ser Val Ile His Tyr Thr Thr Asp Gly
        35                  40                  45

Thr Pro Thr Ser Ser Pro Val Tyr Thr Asn Met Thr Asp Ser Ser
    50                  55                  60

Val Val Thr Asn Thr Tyr Thr Ile Thr Asn Glu Thr Ser Asn Ser Pro
65                  70                  75                  80

Val Glu Val Glu Val Glu Tyr Lys Thr Thr Val Lys Val Thr Leu Thr
                85                  90                  95

Asn Asn Ser Ser Thr Pro Ile Asn Gly Trp Lys Leu Ser Trp Ile Asn
                100                 105                 110

Asn Met Trp Thr Ala Asn Tyr Ser Ile Lys Asp Ser Ala Ile Val Lys
                115                 120                 125

Asp Tyr Asn Asn Ile Ile Pro Ala Asn Gly Gly Thr Gln Ile Phe Gly
130                 135                 140

Phe Ser Ile
145

<210> SEQ ID NO 23
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 23
```

```
Gln Gly Ile Val Leu Gln Tyr Arg Thr Gly Asp Thr Asn Thr Lys Asp
1               5                   10                  15

Asn Ala Ile Arg Pro Glu Phe Asn Ile Lys Asn Thr Gly Asn Thr Ala
            20                  25                  30

Val Lys Leu Ser Asp Leu Lys Ile Arg Tyr Tyr Tyr Thr Asp Glu Ser
        35                  40                  45

Lys Gly Gln Gln Leu Phe Val Asp Trp Ala Lys Val Gly Asn Glu Lys
    50                  55                  60

Val Lys Ala Thr Phe Val Ala Leu Pro Glu Pro Lys Ala Lys Ala Asp
65                  70                  75                  80

Lys Tyr Val Glu Ile Ser Phe Thr Asp Gly Thr Ile Gln Pro Gly Gly
                85                  90                  95

Glu Ser Gly Glu Ile Gln Pro Arg Ile His Ala Ala Asn Trp Ser Asn
                100                 105                 110

Phe Asp Glu Thr Asn Asp Tyr Ser Tyr Gly Ala Ser Gln Thr Phe Ala
            115                 120                 125

Asn Trp Asp His Ala Thr Val Tyr Gln Gln Gly Lys Leu Val Trp Gly
        130                 135                 140

Ile Glu Pro
145

<210> SEQ ID NO 24
<211> LENGTH: 147
<212> TYPE: PRT
<213> ORGANISM: Artificial Sequence
<220> FEATURE:
<223> OTHER INFORMATION: Carbohydrate binding domain

<400> SEQUENCE: 24

Glu Gly Ile Val Leu Gln Tyr Arg Thr Asp Asp Thr Asn Ala Lys Asp
1               5                   10                  15

Asn Ala Ile Arg Pro Gln Phe Asn Ile Lys Asn Thr Gly Lys Thr Ala
            20                  25                  30

Val Lys Leu Ser Asp Leu Lys Ile Arg Tyr Tyr Tyr Thr Asp Glu Ser
        35                  40                  45

Lys Ala Gln Gln Phe Phe Val Asp Trp Ala Lys Ile Gly Asn Glu Lys
    50                  55                  60

Val Lys Ala Thr Phe Val Thr Leu Pro Asn Pro Lys Ser Lys Ala Asp
65                  70                  75                  80

Lys Tyr Val Glu Ile Ser Phe Thr Asp Gly Thr Ile Gln Pro Gly Gly
                85                  90                  95

Glu Thr Gly Glu Ile Gln Ser Arg Ile His Ala Ala Asn Trp Ser Asn
                100                 105                 110

Phe Asp Glu Thr Asn Asp Tyr Ser Tyr Gly Ala Ala Gln Thr Phe Ala
            115                 120                 125

Asp Trp Asp His Gly Thr Val Tyr Gln Gln Gly Lys Leu Val Trp Gly
        130                 135                 140

Ile Glu Pro
145

<210> SEQ ID NO 25
<211> LENGTH: 107
<212> TYPE: PRT
<213> ORGANISM: Artificial Sequence
<220> FEATURE:
<223> OTHER INFORMATION: Carbohydrate binding domain

<400> SEQUENCE: 25
```

```
Gln Ala Ala Gly Leu Thr Ala Thr Val Thr Lys Glu Ser Ser Trp Asp
1               5                   10                  15

Asn Gly Tyr Ser Ala Ser Val Thr Val Arg Asn Asp Thr Ser Ser Val
            20                  25                  30

Ser Gln Trp Glu Val Val Leu Thr Leu Pro Gly Gly Thr Thr Val Ala
        35                  40                  45

Gln Val Trp Asn Ala Gln His Thr Ser Ser Gly Asn Ser His Thr Phe
    50                  55                  60

Thr Gly Val Ser Trp Asn Ser Thr Ile Pro Pro Gly Thr Ala Ser
65                  70                  75                  80

Phe Gly Phe Ile Ala Ser Gly Ser Gly Glu Pro Thr His Cys Thr Ile
                85                  90                  95

Asn Gly Ala Pro Cys Asp Glu Gly Ser Glu Pro
            100                 105

<210> SEQ ID NO 26
<211> LENGTH: 106
<212> TYPE: PRT
<213> ORGANISM: Artificial Sequence
<220> FEATURE:
<223> OTHER INFORMATION: Carbohydrate binding domain

<400> SEQUENCE: 26

Ala Ala Thr Gly Cys Ser Val Thr Tyr Thr Thr Asn Ser Trp Ser Asn
1               5                   10                  15

Gly Phe Thr Ala Asn Val Thr Val Thr Asn Leu Gly Asp Ala Ile Gly
            20                  25                  30

Asn Trp Thr Leu Gly Phe Ser Phe Pro Ser Gly Gln Arg Val Thr Gln
        35                  40                  45

Gly Trp Ser Ala Ile Trp Ser Gln Ser Gly Asn Ala Val Thr Ala Arg
    50                  55                  60

Ser Glu Ser Trp Asn Gly Asn Leu Ala Thr Gly Ala Ser Thr Ser Ile
65                  70                  75                  80

Gly Phe Asn Gly Ser Phe Thr Gly Ser Pro Thr Ser Phe Thr Leu Asn
                85                  90                  95

Gly Val Pro Cys Thr Gly Ser Thr Thr Thr
            100                 105

<210> SEQ ID NO 27
<211> LENGTH: 103
<212> TYPE: PRT
<213> ORGANISM: Artificial Sequence
<220> FEATURE:
<223> OTHER INFORMATION: Carbohydrate binding domain

<400> SEQUENCE: 27

Glu Ala Ala Ser Phe Thr Val Thr Asn Ser Trp Ser Thr Gly Tyr Gln
1               5                   10                  15

Gly Glu Val Thr Val Ser Asn Pro Ala Ser Ser Ile Asn Thr Trp Lys
            20                  25                  30

Val Gln Leu Thr Leu Pro Ala Gly Ser Thr Ile Gly Gln Ala Trp Asn
        35                  40                  45

Ala Thr Leu Ala Thr Gly Gly Gln Thr Phe Thr Phe Thr Pro Ala Gly
    50                  55                  60

Trp Asn Gly Thr Ile Ala Gly Gly Ser Ala Thr Ser Phe Gly Phe Val
65                  70                  75                  80

Val Thr Gly Thr Gly Arg Pro Thr Ser Cys Thr Val Asn Gly Gln Ala
```

```
                    85                  90                  95

Cys Thr Gly Leu Thr Gly Ala
                100

<210> SEQ ID NO 28
<211> LENGTH: 107
<212> TYPE: PRT
<213> ORGANISM: Artificial Sequence
<220> FEATURE:
<223> OTHER INFORMATION: Carbohydrate binding domain

<400> SEQUENCE: 28

Ala Ala Thr Gly Cys His Val Asp Tyr Thr Val Thr Asn Gln Trp Gln
1               5                   10                  15

Gly Gly Phe Gln Ala Ala Val Lys Val Thr Asn Leu Gly Asp Ala Ile
            20                  25                  30

Thr Gly Trp Leu Leu Arg Phe Thr Phe Pro Ala Gly Gln Lys Val Ala
        35                  40                  45

Gln Gly Trp Asn Ala Thr Trp Ala Gln Ser Gly Ala Thr Ala Thr Ala
    50                  55                  60

Ala Asn Ala Asp Trp Asn Arg Thr Leu Thr Thr Gly Ala Thr Thr Glu
65                  70                  75                  80

Leu Gly Phe Thr Gly Thr Thr Thr Gly Val Pro Ala Ser Phe Thr Leu
                85                  90                  95

Asn Gly Val Thr Cys Thr Gly Ser Thr Thr Thr
                100                 105

<210> SEQ ID NO 29
<211> LENGTH: 106
<212> TYPE: PRT
<213> ORGANISM: Artificial Sequence
<220> FEATURE:
<223> OTHER INFORMATION: Carbohydrate binding domain

<400> SEQUENCE: 29

Ala Ala Thr Gly Cys Ala Val Thr Tyr Thr Thr Asn Ser Trp Gln Gly
1               5                   10                  15

Gly Phe Thr Ala Thr Val Ala Val Arg Asn Leu Gly Asp Pro Val Ser
            20                  25                  30

Asn Trp Thr Leu Gly Phe Thr Phe Pro Gly Gly Gln Arg Val Val Gln
        35                  40                  45

Gly Trp Ser Ala Thr Trp Gln Gln Ser Gly Ser Ala Val Thr Ala Arg
    50                  55                  60

Ser Leu Asp Tyr Asn Gly Ala Leu Gly Thr Gly Ala Ser Thr Thr Ile
65                  70                  75                  80

Gly Phe Asn Gly Ser Trp Thr Gly Ser Pro Thr Ser Phe Thr Leu Asn
                85                  90                  95

Gly Thr Val Cys Thr Gly Gly Thr Ser Thr
                100                 105

<210> SEQ ID NO 30
<211> LENGTH: 106
<212> TYPE: PRT
<213> ORGANISM: Artificial Sequence
<220> FEATURE:
<223> OTHER INFORMATION: Carbohydrate binding domain

<400> SEQUENCE: 30

Ala Ala Thr Gly Cys Ala Val Thr Tyr Thr Thr Asn Ser Trp Gln Gly
1               5                   10                  15
```

Gly Phe Thr Ala Thr Val Ala Val Arg Asn Leu Gly Asp Pro Val Ser
            20                  25                  30

Asn Trp Thr Leu Gly Phe Thr Phe Pro Gly Gly Gln Arg Val Val Gln
        35                  40                  45

Gly Trp Ser Ala Thr Trp Gln Gln Ser Gly Ser Ala Val Thr Ala Arg
    50                  55                  60

Ser Leu Asp Tyr Asn Gly Ala Leu Gly Thr Gly Ala Ser Thr Thr Ile
65                  70                  75                  80

Gly Phe Asn Gly Ser Trp Thr Gly Ser Pro Thr Ser Phe Thr Leu Asn
                85                  90                  95

Gly Thr Val Cys Thr Gly Gly Thr Ser Thr
            100                 105

<210> SEQ ID NO 31
<211> LENGTH: 100
<212> TYPE: PRT
<213> ORGANISM: Artificial Sequence
<220> FEATURE:
<223> OTHER INFORMATION: Carbohydrate binding domain

<400> SEQUENCE: 31

Glu Ser Glu Asn Ala Thr Ile Ser Arg Gly Val Val Glu Ala Asn His
1               5                   10                  15

Thr Gly Phe Thr Gly Ser Gly Phe Val Asn Tyr Asp Asn Val Thr Gly
            20                  25                  30

Ser Tyr Val Glu Tyr Thr Val Asn Ala Ala Gln Ala Gly Pro His Thr
        35                  40                  45

Leu Thr Phe Arg Tyr Ala Asn Gly Thr Thr Ala Asn Arg Pro Leu Asp
    50                  55                  60

Ile Thr Val Asn Gly Ser Ile Ala Val Asp Asp Leu Gly Phe Ala Gly
65                  70                  75                  80

Thr Gly Ala Trp Ser Thr Val Thr Thr Val Asn Leu Ala Ala Gly
                85                  90                  95

Ser Asn Lys Ile
            100

<210> SEQ ID NO 32
<211> LENGTH: 107
<212> TYPE: PRT
<213> ORGANISM: Artificial Sequence
<220> FEATURE:
<223> OTHER INFORMATION: Carbohydrate binding domain

<400> SEQUENCE: 32

Asn Ala Ala Gly Cys Arg Val Asp Tyr Thr Val Thr Asn Gln Trp Gln
1               5                   10                  15

Gly Gly Phe Gln Ala Gly Val Lys Ile Thr Asn Leu Gly Asp Thr Val
            20                  25                  30

Arg Gly Trp Thr Leu Lys Phe Thr Leu Pro Thr Gly Gln Lys Val Val
        35                  40                  45

Gln Gly Trp Ser Ala Ala Trp Ser Gln Ser Gly Ser Thr Val Thr Val
    50                  55                  60

Ala Gly Ala Asp Trp Asn Gly Thr Leu Ala Thr Gly Ala Ser Ala Asp
65                  70                  75                  80

Thr Gly Phe Val Gly Ser Phe Thr Gly Lys Pro Thr Ala Phe Thr Leu
                85                  90                  95

Asn Gly Val Ala Cys Thr Gly Ser Val Asp Asp 100                 105

<210> SEQ ID NO 33
<211> LENGTH: 105
<212> TYPE: PRT
<213> ORGANISM: Artificial Sequence
<220> FEATURE:
<223> OTHER INFORMATION: Carbohydrate binding domain

<400> SEQUENCE: 33

Ala Ala Thr Gly Cys Lys Ala Glu Tyr Thr Ile Thr Ser Gln Trp Glu
1               5                   10                  15

Gly Gly Phe Gln Ala Gly Val Lys Ile Thr Asn Leu Gly Asp Pro Val
            20                  25                  30

Ser Gly Trp Thr Leu Gly Phe Thr Met Pro Ala Gly Gln Arg Leu Val
        35                  40                  45

Gln Gly Trp Asn Ala Thr Trp Ser Gln Ser Gly Ser Ala Val Thr Ala
    50                  55                  60

Gly Gly Val Asp Trp Asn Arg Thr Leu Ala Thr Gly Ala Ser Ala Asp
65                  70                  75                  80

Leu Gly Phe Val Gly Ser Phe Thr Gly Ala Pro Thr Ser Phe Thr Leu
                85                  90                  95

Asn Gly Ala Thr Cys Ser Gly Ser Val
            100                 105

<210> SEQ ID NO 34
<211> LENGTH: 81
<212> TYPE: PRT
<213> ORGANISM: Artificial Sequence
<220> FEATURE:
<223> OTHER INFORMATION: Carbohydrate binding domain

<400> SEQUENCE: 34

Asp Gly Ile Gln Thr Glu Ser Thr Thr Asp Thr Gly Gly Gly Leu Asn
1               5                   10                  15

Ile Gly Trp Thr Asp Ala Gly Asp Trp Thr Ser Pro Ala Ala Gly Arg
            20                  25                  30

Tyr Lys Val Ser Tyr Arg Asn Ser Gly Met Leu Gln Leu Glu Ala Ala
        35                  40                  45

Gly Gly Phe Pro Thr Tyr Gly Ser Ile Thr Gly Gly Trp Gln Ser Trp
    50                  55                  60

Gln Thr Ile Ser His Glu Val Asn Leu Asn Trp Ile Lys Val Glu Pro
65                  70                  75                  80

Ala

<210> SEQ ID NO 35
<211> LENGTH: 81
<212> TYPE: PRT
<213> ORGANISM: Artificial Sequence
<220> FEATURE:
<223> OTHER INFORMATION: Carbohydrate binding domain

<400> SEQUENCE: 35

Pro Thr Glu Pro Thr Asn Pro Gly Asn Gly Thr Thr Gly Asp Val Val
1               5                   10                  15

Leu Gln Tyr Arg Asn Val Asp Asn Asn Pro Ser Asp Asp Ala Ile Arg
            20                  25                  30

Met Ala Val Asn Ile Lys Asn Thr Gly Ser Thr Pro Ile Lys Leu Ser
        35                  40                  45

```
Asp Leu Gln Val Arg Tyr Tyr Phe His Asp Asp Gly Lys Pro Gly Ala
 50                  55                  60

Asn Leu Phe Val Asp Trp Ala Asn Val Gly Pro Asn Asn Ile Val Thr
 65                  70                  75                  80

Ser
```

<210> SEQ ID NO 36
<211> LENGTH: 81
<212> TYPE: PRT
<213> ORGANISM: Artificial Sequence
<220> FEATURE:
<223> OTHER INFORMATION: Carbohydrate binding domain

<400> SEQUENCE: 36

```
Pro Thr Glu Pro Thr Asn Pro Gly Asn Gly Thr Thr Gly Asp Ile Val
  1               5                  10                  15

Leu Gln Tyr Arg Asn Val Asp Asn Asn Pro Ser Asp Asp Ala Ile Arg
                 20                  25                  30

Met Ala Phe Asn Ile Lys Asn Thr Gly Ser Thr Pro Ile Lys Leu Ser
             35                  40                  45

Asp Leu Gln Val Arg Tyr Tyr Phe His Asp Asp Gly Lys Pro Gly Ala
 50                  55                  60

Asn Leu Phe Val Asp Trp Ala Asn Val Gly Pro Asn Asn Ile Val Thr
 65                  70                  75                  80

Ser
```

<210> SEQ ID NO 37
<211> LENGTH: 78
<212> TYPE: PRT
<213> ORGANISM: Artificial Sequence
<220> FEATURE:
<223> OTHER INFORMATION: Carbohydrate binding domain

<400> SEQUENCE: 37

```
Ser Ser Ser Ser Ala Val Ser Ser Gln Thr Gln Val Ser Ser Ser Ser
  1               5                  10                  15

Gln Ala Pro Val Val Ser Ser Ser Ser Thr Ala Ser Ser Val Val
                 20                  25                  30

Ser Ser Ala Val Ser Gly Tyr Gly Thr Leu Tyr Pro Leu Cys Ser Thr
             35                  40                  45

Thr Thr Asn Gly Trp Gly Trp Glu Asn Asn Ala Ser Cys Ile Ala Arg
 50                  55                  60

Ala Thr Cys Ser Gly Gln Pro Ser Ser Ser Val Arg Ser Ser
 65                  70                  75
```

<210> SEQ ID NO 38
<211> LENGTH: 135
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 38

```
Phe Thr Val Gln Trp Lys Lys Ser Ser Ser Trp Glu Glu Gly Gly Lys
  1               5                  10                  15

Lys Cys Gly Gly Tyr Glu Ile Val Ile Thr Asn Asn Gly Asp Thr Val
                 20                  25                  30

Asn Ser Trp Thr Ala Lys Val Thr Val Pro Gly Asn Thr Lys Leu Met
             35                  40                  45
```

```
Ser Gln Trp Asn Gly Ile Phe Ser Ile Ser Gly Asn Thr Met Thr Val
    50                  55                  60

Lys Asn Glu Ser Tyr Asn Gly Thr Ile Glu Lys Gly Lys Ser Ile Ser
 65                  70                  75                  80

Phe Gly Phe Asn Tyr Ser Ala Asp Ala Tyr Ile Asn Glu Gly Lys Val
                 85                  90                  95

Gly Ser Thr Ala Gly Thr Ser Ala Gly Asn Asn Ser Asn Asn Asn Asn
            100                 105                 110

Asn Asn Asn Asn Asn Thr Ser Thr Lys Lys Pro Ala Ala Thr Val
        115                 120                 125

Pro Pro Ala Pro Gly Thr Thr
        130                 135

<210> SEQ ID NO 39
<211> LENGTH: 129
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 39

Tyr Gln Leu Lys Val Thr Val Ser Ser Ser Trp Glu Ser Gly Asp Gly
 1               5                  10                  15

Tyr Gly Gly Thr Tyr Ser Leu Ser Phe Thr Asn Arg Ser Ala Ala Val
                20                  25                  30

Lys Ala Trp Asp Ala Gln Ile Glu Val Pro Glu Gly Ser Lys Val Thr
            35                  40                  45

Glu Ala Trp Gly Cys Glu Thr Gly Ile Asp Gly Thr Ile Leu Thr Val
 50                  55                  60

Thr Ala Lys Asp Trp Gly Ala Ala Val Ala Lys Gly Ser Thr Val Glu
 65                  70                  75                  80

Ile Gly Phe Asn Met Asp Thr Pro Glu Lys Leu Gln Pro Ser Ile Gln
                 85                  90                  95

Ser Phe Thr Val Asp Gly Lys Lys Gln Asp Gly Ser Gln Ala Glu Asp
            100                 105                 110

Thr Glu Glu Lys Thr Thr Glu Ala Val Thr Glu Ala Glu Lys Ser Gly
        115                 120                 125

Thr

<210> SEQ ID NO 40
<211> LENGTH: 131
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 40

Tyr Lys Ala Asp Phe Lys Val Val Asn Ser Trp Glu Glu Gly Gly Lys
 1               5                  10                  15

Lys Cys Tyr Gln Leu Ser Gly Thr Leu Thr Asn Leu Ser Ser Ser Ile
                20                  25                  30

Ser Ser Trp Thr Val Val Phe Asp Ala Gly Asn Gly Ala Glu Ile Lys
            35                  40                  45

Gln Phe Trp Asn Ser Lys Cys Thr Ile Ser Gly Asn Lys Ile Thr Val
 50                  55                  60
```

Gly Pro Ala Asp Tyr Asn Ser Arg Ile Gly Thr Gly Ala Ser Val Ser
65                  70                  75                  80

Asp Val Gly Met Ile Ile Ala Thr Ser Ser Ala Ile Ser Asp Phe Thr
                85                  90                  95

Tyr Asn Gly Glu Ala Ile Ala Ser Gly Gln Asp Thr Gly Asn Gly Gly
            100                 105                 110

Asn Gln Thr Thr Glu Asp Val Lys Pro Tyr Thr Pro Pro Lys Leu Glu
        115                 120                 125

Ser Gly Thr
    130

<210> SEQ ID NO 41
<211> LENGTH: 133
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 41

Phe Tyr Ala Glu Ile Gly His Asp Ser Thr Trp Glu Ala Ser Gly Lys
1               5                   10                  15

Thr Cys Ala Thr Glu Asn Ile Asn Ile Tyr Asn Lys Thr Ser Ser Val
            20                  25                  30

Ser Gly Trp Lys Leu Asp Val Ile Tyr Lys Gly Lys Pro Ala Ile Glu
        35                  40                  45

Asp Ile Trp Asn Gly Glu Lys Lys Ile Asn Glu Tyr Thr Val Ser Ile
    50                  55                  60

Thr Pro Ala Asp Tyr Asn Gln Asp Ile Pro Ala Gly Gly Ser Val Asn
65                  70                  75                  80

Val Gly Tyr Asn Ile Ala Ser Asp Leu Thr Val Val Asp Tyr Ile
                85                  90                  95

Leu Tyr Ile Asp Gly Lys Glu Tyr Arg Gly Ser Glu Asn Leu Ser Ala
            100                 105                 110

Asp Thr Ser Gly Thr Gly Gly Val Ala Glu Ser Asp Thr Lys Lys Thr
        115                 120                 125

Ala Glu Asp Gly Thr
    130

<210> SEQ ID NO 42
<211> LENGTH: 119
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 42

Tyr Tyr Ala Ser Ile Ser Asp Asn Ser Ser Trp Gln Glu Asn Gly Lys
1               5                   10                  15

Asn Ala Ala Thr Lys Asn Val Ile Tyr Asn Lys Asp Lys Lys Val
            20                  25                  30

Thr Gly Trp Lys Ile Glu Leu Val Phe Ala Ser Glu Pro Glu Leu Ala
        35                  40                  45

Asp Ile Trp Gly Gly Lys Ala Glu Val Asn Gly Asp Thr Ile Thr Val
    50                  55                  60

Val Gly Tyr Asp Tyr Thr Ala Glu Leu Lys Ala Gly Gly Asn Val Asn
65                  70                  75                  80

```
Phe Gly Phe Asn Val Lys Ala Asp Asp Val Thr Val Lys Asp Tyr Arg
                85                  90                  95

Leu Tyr Ile Asn Gly Glu Ala Glu Ala Glu Ser Lys Lys Lys
            100                 105                 110

Pro Glu Pro Glu Ser Gly Thr
        115

<210> SEQ ID NO 43
<211> LENGTH: 125
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 43

Trp Ala Glu Gln Asn Gln Thr Ala Phe Gln Tyr Glu Leu Leu Phe Ser
1               5                   10                  15

Asn Gln Ser Glu Ala Phe Gly Thr Trp Lys Val Ile Leu Asp Thr Gly
            20                  25                  30

Lys Glu Val Lys Val Gln Asn Ser Trp Asn Cys Ser Leu Glu Ala Asp
        35                  40                  45

Gly Asn Leu Leu Thr Phe Thr Pro Ala Asp Tyr Asn Ala Lys Leu Ala
    50                  55                  60

Lys Gly Ala Glu Met Ala Asp Val Gly Met Ile Leu Val Ala Asp Ser
65                  70                  75                  80

Glu Pro Asp Ile Glu Gly Leu Asn Pro Asn Thr Gly Glu Leu Ala Pro
                85                  90                  95

Ala Asp Gly Arg Ser Ser Ala Ser Glu Gly Asp Lys Lys Glu Glu
            100                 105                 110

Glu Lys Lys Glu Ala Ala Ala Glu Val Ala Ser Gly Thr
        115                 120                 125

<210> SEQ ID NO 44
<211> LENGTH: 133
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 44

Met Gln Phe Lys Gln Ser Asn Ser Trp Glu Gly Asn Gly Arg Phe Tyr
1               5                   10                  15

Ala Gln Tyr Asp Leu Ile Ile Asp Asn Lys Glu Asp Val Ile Ser Asp
            20                  25                  30

Trp Thr Phe Lys Ile Asn Thr Thr Asn Gly Thr Thr Leu Glu Gln Ser
        35                  40                  45

Trp Asn Cys Thr Val Asp Thr Ser Asp Leu Gln Trp Ser Val Val Pro
    50                  55                  60

Val Asp Tyr Asn Lys Ile Ile Glu Ser Gln Ala Gln Met Asn Asn Val
65                  70                  75                  80

Gly Phe Ile Ile Ser Phe Ala Ser Lys Glu Glu Leu Lys Lys Asp Phe
                85                  90                  95

Lys Leu Glu Ser Gly Met Glu Ile Val Leu Ala Asp Gly Lys Ala
            100                 105                 110

Tyr Lys Asp Ser Gly Asn Asp Ser Gly Asn Asn Ser Asp Thr Gly Ser
        115                 120                 125
```

```
Asn Ala Gly Ile Val
    130

<210> SEQ ID NO 45
<211> LENGTH: 169
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 45

Ile Leu Gly Thr Lys Asp Ser Thr Lys Asp Ile Pro Glu Thr Pro Ala
1               5                   10                  15

Lys Asp Lys Pro Thr Gln Glu Asn Gly Ile Ser Val Gln Tyr Arg Ala
                20                  25                  30

Gly Asp Gly Ser Met Asn Ser Asn Gln Ile Arg Pro Gln Leu Gln Ile
            35                  40                  45

Lys Asn Asn Gly Asn Thr Thr Val Asp Leu Lys Asp Val Thr Ala Arg
    50                  55                  60

Tyr Trp Tyr Asn Ala Lys Asn Lys Gly Gln Asn Val Asp Cys Asp Tyr
65              70                  75                  80

Ala Gln Leu Gly Cys Gly Asn Val Thr Tyr Lys Phe Val Thr Leu His
                85                  90                  95

Lys Pro Lys Gln Gly Ala Asp Thr Tyr Leu Glu Leu Gly Phe Lys Asn
                100                 105                 110

Gly Thr Leu Ala Pro Gly Ala Ser Thr Gly Asn Ile Gln Leu Arg Leu
            115                 120                 125

His Asn Asp Asp Trp Ser Asn Tyr Ala Gln Ser Gly Asp Tyr Ser Phe
    130                 135                 140

Phe Lys Ser Asn Thr Phe Lys Thr Thr Lys Ile Thr Leu Tyr Asp
145                 150                 155                 160

Gln Gly Lys Leu Ile Trp Gly Thr Glu
                165

<210> SEQ ID NO 46
<211> LENGTH: 160
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 46

Ile Leu Gly Thr Lys Asp Ser Thr Lys Asp Ile Pro Glu Thr Pro Ala
1               5                   10                  15

Lys Asp Lys Pro Thr Arg Glu Asn Gly Ile Ser Val Gln Tyr Arg Ala
                20                  25                  30

Gly Asp Gly Ser Met Asn Ser Asn Gln Ile Arg Pro Gln Leu Gln Ile
            35                  40                  45

Lys Asn Asn Gly Asn Thr Thr Val Asp Leu Lys Asp Val Thr Ala Arg
    50                  55                  60

Tyr Trp Tyr Lys Ala Lys Asn Lys Gly Gln Asn Val Asp Cys Asp Tyr
65              70                  75                  80

Ala Gln Ile Gly Cys Gly Asn Val Thr Tyr Lys Phe Val Thr Leu His
                85                  90                  95

Lys Pro Lys Gln Gly Ala Asp Thr Tyr Leu Glu Leu Gly Phe Lys Asn
                100                 105                 110
```

```
Gly Thr Leu Ala Pro Gly Ala Ser Thr Gly Asn Ile Gln Leu Arg Leu
            115                 120                 125

His Asn Asp Asp Trp Ser Asn Tyr Ala Gln Ser Gly Asp Tyr Ser Phe
        130                 135                 140

Phe Lys Ser Asn Thr Phe Lys Thr Thr Lys Ile Thr Leu Tyr Asp
145                 150                 155                 160

<210> SEQ ID NO 47
<211> LENGTH: 169
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 47

Ile Leu Gly Asn Lys Asp Ser Thr Lys Glu Arg Pro Glu Thr Pro Ala
1               5                   10                  15

Gln Asp Asn Pro Ala Gln Glu Asn Gly Ile Ser Val Gln Tyr Lys Ala
            20                  25                  30

Gly Asp Gly Gly Val Asn Ser Asn Gln Ile Arg Pro Gln Leu His Ile
        35                  40                  45

Lys Asn Asn Gly Asn Ala Thr Val Asp Leu Lys Asp Val Thr Ala Arg
    50                  55                  60

Tyr Trp Tyr Asn Ala Lys Asn Lys Gly Gln Asn Phe Asp Cys Asp Tyr
65                  70                  75                  80

Ala Gln Ile Gly Cys Gly Asn Leu Thr His Lys Phe Val Thr Leu His
                85                  90                  95

Lys Pro Lys Gln Gly Ala Asp Thr Tyr Leu Glu Leu Gly Phe Lys Thr
            100                 105                 110

Gly Thr Leu Ser Pro Gly Ala Ser Thr Gly Asn Ile Gln Leu Arg Leu
        115                 120                 125

His Asn Asp Asp Trp Ser Asn Tyr Ala Gln Ser Asp Asp Tyr Ser Phe
    130                 135                 140

Phe Gln Ser Asn Thr Phe Lys Thr Thr Lys Lys Ile Thr Leu Tyr His
145                 150                 155                 160

Gln Gly Lys Leu Ile Trp Gly Thr Glu
                165

<210> SEQ ID NO 48
<211> LENGTH: 82
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 48

Ile Arg Glu Ser Ala Thr Thr Pro Pro Ser Asp Pro Thr Pro Pro Ser
1               5                   10                  15

Asp Pro Asp Pro Gly Glu Pro Glu Asp Pro Gly Pro Glu Pro Asp Pro
            20                  25                  30

Thr Pro Pro Ser Asp Gly Asp Tyr Pro Ala Trp Asp Pro Asn Thr Ile
        35                  40                  45

Tyr Thr Asp Glu Ile Val Tyr His Asn Gly Gln Leu Trp Gln Ala Lys
    50                  55                  60

Trp Trp Thr Gln Asn Gln Glu Pro Gly Asp Tyr Gly Pro Trp Glu Pro
65                  70                  75                  80
```

Leu Asn

```
<210> SEQ ID NO 49
<211> LENGTH: 167
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 49
```

Ile Arg Gly Asn Ala Gln Val Ser Leu Thr Ala Ser Ala Asn Ser Ala
1               5                   10                  15

Gln Ser Gly Gly Ala Ser Thr Gly Asn Leu Val Val Gln Tyr Lys Val
            20                  25                  30

Gly Asp Thr Ser Ala Thr Asp Asn Gln Met Lys Pro Ser Phe Asn Ile
        35                  40                  45

Lys Asn Asn Gly Thr Thr Pro Val Asn Leu Ser Gly Leu Lys Leu Arg
    50                  55                  60

Tyr Tyr Phe Thr Lys Asp Gly Thr Asp Met Ser Ala Ser Ile Asp Trp
65                  70                  75                  80

Ala Gln Ile Gly Ala Ser Asn Ile Ser Ala Ala Phe Ala Asp Phe Thr
                85                  90                  95

Gly Ser Asn Thr Asp Thr Tyr Val Glu Leu Ser Phe Ser Ala Gly Ser
            100                 105                 110

Ile Pro Ala Gly Gly Gln Thr Gly Asp Ile Gln Leu Arg Met Tyr Lys
        115                 120                 125

Thr Asp Trp Ser Asn Phe Asn Glu Ala Asn Asp Tyr Ser Tyr Asp Gly
    130                 135                 140

Ala Lys Thr Tyr Ala Asp Trp Asn Arg Val Thr Leu His Gln Asn Gly
145                 150                 155                 160

Thr Leu Val Trp Gly Thr Thr
                165

```
<210> SEQ ID NO 50
<211> LENGTH: 73
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 50
```

Ile Arg Glu Ser Ala Ser Ile Pro Pro Ser Asp Pro Thr Pro Pro Ser
1               5                   10                  15

Asp Pro Gly Glu Pro Asp Pro Thr Pro Pro Ser Asp Gly Tyr Pro
            20                  25                  30

Ala Trp Asp Pro Asn Gln Ile Tyr Thr Asn Glu Ile Val Tyr His Asn
        35                  40                  45

Gly Gln Leu Trp Gln Ala Lys Trp Trp Thr Gln Asn Gln Glu Pro Gly
    50                  55                  60

Asp Tyr Gly Pro Trp Glu Pro Leu Asn
65                  70

```
<210> SEQ ID NO 51
<211> LENGTH: 166
<212> TYPE: PRT
<213> ORGANISM: Artificial Sequence
<220> FEATURE:
<223> OTHER INFORMATION: Fusion sequence of carbohydrate binding domain
``` and linker domain

<400> SEQUENCE: 51

Leu Arg Gly Ser Gly Gln Ala Ala Leu Ser Gly Gly Pro Val Ser Ala
1               5                   10                  15

Gln Gly Gly Thr Pro Val Pro Gly Ser Leu Val Leu Gln Tyr Arg Ala
            20                  25                  30

Ala Asp Thr Asn Ala Gly Asp Asn Ala Ile Lys Pro His Phe Asn Ile
        35                  40                  45

Arg Asn Thr Gly Ala Ser Pro Val Asp Leu Ser Gly Val Lys Leu Arg
    50                  55                  60

Tyr Tyr Phe Thr Lys Asp Gly Ile Pro Leu Ser Phe Ala Val Asp Trp
65                  70                  75                  80

Ala Gln Val Gly Ser Pro Asn Val Lys Gly Thr Phe Gly Ser Ala Ser
                85                  90                  95

Gly Ala Gly Ala Asp Thr Tyr Leu Glu Val Ser Phe Thr Gly Ser Ile
            100                 105                 110

Pro Ala Gly Gly Gln Thr Gly Glu Ile Gln Thr Arg Ile His Lys Ser
        115                 120                 125

Asp Trp Ser Ser Phe Gln Glu Ser Gly Asp Tyr Ser Tyr Asp Pro Gly
    130                 135                 140

Lys Thr Tyr Ala Asp Trp Ser Lys Val Thr Leu Tyr Arg Asp Gly Thr
145                 150                 155                 160

Arg Val Trp Gly Val Glu
                165

<210> SEQ ID NO 52
<211> LENGTH: 169
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 52

Ile Gly Gly Ser Asn Thr Thr Ser Gln Thr Tyr Lys Ala Phe Thr Thr
1               5                   10                  15

Lys Thr Gly Met Thr Asp Ser Asn Ile Thr Ser Ala Val Tyr Thr Ile
            20                  25                  30

Ser Asn Thr Asp Pro Val Lys Gln Val Ser Ala Pro Thr Phe Ser Leu
        35                  40                  45

Gln Ser Ala Gln Thr Val Thr Leu Thr Ser Ser Asp Asn Asp Ser Val
    50                  55                  60

Ile His Tyr Thr Thr Asp Gly Thr Pro Thr Ser Ser Pro Val Tyr
65                  70                  75                  80

Thr Asn Met Thr Asp Ser Ser Val Val Thr Asn Thr Tyr Thr Ile Thr
                85                  90                  95

Asn Glu Thr Ser Asn Ser Pro Val Glu Val Glu Val Tyr Lys Thr
            100                 105                 110

Thr Val Lys Val Thr Leu Thr Asn Asn Ser Ser Thr Pro Ile Asn Gly
        115                 120                 125

Trp Lys Leu Ser Trp Ile Asn Asn Met Trp Thr Ala Asn Tyr Ser Ile
    130                 135                 140

Lys Asp Ser Ala Ile Val Lys Asp Tyr Asn Asn Ile Ile Pro Ala Asn
145                 150                 155                 160

Gly Gly Thr Gln Ile Phe Gly Phe Ser
                165

<210> SEQ ID NO 53
<211> LENGTH: 168
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 53

Ile Leu Glu Gly Ser Asn Asn Thr Gly Asn Asp Asn Gly Gly Ser
1               5                   10                  15

Thr Leu Gly Gly Asp Asn Gln Gly Ile Val Leu Gln Tyr Arg Thr Gly
                20                  25                  30

Asp Thr Asn Thr Lys Asp Asn Ala Ile Arg Pro Glu Phe Asn Ile Lys
            35                  40                  45

Asn Thr Gly Asn Thr Ala Val Lys Leu Ser Asp Leu Lys Ile Arg Tyr
        50                  55                  60

Tyr Tyr Thr Asp Glu Ser Lys Gly Gln Gln Leu Phe Val Asp Trp Ala
65                  70                  75                  80

Lys Val Gly Asn Glu Lys Val Lys Ala Thr Phe Val Ala Leu Pro Glu
                85                  90                  95

Pro Lys Ala Lys Ala Asp Lys Tyr Val Glu Ile Ser Phe Thr Asp Gly
            100                 105                 110

Thr Ile Gln Pro Gly Gly Glu Ser Gly Glu Ile Gln Pro Arg Ile His
        115                 120                 125

Ala Ala Asn Trp Ser Asn Phe Asp Glu Thr Asn Asp Tyr Ser Tyr Gly
    130                 135                 140

Ala Ser Gln Thr Phe Ala Asn Trp Asp His Ala Thr Val Tyr Gln Gln
145                 150                 155                 160

Gly Lys Leu Val Trp Gly Ile Glu
                165

<210> SEQ ID NO 54
<211> LENGTH: 165
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 54

Ile Leu Glu Gly Ser Ser Asn His Gly Gly Gly Thr Pro Gly
1               5                   10                  15

Gly Asn Asn Glu Gly Ile Val Leu Gln Tyr Arg Thr Asp Thr Asn
                20                  25                  30

Ala Lys Asp Asn Ala Ile Arg Pro Gln Phe Asn Ile Lys Asn Thr Gly
            35                  40                  45

Lys Thr Ala Val Lys Leu Ser Asp Leu Lys Ile Arg Tyr Tyr Tyr Thr
        50                  55                  60

Asp Glu Ser Lys Ala Gln Gln Phe Phe Val Asp Trp Ala Lys Ile Gly
65                  70                  75                  80

Asn Glu Lys Val Lys Ala Thr Phe Val Thr Leu Pro Asn Pro Lys Ser
                85                  90                  95

Lys Ala Asp Lys Tyr Val Glu Ile Ser Phe Thr Asp Gly Thr Ile Gln
            100                 105                 110

Pro Gly Gly Glu Thr Gly Glu Ile Gln Ser Arg Ile His Ala Ala Asn

```
            115                 120                 125

Trp Ser Asn Phe Asp Glu Thr Asn Asp Tyr Ser Tyr Gly Ala Ala Gln
    130                 135                 140

Thr Phe Ala Asp Trp Asp His Gly Thr Val Tyr Gln Gln Gly Lys Leu
145                 150                 155                 160

Val Trp Gly Ile Glu
                165

<210> SEQ ID NO 55
<211> LENGTH: 125
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 55

Gln Ala Ala Gly Leu Thr Ala Thr Val Thr Lys Glu Ser Ser Trp Asp
1               5                   10                  15

Asn Gly Tyr Ser Ala Ser Val Thr Val Arg Asn Asp Thr Ser Ser Val
                20                  25                  30

Ser Gln Trp Glu Val Val Leu Thr Leu Pro Gly Gly Thr Thr Val Ala
            35                  40                  45

Gln Val Trp Asn Ala Gln His Thr Ser Ser Gly Asn Ser His Thr Phe
        50                  55                  60

Thr Gly Val Ser Trp Asn Ser Thr Ile Pro Pro Gly Gly Thr Ala Ser
65                  70                  75                  80

Phe Gly Phe Ile Ala Ser Gly Ser Gly Glu Pro Thr His Cys Thr Ile
                85                  90                  95

Asn Gly Ala Pro Cys Asp Glu Gly Ser Glu Pro Gly Pro Gly Gly Pro
                100                 105                 110

Gly Thr Pro Ser Pro Asp Pro Thr Gln Pro Gly Thr Thr
            115                 120                 125

<210> SEQ ID NO 56
<211> LENGTH: 121
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 56

Ala Ala Thr Gly Cys Ser Val Thr Tyr Thr Thr Asn Ser Trp Ser Asn
1               5                   10                  15

Gly Phe Thr Ala Asn Val Thr Val Thr Asn Leu Gly Asp Ala Ile Gly
                20                  25                  30

Asn Trp Thr Leu Gly Phe Ser Phe Pro Ser Gly Gln Arg Val Thr Gln
            35                  40                  45

Gly Trp Ser Ala Ile Trp Ser Gln Ser Gly Asn Ala Val Thr Ala Arg
        50                  55                  60

Ser Glu Ser Trp Asn Gly Asn Leu Ala Thr Gly Ala Ser Thr Ser Ile
65                  70                  75                  80

Gly Phe Asn Gly Ser Phe Thr Gly Ser Pro Thr Ser Phe Thr Leu Asn
                85                  90                  95

Gly Val Pro Cys Thr Gly Ser Thr Thr Pro Pro Thr Pro
                100                 105                 110

Pro Pro Pro Thr Thr Pro Pro Pro Gln
```

```
                115                 120

<210> SEQ ID NO 57
<211> LENGTH: 121
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 57

Glu Ala Ala Ser Phe Thr Val Thr Asn Ser Trp Ser Thr Gly Tyr Gln
1               5                   10                  15

Gly Glu Val Thr Val Ser Asn Pro Ala Ser Ser Ile Asn Thr Trp Lys
            20                  25                  30

Val Gln Leu Thr Leu Pro Ala Gly Ser Thr Ile Gly Gln Ala Trp Asn
        35                  40                  45

Ala Thr Leu Ala Thr Gly Gly Gln Thr Phe Thr Phe Thr Pro Ala Gly
    50                  55                  60

Trp Asn Gly Thr Ile Ala Gly Gly Ser Ala Thr Ser Phe Gly Phe Val
65                  70                  75                  80

Val Thr Gly Thr Gly Arg Pro Thr Ser Cys Thr Val Asn Gly Gln Ala
                85                  90                  95

Cys Thr Gly Leu Thr Gly Ala Pro Gly Lys Thr Pro Thr Ser Ala Pro
            100                 105                 110

Ala Thr Ala Thr Thr Ala Ser Pro Gly
        115                 120

<210> SEQ ID NO 58
<211> LENGTH: 113
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 58

Ala Ala Thr Gly Cys His Val Asp Tyr Thr Val Thr Asn Gln Trp Gln
1               5                   10                  15

Gly Gly Phe Gln Ala Ala Val Lys Val Thr Asn Leu Gly Asp Ala Ile
            20                  25                  30

Thr Gly Trp Leu Leu Arg Phe Thr Phe Pro Ala Gly Gln Lys Val Ala
        35                  40                  45

Gln Gly Trp Asn Ala Thr Trp Ala Gln Ser Gly Ala Thr Ala Thr Ala
    50                  55                  60

Ala Asn Ala Asp Trp Asn Arg Thr Leu Thr Gly Ala Thr Thr Glu
65                  70                  75                  80

Leu Gly Phe Thr Gly Thr Thr Thr Gly Val Pro Ala Ser Phe Thr Leu
                85                  90                  95

Asn Gly Val Thr Cys Thr Gly Ser Thr Thr Thr Thr Thr Thr Thr Thr
            100                 105                 110

Gly

<210> SEQ ID NO 59
<211> LENGTH: 124
<212> TYPE: PRT
<213> ORGANISM: Artificial Sequence
<220> FEATURE:
<223> OTHER INFORMATION: Fusion sequence of carbohydrate binding domain
      and linker domain
```

<400> SEQUENCE: 59

Ala Ala Thr Gly Cys Ala Val Thr Tyr Thr Asn Ser Trp Gln Gly
1               5                   10                  15

Gly Phe Thr Ala Thr Val Ala Val Arg Asn Leu Gly Asp Pro Val Ser
            20                  25                  30

Asn Trp Thr Leu Gly Phe Thr Phe Pro Gly Gly Gln Arg Val Val Gln
        35                  40                  45

Gly Trp Ser Ala Thr Trp Gln Gln Ser Gly Ser Ala Val Thr Ala Arg
50                  55                  60

Ser Leu Asp Tyr Asn Gly Ala Leu Gly Thr Gly Ala Ser Thr Thr Ile
65                  70                  75                  80

Gly Phe Asn Gly Ser Trp Thr Gly Ser Pro Thr Ser Phe Thr Leu Asn
                85                  90                  95

Gly Thr Val Cys Thr Gly Gly Thr Ser Thr Ser Thr Pro Pro Pro Pro
            100                 105                 110

Thr Thr Pro Pro Pro Pro Thr Pro Pro Pro Thr
            115                 120

<210> SEQ ID NO 60
<211> LENGTH: 116
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 60

Glu Ser Glu Asn Ala Thr Ile Ser Arg Gly Val Val Glu Ala Asn His
1               5                   10                  15

Thr Gly Phe Thr Gly Ser Gly Phe Val Asn Tyr Asp Asn Val Thr Gly
            20                  25                  30

Ser Tyr Val Glu Tyr Thr Val Asn Ala Ala Gln Ala Gly Pro His Thr
        35                  40                  45

Leu Thr Phe Arg Tyr Ala Asn Gly Thr Thr Ala Asn Arg Pro Leu Asp
    50                  55                  60

Ile Thr Val Asn Gly Ser Ile Ala Val Asp Asp Leu Gly Phe Ala Gly
65                  70                  75                  80

Thr Gly Ala Trp Ser Thr Val Thr Thr Val Asn Leu Ala Ala Gly
                85                  90                  95

Ser Asn Lys Ile Gly Gly Pro Asn Ala Asp Ser Leu Ser Val Glu Gly
            100                 105                 110

Gly Gly Pro Gly
        115

<210> SEQ ID NO 61
<211> LENGTH: 113
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 61

Asn Ala Ala Gly Cys Arg Val Asp Tyr Thr Val Thr Asn Gln Trp Gln
1               5                   10                  15

Gly Gly Phe Gln Ala Gly Val Lys Ile Thr Asn Leu Gly Asp Thr Val
            20                  25                  30

Arg Gly Trp Thr Leu Lys Phe Thr Leu Pro Thr Gly Gln Lys Val Val
             35                  40                  45

Gln Gly Trp Ser Ala Ala Trp Ser Gln Ser Gly Ser Thr Val Thr Val
 50                  55                  60

Ala Gly Ala Asp Trp Asn Gly Thr Leu Ala Thr Gly Ala Ser Ala Asp
 65                  70                  75                  80

Thr Gly Phe Val Gly Ser Phe Thr Gly Lys Pro Thr Ala Phe Thr Leu
                 85                  90                  95

Asn Gly Val Ala Cys Thr Gly Ser Val Asp Asp Thr Pro Pro Pro Ser
            100                 105                 110

Gly

<210> SEQ ID NO 62
<211> LENGTH: 116
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 62

Ala Ala Thr Gly Cys Lys Ala Glu Tyr Thr Ile Thr Ser Gln Trp Glu
 1               5                  10                  15

Gly Gly Phe Gln Ala Gly Val Lys Ile Thr Asn Leu Gly Asp Pro Val
             20                  25                  30

Ser Gly Trp Thr Leu Gly Phe Thr Met Pro Ala Gly Gln Arg Leu Val
             35                  40                  45

Gln Gly Trp Asn Ala Thr Trp Ser Gln Ser Gly Ser Ala Val Thr Ala
 50                  55                  60

Gly Gly Val Asp Trp Asn Arg Thr Leu Ala Thr Gly Ala Ser Ala Asp
 65                  70                  75                  80

Leu Gly Phe Val Gly Ser Phe Thr Gly Ala Pro Thr Ser Phe Thr Leu
                 85                  90                  95

Asn Gly Ala Thr Cys Ser Gly Ser Val Thr Asp Pro Pro Thr Asp Pro
            100                 105                 110

Pro Thr Pro Ala
            115

<210> SEQ ID NO 63
<211> LENGTH: 83
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 63

Arg Asp Trp Ser Asp Asp Gly Ile Gln Thr Glu Ser Thr Thr Asp Thr
 1               5                  10                  15

Gly Gly Gly Leu Asn Ile Gly Trp Thr Asp Ala Gly Asp Trp Thr Ser
             20                  25                  30

Pro Ala Ala Gly Arg Tyr Lys Val Ser Tyr Arg Asn Ser Gly Met Leu
             35                  40                  45

Gln Leu Glu Ala Ala Gly Gly Phe Pro Thr Tyr Gly Ser Ile Thr Gly
 50                  55                  60

Gly Trp Gln Ser Trp Gln Thr Ile Ser His Glu Val Asn Leu Asn Trp
 65                  70                  75                  80

Ile Lys Val

<210> SEQ ID NO 64
<211> LENGTH: 83
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 64

```
Arg Ala Gly Ala Asp Pro Thr Glu Pro Thr Asn Pro Gly Asn Gly Thr
1               5                   10                  15

Thr Gly Asp Val Val Leu Gln Tyr Arg Asn Val Asp Asn Asn Pro Ser
            20                  25                  30

Asp Asp Ala Ile Arg Met Ala Val Asn Ile Lys Asn Thr Gly Ser Thr
        35                  40                  45

Pro Ile Lys Leu Ser Asp Leu Gln Val Arg Tyr Tyr Phe His Asp Asp
    50                  55                  60

Gly Lys Pro Gly Ala Asn Leu Phe Val Asp Trp Ala Asn Val Gly Pro
65                  70                  75                  80

Asn Asn Ile
```

<210> SEQ ID NO 65
<211> LENGTH: 83
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 65

```
Arg Ala Gly Ala Asn Pro Thr Glu Pro Thr Asn Pro Gly Asn Gly Thr
1               5                   10                  15

Thr Gly Asp Val Val Leu Gln Tyr Arg Asn Val Asp Asn Asn Pro Ser
            20                  25                  30

Asp Asp Ala Ile Arg Met Ala Val Asn Ile Lys Asn Thr Gly Ser Thr
        35                  40                  45

Pro Ile Lys Leu Ser Asp Leu Gln Val Arg Tyr Tyr Phe His Asp Asp
    50                  55                  60

Gly Lys Pro Gly Ala Asn Leu Phe Val Asp Trp Ala Asn Val Gly Pro
65                  70                  75                  80

Asn Asn Ile
```

<210> SEQ ID NO 66
<211> LENGTH: 83
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 66

```
Arg Ala Gly Ala Gly Pro Thr Glu Pro Thr Asn Pro Gly Asn Gly Thr
1               5                   10                  15

Thr Gly Asp Ile Val Leu Gln Tyr Arg Asn Val Asp Asn Asn Pro Ser
            20                  25                  30

Asp Asp Ala Ile Arg Met Ala Phe Asn Ile Lys Asn Thr Gly Ser Thr
        35                  40                  45

Pro Ile Lys Leu Ser Asp Leu Gln Val Arg Tyr Tyr Phe His Asp Asp
    50                  55                  60
```

Gly Lys Pro Gly Ala Asn Leu Phe Val Asp Trp Ala Asn Val Gly Pro
65                  70                  75                  80

Asn Asn Ile

<210> SEQ ID NO 67
<211> LENGTH: 80
<212> TYPE: PRT
<213> ORGANISM: Artificial Sequence
<220> FEATURE:
<223> OTHER INFORMATION: Fusion sequence of carbohydrate binding domain
      and linker domain

<400> SEQUENCE: 67

Ser Gly Trp Pro Ser Ser Ser Ala Val Ser Ser Gln Thr Gln
1               5                   10                  15

Val Ser Ser Ser Gln Ala Pro Val Val Ser Ser Ser Ser Thr
            20                  25                  30

Ala Ser Ser Val Val Ser Ser Ala Val Ser Gly Tyr Gly Thr Leu Tyr
            35                  40                  45

Pro Leu Cys Ser Thr Thr Thr Asn Gly Trp Gly Trp Glu Asn Asn Ala
    50                  55                  60

Ser Cys Ile Ala Arg Ala Thr Cys Ser Gly Gln Pro Ser Ser Ser Val
65                  70                  75                  80

<210> SEQ ID NO 68
<211> LENGTH: 30
<212> TYPE: PRT
<213> ORGANISM: Artificial Sequence
<220> FEATURE:
<223> OTHER INFORMATION: Linker domain

<400> SEQUENCE: 68

Pro Thr Thr Ser Pro Thr Pro Thr Pro Thr Pro Thr Pro Thr Pro
1               5                   10                  15

Thr Pro Thr Pro Thr Pro Thr Pro Thr Pro Val Thr Pro
            20                  25                  30

<210> SEQ ID NO 69
<211> LENGTH: 297
<212> TYPE: PRT
<213> ORGANISM: Artificial
<220> FEATURE:
<223> OTHER INFORMATION: Endocellulase catalytic domain

<400> SEQUENCE: 69

Thr Pro Val Glu Thr His Gly Gln Leu Ser Val Lys Gly Gly Gln Leu
1               5                   10                  15

Val Asp Glu Asn Gly Lys Pro Val Gln Leu Arg Gly Met Ser Ser His
            20                  25                  30

Gly Leu Gln Trp Phe Gly Asp Phe Val Asn Lys Asp Ser Met Lys Trp
        35                  40                  45

Leu Arg Asp Asp Trp Gly Ile Asn Val Phe Arg Val Ala Met Tyr Thr
    50                  55                  60

Ala Glu Asp Gly Tyr Ile Thr Asn Pro Ser Val Lys Asn Lys Val Lys
65                  70                  75                  80

Glu Ala Val Glu Ala Ala Ile Asp Leu Gly Met Tyr Val Ile Ile Asp
                85                  90                  95

Trp His Ile Leu Ser Asp Asn Asp Pro Asn Thr Tyr Lys Ala Gln Ala
                100                 105                 110

-continued

```
Lys Ala Phe Phe Gln Glu Met Ala Ala Leu Tyr Gly Asn Tyr Pro Asn
            115                 120                 125

Val Ile Tyr Glu Ile Ala Asn Glu Pro Asn Gly Asn Val Thr Trp Asn
        130                 135                 140

Asn Gln Ile Lys Pro Tyr Ala Glu Glu Val Ile Pro Val Ile Arg Ala
145                 150                 155                 160

Lys Asp Pro Asp Asn Ile Ile Ile Val Gly Thr Gly Thr Trp Ser Gln
                165                 170                 175

Asp Val His Asp Ala Ala Asp Asn Pro Leu Pro Asp Ser Asn Ile Met
            180                 185                 190

Tyr Ala Leu His Phe Tyr Ala Gly Thr His Gly Gln Phe Leu Arg Asp
            195                 200                 205

Arg Ile Asp Tyr Ala Leu Ser Lys Gly Ala Ala Ile Phe Val Thr Glu
        210                 215                 220

Trp Gly Thr Ser Asp Ala Ser Gly Asn Gly Gly Pro Phe Leu Pro Glu
225                 230                 235                 240

Ser Gln Glu Trp Ile Asp Phe Met Asn Ser Arg Lys Ile Ser Trp Ala
                245                 250                 255

Asn Trp Ser Leu Ser Asp Lys Ser Glu Thr Ser Ala Ala Leu Met Pro
            260                 265                 270

Gly Ala Ser Pro Thr Gly Gly Trp Thr Glu Ser Gln Leu Ser Ala Ser
            275                 280                 285

Gly Lys Phe Val Arg Glu Gln Ile Arg
290                 295
```